US010226451B2

(12) United States Patent
Liu et al.

(10) Patent No.: US 10,226,451 B2
(45) Date of Patent: Mar. 12, 2019

(54) SUBSTITUTED BICYCLIC COMPOUNDS AS BROMODOMAIN INHIBITORS

(71) Applicant: ZENITH EPIGENETICS LTD, Calgary (CA)

(72) Inventors: Shuang Liu, Schenectady, NY (US); John Frederick Quinn, Albany, NY (US); Bryan Cordell Duffy, Glenmont, NY (US); Ruifang Wang, Schenectady, NY (US); May Xiaowu Jiang, Guilderland, NY (US); Gregory Scott Martin, Colonie, NY (US); He Zhao, Madison, CT (US); Michael Ellis, Clifton Park, NY (US); Gregory Steven Wagner, Foster City, CA (US); Peter Ronald Young, San Francisco, CA (US)

(73) Assignee: Zenith Epigenetics Ltd., Calgary, Alberta (CA)

( * ) Notice: Subject to any disclaimer, the term of this patent is extended or adjusted under 35 U.S.C. 154(b) by 0 days.

(21) Appl. No.: 15/459,886

(22) Filed: Mar. 15, 2017

(65) Prior Publication Data

US 2017/0182029 A1    Jun. 29, 2017

Related U.S. Application Data

(62) Division of application No. 14/900,138, filed as application No. PCT/IB2014/002240 on Jun. 20, 2014, now Pat. No. 9,636,328.
(Continued)

(51) Int. Cl.
| | |
|---|---|
| A61K 31/4709 | (2006.01) |
| A61K 45/06 | (2006.01) |
| A61K 31/4439 | (2006.01) |
| A61K 31/422 | (2006.01) |
| A61K 31/423 | (2006.01) |
| A61K 31/4184 | (2006.01) |
| C07D 405/14 | (2006.01) |
| C07D 403/14 | (2006.01) |
| C07D 405/04 | (2006.01) |
| C07D 417/14 | (2006.01) |
| C07D 471/04 | (2006.01) |
| A61K 31/427 | (2006.01) |
| C07D 413/04 | (2006.01) |
| C07D 413/14 | (2006.01) |
| A61K 31/426 | (2006.01) |
| A61K 31/428 | (2006.01) |
| A61K 31/437 | (2006.01) |
| A61K 31/4725 | (2006.01) |
| A61K 31/496 | (2006.01) |
| A61K 31/497 | (2006.01) |
| A61K 31/4985 | (2006.01) |
| A61K 31/501 | (2006.01) |
| A61K 31/506 | (2006.01) |
| A61K 31/517 | (2006.01) |
| A61K 31/5377 | (2006.01) |
| A61K 31/538 | (2006.01) |
| C07D 409/14 | (2006.01) |

(Continued)

(52) U.S. Cl.
CPC ........ *A61K 31/4184* (2013.01); *A61K 31/422* (2013.01); *A61K 31/423* (2013.01); *A61K 31/426* (2013.01); *A61K 31/427* (2013.01); *A61K 31/428* (2013.01); *A61K 31/437* (2013.01); *A61K 31/4439* (2013.01); *A61K 31/454* (2013.01); *A61K 31/4709* (2013.01); *A61K 31/4725* (2013.01); *A61K 31/496* (2013.01); *A61K 31/497* (2013.01); *A61K 31/4985* (2013.01); *A61K 31/501* (2013.01); *A61K 31/506* (2013.01); *A61K 31/517* (2013.01); *A61K 31/538* (2013.01); *A61K 31/5377* (2013.01); *A61K 45/06* (2013.01); *C07D 403/14* (2013.01); *C07D 405/04* (2013.01); *C07D 405/14* (2013.01); *C07D 409/14* (2013.01); *C07D 413/04* (2013.01); *C07D 413/14* (2013.01); *C07D 417/14* (2013.01); *C07D 471/04* (2013.01); *C07D 487/04* (2013.01); *Y02A 50/467* (2018.01)

(58) Field of Classification Search
None
See application file for complete search history.

(56) References Cited

U.S. PATENT DOCUMENTS

| 4,748,163 A | 5/1988 | Schmidt et al. |
| 5,385,925 A | 1/1995 | Narr et al. |

(Continued)

FOREIGN PATENT DOCUMENTS

| CA | 2087800 A1 | 7/1993 |
| CA | 2093785 A1 | 10/1993 |

(Continued)

OTHER PUBLICATIONS

Horig et al. Journal of Translational Medicine 2004, 2(44), p. 1-8.*
(Continued)

*Primary Examiner* — Yong L Chu
(74) *Attorney, Agent, or Firm* — Finnegan, Henderson, Farabow, Garrett & Dunner, LLP

(57) ABSTRACT

The invention relates to substituted bicyclic compounds, which are useful for inhibition of BET protein function by binding to bromodomains, pharmaceutical compositions comprising these compounds, and use of the compounds and compositions in therapy.

5 Claims, No Drawings

Related U.S. Application Data

(60) Provisional application No. 61/911,668, filed on Dec. 4, 2013, provisional application No. 61/837,830, filed on Jun. 21, 2013.

(51) Int. Cl.
  *C07D 487/04* (2006.01)
  *A61K 31/454* (2006.01)

(56) References Cited

U.S. PATENT DOCUMENTS

| | | |
|---|---|---|
| 5,565,469 A | 10/1996 | Mihm et al. |
| 5,591,762 A | 1/1997 | Hauel et al. |
| 6,380,235 B1 | 4/2002 | Zhang et al. |
| 8,053,440 B2 | 11/2011 | Hansen |
| 8,093,273 B2 | 1/2012 | Wong et al. |
| 8,691,747 B2 | 4/2014 | Kruidenier et al. |
| 8,697,725 B2 | 4/2014 | Demont et al. |
| 8,735,586 B2 | 5/2014 | Alonso et al. |
| 8,993,554 B2 | 3/2015 | Amans et al. |
| 9,029,395 B2 | 5/2015 | Amans et al. |
| 9,067,936 B2 | 6/2015 | Demont et al. |
| 9,073,878 B2 | 7/2015 | Fairfax et al. |
| 9,102,677 B2 | 8/2015 | Bailey et al. |
| 9,125,915 B2 | 9/2015 | Miyoshi et al. |
| 9,271,978 B2 | 3/2016 | Liu et al. |
| 9,278,940 B2 | 3/2016 | Fairfax et al. |
| 9,315,487 B2 | 4/2016 | Amans et al. |
| 9,321,765 B2 | 4/2016 | Gong |
| 9,388,161 B2 | 7/2016 | Bair et al. |
| 9,393,232 B2 | 7/2016 | Ren et al. |
| 9,422,281 B2 | 8/2016 | Bair et al. |
| 9,458,145 B2 | 10/2016 | Aktoudianakis et al. |
| 9,458,156 B2 | 10/2016 | Norris et al. |
| 9,598,367 B2 | 3/2017 | Liu et al. |
| 9,636,328 B2 | 5/2017 | Liu et al. |
| 9,662,311 B2 | 5/2017 | Liu et al. |
| 9,663,520 B2 | 5/2017 | Quinn et al. |
| 9,718,847 B2 | 8/2017 | Zhang et al. |
| 9,765,039 B2 | 9/2017 | Fairfax et al. |
| 9,855,271 B2 | 1/2018 | Quinn et al. |
| 9,861,637 B2 | 1/2018 | Liu et al. |
| 2002/0019395 A1 | 2/2002 | Zhu et al. |
| 2003/0036545 A1 | 2/2003 | Castelhano et al. |
| 2004/0044203 A1 | 3/2004 | Wittman et al. |
| 2004/0166137 A1 | 8/2004 | Lackey |
| 2005/0014812 A1 | 1/2005 | Hayashida et al. |
| 2005/0176858 A1 | 8/2005 | Nohara et al. |
| 2006/0178374 A1 | 8/2006 | Cui et al. |
| 2007/0134161 A1 | 6/2007 | Brown |
| 2007/0275984 A1 | 11/2007 | Imogai et al. |
| 2008/0015196 A1 | 1/2008 | Doller et al. |
| 2008/0262207 A1 | 10/2008 | Duffin et al. |
| 2010/0267714 A1 | 10/2010 | Jorgensen et al. |
| 2011/0070297 A1 | 3/2011 | Cao et al. |
| 2011/0136834 A1 | 6/2011 | Critchley et al. |
| 2012/0004261 A1 | 1/2012 | Jorgensen et al. |
| 2012/0028912 A1 | 2/2012 | Zhou et al. |
| 2012/0157428 A1 | 6/2012 | Albrecht et al. |
| 2012/0208798 A1 | 8/2012 | Demont et al. |
| 2012/0208800 A1 | 8/2012 | Chung et al. |
| 2012/0208814 A1 | 8/2012 | Demont et al. |
| 2012/0220573 A1 | 8/2012 | Gosmini et al. |
| 2013/0085133 A1 | 4/2013 | Severson et al. |
| 2013/0143880 A1 | 6/2013 | Dudkin et al. |
| 2013/0261109 A1 | 10/2013 | Miyoshi et al. |
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |
| 2014/0031336 A1 | 1/2014 | Amans et al. |
| 2014/0045834 A1 | 2/2014 | Demont et al. |
| 2014/0162971 A1 | 6/2014 | Wang et al. |
| 2014/0171462 A1 | 6/2014 | Demont et al. |
| 2014/0256700 A1 | 9/2014 | Poss et al. |
| 2014/0256705 A1 | 9/2014 | Hasvold et al. |
| 2014/0256706 A1 | 9/2014 | Wang et al. |
| 2014/0256710 A1 | 9/2014 | Liu et al. |
| 2014/0275030 A1 | 9/2014 | Combs et al. |
| 2014/0275079 A1 | 9/2014 | Hasvold et al. |
| 2014/0296229 A1 | 10/2014 | Engelhardt et al. |
| 2014/0296246 A1 | 10/2014 | Aktoudianakis et al. |
| 2014/0303121 A1 | 10/2014 | Zhang et al. |
| 2014/0336190 A1 | 11/2014 | Aktoudianakis et al. |
| 2014/0349990 A1 | 11/2014 | Blank et al. |
| 2015/0011540 A1 | 1/2015 | Combs et al. |
| 2015/0216168 A1 | 8/2015 | Frackenpohl et al. |
| 2015/0246919 A1 | 9/2015 | Engelhardt et al. |
| 2016/0137613 A1 | 5/2016 | Hansen |
| 2016/0193218 A1 | 7/2016 | Quinn et al. |
| 2017/0143731 A1 | 5/2017 | Liu et al. |
| 2017/0216257 A1 | 8/2017 | Liu et al. |
| 2017/0216301 A1 | 8/2017 | Quinn et al. |
| 2017/0320866 A1 | 11/2017 | Jiang et al. |
| 2017/0360756 A1 | 12/2017 | Brown et al. |
| 2017/0360760 A1 | 12/2017 | Kharenko et al. |
| 2017/0360765 A1 | 12/2017 | Jiang et al. |
| 2018/0092924 A1 | 4/2018 | Quinn et al. |
| 2018/0161337 A1 | 6/2018 | Quinn et al. |

FOREIGN PATENT DOCUMENTS

| | | |
|---|---|---|
| CA | 2195107 A1 | 2/1996 |
| CA | 2440211 A1 | 9/2002 |
| CA | 2911408 A1 | 11/2014 |
| CN | 1113235 A | 12/1995 |
| CN | 1636977 A | 7/2005 |
| CN | 1263757 C | 7/2006 |
| CN | 1934092 A | 3/2007 |
| CN | 101061098 A | 10/2007 |
| CN | 101220077 A | 7/2008 |
| CN | 101384593 A | 3/2009 |
| CN | 101636386 A | 1/2010 |
| CN | 101641339 A | 2/2010 |
| CN | 101983198 A | 3/2011 |
| CN | 102186833 A | 9/2011 |
| CN | 105102453 A | 11/2015 |
| EP | 0 385 850 A2 | 9/1990 |
| EP | 0 556 789 A2 | 8/1993 |
| EP | 0 566 020 A1 | 10/1993 |
| EP | 0 195 947 B1 | 4/1996 |
| EP | 1 375 486 A1 | 1/2004 |
| EP | 1 944 311 A1 | 7/2008 |
| EP | 2 792 355 A1 | 10/2014 |
| JP | S61-207388 A | 9/1986 |
| JP | H04-253966 A | 9/1992 |
| JP | H04-346978 A | 12/1992 |
| JP | H05-279341 A | 10/1993 |
| JP | 2000-072675 A | 3/2000 |
| JP | 2003-523353 A | 8/2003 |
| JP | 2004-519512 A | 7/2004 |
| JP | 2004-524350 A | 8/2004 |
| JP | 2004-526727 A | 9/2004 |
| JP | 2004-534010 A | 11/2004 |
| JP | 2006-511600 A | 4/2006 |
| JP | 2006-522119 A | 9/2006 |
| JP | 2006-528677 A | 12/2006 |
| JP | 2007-530477 A | 11/2007 |
| JP | 2008-513414 A | 5/2008 |
| JP | 2008-169212 A | 7/2008 |
| JP | 2008-533151 A | 8/2008 |
| JP | 2009-517438 A | 4/2009 |
| JP | 2009-528989 A | 8/2009 |
| JP | 2009-532424 A | 9/2009 |
| JP | 2010-513224 A | 4/2010 |
| JP | 2010-532768 A | 10/2010 |
| JP | 2010-540590 A | 12/2010 |
| JP | 2012-500260 A | 1/2012 |
| JP | 2012-513418 A | 6/2012 |
| JP | 2012-520867 A | 9/2012 |
| JP | 2012-520884 A | 9/2012 |
| JP | 2015-532650 A | 11/2015 |
| JP | 2016-515584 A | 5/2016 |
| JP | 2016-520062 A | 7/2016 |

(56) References Cited

FOREIGN PATENT DOCUMENTS

| | | |
|---|---|---|
| JP | 2016-522246 A | 7/2016 |
| JP | 2016-523259 A | 8/2016 |
| JP | 2016-525078 A | 8/2016 |
| KR | 10-1165996 B1 | 10/2011 |
| KR | 10-1242572 B1 | 4/2012 |
| WO | WO 96/33194 A1 | 10/1996 |
| WO | WO 00/34248 A1 | 6/2000 |
| WO | WO 00/66564 A1 | 11/2000 |
| WO | WO 01/55132 A1 | 8/2001 |
| WO | WO 02/057267 A1 | 7/2002 |
| WO | WO 02/070486 A1 | 9/2002 |
| WO | WO 02/072576 A1 | 9/2002 |
| WO | WO 02/076976 A2 | 10/2002 |
| WO | WO 02/079192 A1 | 10/2002 |
| WO | WO 2004/024897 A2 | 3/2004 |
| WO | WO 2004/054984 A1 | 7/2004 |
| WO | WO 2004/078733 A1 | 9/2004 |
| WO | WO 2004/098494 A2 | 11/2004 |
| WO | WO 2004/108686 A2 | 12/2004 |
| WO | WO 2005/012292 | 2/2005 |
| WO | WO 2005/013950 A2 | 2/2005 |
| WO | WO 2005/080380 A1 | 9/2005 |
| WO | WO 2005/090317 A1 | 9/2005 |
| WO | WO 2005/121132 A1 | 12/2005 |
| WO | WO 2006/021886 A1 | 3/2006 |
| WO | WO 2006/030032 A1 | 3/2006 |
| WO | WO 2006/099379 A2 | 9/2006 |
| WO | WO 2007/016525 A2 | 2/2007 |
| WO | WO 2007/040208 A1 | 4/2007 |
| WO | WO 2007/063012 A1 | 6/2007 |
| WO | WO 2007/093901 A1 | 8/2007 |
| WO | WO 2007/113232 A1 | 10/2007 |
| WO | WO 2008/072784 A1 | 6/2008 |
| WO | WO 2008/092231 A1 | 8/2008 |
| WO | WO 2008/153701 A1 | 12/2008 |
| WO | WO 2009/043883 A1 | 4/2009 |
| WO | WO 2009/079001 A1 | 6/2009 |
| WO | WO 2009/099801 A1 | 8/2009 |
| WO | WO 2010/021693 A2 | 2/2010 |
| WO | WO 2010/068483 A2 | 6/2010 |
| WO | WO 2010/106436 A2 | 9/2010 |
| WO | WO 2010/107739 A2 | 9/2010 |
| WO | WO 2010/123975 A1 | 10/2010 |
| WO | WO 2011/054843 A1 | 5/2011 |
| WO | WO 2011/054846 A1 | 5/2011 |
| WO | WO 2011/143669 A2 | 11/2011 |
| WO | WO 2012/003576 A1 | 1/2012 |
| WO | WO 2012/009258 A2 | 1/2012 |
| WO | WO 2012/021382 A1 | 2/2012 |
| WO | WO-2012021382 A1 * | 2/2012 ........... C07D 235/26 |
| WO | WO 2012/075456 A1 | 6/2012 |
| WO | WO 2012/143413 A1 | 10/2012 |
| WO | WO 2012/143416 A2 | 10/2012 |
| WO | WO 2012/174487 A2 | 12/2012 |
| WO | WO 2013/024104 A1 | 2/2013 |
| WO | WO 2013/027168 A1 | 2/2013 |
| WO | WO 2013/064900 A1 | 5/2013 |
| WO | WO 2013/082429 A1 | 6/2013 |
| WO | WO 2013/156869 A1 | 10/2013 |
| WO | WO 2013/158952 A1 | 10/2013 |
| WO | WO 2013/184878 A1 | 12/2013 |
| WO | WO 2013/186229 A1 | 12/2013 |
| WO | WO 2014/037340 A1 | 3/2014 |
| WO | WO 2014/043206 A1 | 3/2014 |
| WO | WO 2014/078257 A1 | 5/2014 |
| WO | WO 2014/095775 A1 | 6/2014 |
| WO | WO 2014/128070 A1 | 8/2014 |
| WO | WO 2014/128111 A1 | 8/2014 |
| WO | WO 2014/128655 A1 | 8/2014 |
| WO | WO 2014/134267 A1 | 9/2014 |
| WO | WO 2014/140076 A1 | 9/2014 |
| WO | WO 2014/140077 A1 | 9/2014 |
| WO | WO 2014/152029 A2 | 9/2014 |
| WO | WO 2014/154760 A1 | 10/2014 |
| WO | WO 2014/154762 A1 | 10/2014 |
| WO | WO 2014/159837 A1 | 10/2014 |
| WO | WO 2014/160873 A1 | 10/2014 |
| WO | WO 2014/165143 A1 | 10/2014 |
| WO | WO 2014/170350 A1 | 10/2014 |
| WO | WO 2014/173241 A1 | 10/2014 |
| WO | WO 2014/182929 A1 | 11/2014 |
| WO | WO 2014/191894 A1 | 12/2014 |
| WO | WO 2014/202578 A1 | 12/2014 |
| WO | WO 2015/002754 A2 | 1/2015 |
| WO | WO 2015/004533 A2 | 1/2015 |
| WO | WO 2015/011084 A1 | 1/2015 |
| WO | WO 2015/013635 A2 | 1/2015 |
| WO | WO 2015/015318 A2 | 2/2015 |
| WO | WO 2015/086507 A1 | 6/2015 |
| WO | WO 2016/087936 A1 | 6/2016 |
| WO | WO 2016/087942 A1 | 6/2016 |
| WO | WO 2016/092375 A1 | 6/2016 |
| WO | WO 2016/097863 A1 | 6/2016 |
| WO | WO 2016/097870 A1 | 6/2016 |

OTHER PUBLICATIONS

Schafer et al. Drug Discovery Today, 2008, 13 (21/22), 913-916.*
Aiello, R.J., et al., "Monocyte chemoattractant protein-1 accelerates atherosclerosis in apolipoprotein E-deficient mice" *Arterioscler Thromb. Vasc. Biol.* 19(6): 1518-25 (1999).
Alexandraki, K. et al., "Inflammatory process in type 2 diabetes: The role of cytokines" *Ann N Y Acad Sci*, 2006. 1084:89-117.
Antonelli, A. et al., "Serum levels of proinflammatory cytokines interleukin-1beta, interleukin-6, and tumor necrosis factor alpha in mixed cryoglobulinemia" *Arthritis Rheum*, 2009. 60(12):3841-7.
Aricha, R. et al., "Blocking of IL-6 suppresses experimental autoimmune myasthenia gravis" *J Autoimmun*, 2011. 36(2):135-41.
Arif, M. et al., "Protein lysine acetylation in cellular function and its role in cancer manifestation" *Biochim Biophys Acta*, 2010. 1799(10-12):702-16.
Ash, Z. and P. Emery, "The role of tocilizumab in the management of rheumatoid arthritis" *Expert Opin Biol Ther*, 2012. 12(9): 1277-89.
Bandukwala, H.S. et al., "Selective inhibition of CD4+ T-cell cytokine production and autoimmunity by BET protein and c-Myc inhibitors" *Proc Natl Acad Sci USA*, 2012. 109(36):14532-7.
Bandyopadhyay, K. et al., "Spermidinyl-CoA-based HAT inhibitors block DNA repair and provide cancer-specific chemo- and radiosensitization" *Cell Cycle*, 2009. 8(17):2779-88. (Author's manuscript, 19 pages).
Banerjee, C. et al., "BET bromodomain inhibition as a novel strategy for reactivation of HIV-1" *J Leukoc Biol*, 2012. 92(6):1147-54.
Baron, P. et al., "Production of IL-6 by human myoblasts stimulated with Abeta: relevance in the pathogenesis of IBM" *Neurology*, 2001. 57(9):1561-5.
Bartholomeeusen, K. et al., "BET bromodomain inhibition activates transcription via a transient release of P-TEFb from 7SK snRNP" JBC in Press, 2012. M112.410746, 16 pages. Final publication in: *J Biol Chem*, 287:36609-16.
Bassiouny, D.A. and O. Shaker, "Role of interleukin-17 in the pathogenesis of vitiligo" *Clin Exp Dermatol*, 2011. 36(3):292-7.
Bayraktaroğlu, T. et al., "Serum levels of tumor necrosis factor-alpha, interleukin-6 and interleukin-8 are not increased in dyspeptic patients with Helicobacter pylori-associated gastritis" *Mediators Inflamm*, 2004. 13(1):25-8.
Belanger, D.B. et al., "Discovery of imidazo[1,2-a]pyrazine-based Aurora kinase inhibitors" *Bioorg. Med. Chem. Lett.*, 20:5170-5174 (2010).
Belkina, A.C. and G.V. Denis, "BET domain co-regulators in obesity, inflammation and cancer" *Nat Rev Cancer*, 2012. 12(7):465-77.
Bellan, C. et al., "CDK9/CYCLIN T1 expression during normal lymphoid differentiation and malignant transformation" *J. Pathol.*, 2004. 203(4):946-52.
Belli, F. et al., "Cytokines assay in peripheral blood and bronchoalveolar lavage in the diagnosis and staging of pulmonary granulomatous diseases" *Int J Immunopathol Pharmacol*, 2000. 13(2):61-67.

(56) References Cited

OTHER PUBLICATIONS

Berkovits, B.D. et al., "The testis-specific double bromodomain-containing protein BRDT forms a complex with multiple spliceosome components and is required for mRNA splicing and 3'-UTR truncation in round spermatids" *Nucleic Acids Res*, 2012. 40(15):7162-75.
Besnard, A.G. et al., "Inflammasome-IL-1-Th17 response in allergic lung inflammation" *J Mol Cell Biol*, 2012. 4(1):3-10.
Boring, L. et al., "Decreased lesion formation in CCR2-/-mice reveals a role for chemokines in the initiation of atherosclerosis" *Nature*, 1998. 394(6696):894-7.
Bradley, D.T. and S.E. Kountakis, "Role of interleukins and transforming growth factor-beta in chronic rhinosinusitis and nasal polyposis" *Laryngoscope*, 2005. 115(4):684-6.
Brennan, P., "Isoxazole Inhibitors of Bromodomains" presented at the *RSC Advances in Synthesis and Medicinal Chemistry Conference*, BioPark, Welwyn Garden City, UK, May 1, 2012 (46 pages).
Brodmerkel, C.M. et al., "Discovery and pharmacological characterization of a novel rodent-active CCR2 antagonist, INCB3344" *J Immunol*, 2005. 175(8):5370-8.
Brühl, H. et al., "Dual role of CCR2 during initiation and progression of collagen-induced arthritis: evidence for regulatory activity of CCR2+ T cells" *J Immunol*, 2004. 172(2):890-8.
Chaidos, A. et al., "Inhibition of bromodomain and extraterminal proteins (BET) as a potential therapeutic approach in haematological malignancies: emerging preclinical and clinical evidence" *Ther Adv Hematol*, 6(3):128-141 (2015).
Chemical Abstracts Service, 'Registry' File, RN 1209999-95-0; STN Database [online]. Entry Date: Mar. 15, 2010 (1 page).
Chemical Abstracts Service, 'Registry' File, RN 1348682-08-5; STN Database [online]. Entry Date: Dec. 4, 2011 (1 page).
Chemical Abstracts Service, 'Registry' File, RN 1349387-93-4; STN Database [online]. Entry Date: Dec. 6, 2011 (1 page).
Chen, L. et al., "IL-17RA aptamer-mediated repression of IL-6 inhibits synovium inflammation in a murine model of osteoarthritis" *Osteoarthritis Cartilage*, 2011. 19(6):711-8.
Chevrel, G. et al., "Interleukin-17 increases the effects of IL-1 beta on muscle cells: arguments for the role of T cells in the pathogenesis of myositis" *J Neuroimmunol*, 2003. 137(1-2):125-33.
Chung, C.W. et al., "Bromodomains: a new target class for small molecule drug discovery" *Drug Discovery Today: Therapeutic Strategies* 9(2-3):e111-e120 (2012).
Chung, C.W. et al., "Discovery and characterization of small molecule inhibitors of the BET family bromodomains" *J Med Chem*, 2011. 54(11):3827-38.
Chung, C.W., "Small Molecule Bromodomain Inhibitors: Extending the Druggable Genome" *Progr. Med. Chem*., 51:1-55 (2012).
clinical trials.gov, "A Study to Investigate the Safety, Pharmacokinetics, Pharmacodynamics, and Clinical Activity of GSK525762 in Subjects With NUT Midline Carcinoma (NMC) and Other Cancers" GlaxoSmithKline, Identifier NCT01587703, verified Dec. 2016 [online]. Retrieved from: https://clinicaltrials.gov/ct2/show/NCT01587703, on Dec. 28, 2016 (6 pages).
Costello, J.F. et al., "Cyclin-dependent kinase 6 (CDK6) amplification in human gliomas identified using two-dimensional separation of genomic DNA" *Cancer Res*, 1997. 57(7):1250-4.
D'Auria, L. et al., "Cytokines and bullous pemphigoid" *Eur Cytokine Netw*, 1999. 10(2):123-34.
Dawson, J. et al., "Targeting monocyte chemoattractant protein-1 signalling in disease" *Expert Opin Ther Targets*, 2003. 7(1):35-48.
Dawson, M.A. et al., "Inhibition of BET Recruitment to Chromatin as an Effective Treatment for MLL-fusion Leukaemia" *Nature*, 2011, 478:529-533.
De Falco, G. et al., "Cdk9 regulates neural differentiation and its expression correlates with the differentiation grade of neuroblastoma and PNET tumors" *Cancer Biol Ther*, 2005. 4(3):277-81.
De Lemos, J.A. et al., "Association between plasma levels of monocyte chemoattractant protein-1 and long-term clinical outcomes in patients with acute coronary syndromes" *Circulation*, 2003. 107(5):690-5.

De Paiva, C.S. et al., "IL-17 disrupts corneal barrier following desiccating stress" *Mucosal Immunol*, 2009. 2(3):243-53.
Degoma, E.M. and D.J. Rader, "Novel HDL-directed pharmacotherapeutic strategies" *Nat Rev Cardiol*, 2011. 8(5):266-77.
Delmore, J.E. et al., "BET bromodomain inhibition as a therapeutic strategy to target c-Myc" *Cell*, 2011. 146(6):904-17.
Deng, J. et al., "Th17 and Th1 T-cell responses in giant cell arteritis" *Circulation*, 2010. 121(7):906-15.
Denis, G.V. et al., "An emerging role for bromodomain-containing proteins in chromatin regulation and transcriptional control of adipogenesis" *FEBS Lett*, 2010. 584(15):3260-8. (Author manuscript, 21 pages).
Denis, G.V., "Bromodomain coactivators in cancer, obesity, type 2 diabetes, and inflammation" *Discov Med*, 2010. 10(55):489-99.
Deo, R. et al., "Association among plasma levels of monocyte chemoattractant protein-1, traditional cardiovascular risk factors, and subclinical atherosclerosis" *J Am Coll Cardiol*, 2004. 44(9): p. 1812-8.
Dias, P.M. and G. Banerjee, "The Role of Th17/IL-17 on Eosinophilic Inflammation" *J Autoimmun*, 2012. Article in Press: http://dx.doi.org/10.1016/j.jaut.2012.07.004, 12 pages.
Elliott, D.A. et al., "Apolipoproteins in the brain: implications for neurological and psychiatric disorders" *Clin Lipidol*, 2010. 51(4):555-573. (Author manuscript, 28 pages).
El-Osta, H.E. and R. Kurzrock, "Castleman's disease: from basic mechanisms to molecular therapeutics" *Oncologist*, 2011. 16(4):497-511.
European Patent Application No. 14820520.6, by Zenith Epigenetics Corp.: Extended European Search Report, including Search Opinion, dated Feb. 8, 2017 (9 pages).
European Patent Application No. 14822480.1, by Zenith Epigenetics Corp.: Extended European Search Report, including Search Opinion, dated Jan. 4, 2017 (10 pages).
European Patent Application No. 14822511.3, by Zenith Epigenetics Corp.: Extended European Search Report, including Search Opinion, dated Jan. 2, 2017 (7 pages).
European Patent Application No. 14832298.5, by Zenith Epigenetics Corp.: Extended European Search Report, including Search Opinion, dated Nov. 11, 2016 (6 pages).
European Patent No. EP 0 385 850 A2: Machine English translation; retrieved from ProQuest Dialog, on Aug. 15, 2016; 68 pages.
European Patent No. EP 0 556 789 A2: Machine English translation; retrieved from ProQuest Dialog, on Aug. 15, 2016; 59 pages.
Feng, Q. et al., "An epigenomic approach to therapy for tamoxifen-resistant breast cancer" *Cell Research*, 24:809-819 (2014).
Fife, B.T. et al., "CC chemokine receptor 2 is critical for induction of experimental autoimmune encephalomyelitis" *J Exp Med*, 192(6):899-905 (2000).
Figueroa-Vega, N. et al., "Increased circulating pro-inflammatory cytokines and Th17 lymphocytes in Hashimoto's thyroiditis" *J Clin Endocrinol Metab*, 95(2):953-62 (2010).
Filippakopoulos, P. and S. Knapp, "Targeting bromodomains: epigenetic readers of lysine acetylation" *Nature Reviews*, 13:337-356 (2014).
Filippakopoulos, P. et al., "Selective Inhibition of BET Bromodomains" *Nature*, 68:1067-1073 (2010).
Freireich, E.J. et al., "Quantitative comparison of toxicity of anti-cancer agents in mouse, rat, hamster, dog, monkey, and man" *Cancer Chemother Rep*, 50(4):219-244 (1966).
French, C.A., "NUT midline carcinoma" *Cancer Genet Cytogenet*, 2010. 203(1):16-20. (Author manuscript, 9 pages).
Fujioka, A. et al., "The analysis of mRNA expression of cytokines from skin lesions in Churg-Strauss syndrome" *J Dermatol*, 1998. 25(3):171-7.
Fujishima, S. et al., "Involvement of IL-17F via the induction of IL-6 in psoriasis" *Arch Dermatol Res*, 2010. 302(7):499-505.
Gagnon, D. et al., "Proteasomal degradation of the papillomavirus E2 protein is inhibited by overexpression of bromodomain-containing protein 4" *J Virol*, 2009. 83(9):4127-39.
Gaucher, J. et al., "Bromodomain-dependent stage-specific male genome programming by Brdt" *EMBO J*, 2012. 31(19):3809-20.

(56) References Cited

OTHER PUBLICATIONS

Gloddek, B. et al., "Pharmacological influence on inner ear endothelial cells in relation to the pathogenesis of sensorineural hearing loss" *Adv Otorhinolaryngol*, 2002. 59:75-83.
Gong, J-H. et al., "An antagonist of monocyte chemoattractant protein 1 (MCP-1) inhibits arthritis in the MRL-Ipr mouse model" *J Exp Med*, 1997. 186(1):131-7.
Gong, J-H. et al., "Post-onset inhibition of murine arthritis using combined chemokine antagonist therapy" *Rheumatology*, 2004. 43(1):39-42.
González-Serrano, M.E. et al., "Increased Pro-inflammatory Cytokine Production After Lipopolysaccharide Stimulation in Patients with X-linked Agammaglobulinemia" *J Clin Immunol*, 2012. 32(5):967-74.
Gosling, J. et al., "MCP-1 deficiency reduces susceptibility to atherosclerosis in mice that overexpress human apolipoprotein B" *J Clin Invest*, 1999. 103(6):773-8.
Gottschalk, S. et al., "An Epstein-Barr virus deletion mutant associated with fatal lymphoproliferative disease unresponsive to therapy with virus-specific CTLs" *Blood*, 2001. 97:835-843.
Graber, J.J. et al., "Interleukin-17 in transverse myelitis and multiple sclerosis" *J Neuroimmunol*, 2008. 196(1-2):124-32.
Greenwald, R.J. et al., "E mµ-BRD2 transgenic mice develop B-cell lymphoma and leukemia" *Blood*, 2004. 103(4):1475-84.
Grunwald, C. et al., "Expression of multiple epigenetically regulated cancer/germline genes in nonsmall cell lung cancer" *Int J Cancer*, 2006. 118(10):2522-8.
Gu, L. et al., "Absence of monocyte chemoattractant protein-1 reduces atherosclerosis in low density lipoprotein receptor-deficient mice" *Mol Cell*, 1998. 2(2):275-81.
Gu, Y. et al., "Interleukin (IL)-17 promotes macrophages to produce IL-8, IL-6 and tumour necrosis factor-alpha in aplastic anaemia" *Br J Haematol*, 2008. 142(1):109-14.
Hankovszky, H.O. et al., "Synthesis and reaction of ortho-fluoronitroaryl nitroxides. Novel versatile synthons and reagents for spin-labelling studies" *Can J Chem*, 67:1392-1400 (1989).
Harada, K. et al., "Periductal interleukin-17 production in association with biliary innate immunity contributes to the pathogenesis of cholangiopathy in primary biliary cirrhosis" *Clin Exp Immunol*, 2009. 157(2):261-70.
Haruta, H. et al., "Blockade of interleukin-6 signaling suppresses not only TH17 but also interphotoreceptor retinoid binding protein-specific Th1 by promoting regulatory T cells in experimental autoimmune uveoretinitis" *Invest Ophthalmol Vis Sci*, 2011. 52(6):3264-71.
Hay et al., "The design and synthesis of 5- and 6-isoxazolylbenzimidazoles as selective inhibitors of the BET bromodomains" *Med. Chem. Commun.* 4:140-144 (2013).
Hay, D.A. et al., "Discovery and Optimization of Small-Molecule Ligands for the CBP/p300 Bromodomains" *J. Am. Chem. Soc.* 136:9308-9319 (2014).
He, A. and J.J.L. Miranda, "JQ1 reduces Epstein-Barr virus-associated lymphoproliferative disease in mice without sustained oncogene repression" *Leukemia & Lymphoma*, 2017. DOI: 10.1080/10428194.2017.1372578 [online]. Retrieved Oct. 31, 2017 (5 pages).
Hewings et al., "3,5-Dimethylisoxazoles Act as Acetyl-lysine-mimetic Bromodomain Ligands" *J. Med. Chem.* 54:6761-6770 (2011).
Hewings et al., "3,5-Dimethylisoxazoles inhibit the bromodomain-histone protein-protein interaction" *243rd National Spring Meeting of the American-Chemical-Society* (*Symposium on Ionic Liquids—Science and Applications*), San Diego, CA. General Poster Session, Mar. 28, 2012, Poster 326 Abstract [online]. Retrieved from: http://acselb-529643017.us-west-2.elb.amazonaws.com/chem/243nm/program/view.php?pub_num=326&par=MEDI.
Hewings et al., "Optimization of 3,5-Dimethylisoxazole Derivatives as Potent Bromodomain Ligands" *J. Med. Chem.* 56:3217-3227 (2013).

Hewings et al., "Progress in the development and application of small molecule inhibitors of bromodomain-acetyl-lysine interactions" *J. Med. Chem.* 55:9393-9413 (2012).
Hohki, S. et al., "Blockade of interleukin-6 signaling suppresses experimental autoimmune uveoretinitis by the inhibition of inflammatory Th17 responses" *Exp Eye Res*, 2010. 91(2):162-70.
Hölttä, V. et al., "IL-23/IL-17 immunity as a hallmark of Crohn's disease" *Inflamm Bowel Dis*, 2008. 14(9):1175-84.
Hoshino, I. and H. Matsubara, "Recent advances in histone deacetylase targeted cancer therapy" *Surg Today*, 2010. 40(9):809-15.
Huang, D. et al., "Absence of monocyte chemoattractant protein 1 in mice leads to decreased local macrophage recruitment and antigen-specific T helper cell type 1 immune response in experimental autoimmune encephalomyelitis" *J Exp Med*, 2001. 193(6):713-26.
Içöz, S. et al., "Enhanced IL-6 production in aquaporin-4 antibody positive neuromyelitis optica patients" *Int J Neurosci*, 2010. 120(1):71-5.
International Search Report and Written Opinion issued in International Application No. PCT/IB2014/002238; dated Apr. 23, 2015.
International Search Report and Written Opinion issued in International Application No. PCT/IB2014/002240; dated Mar. 10, 2015.
International Search Report and Written Opinion issued in International Application No. PCT/IB2015/002479; dated Apr. 21, 2016.
International Search Report and Written Opinion issued in International Application No. PCT/IB2015/002490; dated Apr. 1, 2016.
International Search Report and Written Opinion issued in International Application No. PCT/IB2015/002522; dated Apr. 13, 2016.
International Search Report and Written Opinion issued in International Application No. PCT/IB2016/001874; dated Apr. 25, 2016.
International Search Report and Written Opinion issued in International Application No. PCT/US2014/043423; dated Jan. 12, 2005.
Ishizu, T. et al., "CSF cytokine and chemokine profiles in acute disseminated encephalomyelitis" *J Neuroimmunol*, 2006. 175(1-2):52-58.
Ito, Y. et al., "Pathogenic significance of interleukin-6 in a patient with antiglomerular basement membrane antibody-induced glomerulonephritis with multinucleated giant cells" *Am J Kidney Dis*, 1995. 26(1):72-9.
Jadidi-Niaragh, F. and A. Mirshafiey, "Th17 cell, the new player of neuroinflammatory process in multiple sclerosis" *Scand J Immunol*, 2011. 74(1):1-13.
Jahagirdar, R. et al., "An Orally Bioavailable Small Molecule RVX-297 Significantly Decreases Disease in a Mouse Model of Multiple Sclerosis" (Poster Presentation). World Congress of Inflammation, Paris, France, 2011, 1 page.
Jen, H-Y. et al., "Increased serum interleukin-17 and peripheral Th17 cells in children with acute Henoch-Schonlein purpura" *Pediatr Allergy Immunol*, 2011. 22(8):862-8.
Jia, S., et al., "The T helper type 17/regulatory T cell imbalance in patients with acute Kawasaki disease" *Clin Exp Immunol*, 2010. 162(1):131-7.
Johnson, R.B. et al., "Interleukin-11 and IL-17 and the pathogenesis of periodontal disease" *J Periodontol*, 2004. 75(1):37-43.
Kahawita, I.P. and D.N. Lockwood, "Towards understanding the pathology of erythema nodosum leprosum" *Trans R Soc Trop Med Hyg*, 2008. 102(4):329-37.
Kallen, K.J. et al., "New developments in IL-6 dependent biology and therapy: where do we stand and what are the options?" *Expert Opin Investig Drugs*, 1999. 8(9):1327-49.
Kaplanski, G. et al., "Jarisch-Herxheimer reaction complicating the treatment of chronic Q fever endocarditis: elevated TNFalpha and IL-6 serum levels" *J Infect*, 1998. 37(1):83-4.
Kappel, L.W. et al., "IL-17 contributes to CD4-mediated graft-versus-host disease" *Blood*, 2009. 113(4):945-52.
Katsifis, G.E. et al., "Systemic and local interleukin-17 and linked cytokines associated with Sjogren's syndrome immunopathogenesis" *Am J Pathol*, 2009. 175(3):1167-77.
Kawai, M. et al., "Sustained response to tocilizumab, anti-interleukin-6 receptor antibody, in two patients with refractory relapsing polychondritis" *Rheumatology*, 2009. 48(3):318-9.
Kawakami, T. et al., "Reduction of interleukin-6, interleukin-8, and anti-phosphatidylserine-prothrombin complex antibody by granu-

(56) References Cited

OTHER PUBLICATIONS locyte and monocyte adsorption apheresis in a patient with pyoderma gangrenosum and ulcerative colitis" *Am J Gastroenterol*, 2009. 104(9):2363-4.

Kawakami, T. et al., "Serum levels of interleukin-6 in patients with cutaneous polyarteritis nodosa" *Acta Derm Venereol*, 2012. 92(3):322-3.

Kelly, P.N. and A. Strasser, "The role of Bcl-2 and its pro-survival relatives in tumourigenesis and cancer therapy" *Cell Death Differ*, 2011. 18(9):1414-24.

Kim, S.E. et al., "Increased serum interleukin-17 in Graves' ophthalmopathy" *Graefes Arch Clin Exp Ophthalmol*, 2012. 250(10):1521-6.

Kimura, A. and T. Kishimoto, "IL-6: regulator of Treg/Th17 balance" *Eur J Immunol*, 2010. 40(7):1830-5.

Koch, A.E. et al., "Enhanced production of monocyte chemoattractant protein-1 in rheumatoid arthritis" *J Clin Invest*, 1992. 90(3):772-9.

Kyburz, D. and M. Corr, "Th17 cells generated in the absence of TGF-beta induce experimental allergic encephalitis upon adoptive transfer" *Expert Rev Clin Immunol*, 2011. 7(3):283-5.

Lahdenperä, A.I. et al., "Up-regulation of small intestinal interleukin-17 immunity in untreated coeliac disease but not in potential coeliac disease or in type 1 diabetes" *Clin Exp Immunol*, 2012. 167(2):226-34.

Lamale, L.M. et al., "Interleukin-6, histamine, and methylhistamine as diagnostic markers for interstitial cystitis" *Urology*, 2006. 68(4):702-6.

Lamotte, Y. et al., "Identification of a novel series of BET family Bromodomain inhibitors: binding mode and profile of I-BET151 (GSK1210151A)" Bioorganic & Medicinal Chemistry Letters, 2012. Accepted manuscript, doi: 10.1016/j.bmcl.2012.02.041. Final publication as: Seal, J. et al., "Identification of a novel series of BET family bromodomain inhibitors: binding mode and profile of I-BET151 (GSK1210151A)" *Bioorg Med Chem Lett*, 2012. 22(8):2968-72.

Latifi, S.Q. et al., "Persistent elevation of serum interleukin-6 in intraabdominal sepsis identifies those with prolonged length of stay" *J Pediatr Surg*, 2004. 39(10):1548-52.

Lee, D.K. et al., "Androgen receptor interacts with the positive elongation factor P-TEFb and enhances the efficiency of transcriptional elongation" *J Biol Chem*, 2001. 276(13):9978-84.

Li, Z., et al., "The BET bromodomain inhibitor JQ1 activates HIV latency through antagonizing Brd4 inhibition of Tat-transactivation" *Nucleic Acids Res Advance Access*, 2012. DOI:10.1093/nar/gks976, 11 pages.

Lin, F.J. et al., "Imbalance of regulatory T cells to Th17 cells in IgA nephropathy" *Scand J Clin Lab Invest*, 2012. 72(3):221-9.

Linhares, U.C. et al., "The Ex Vivo Production of IL-6 and IL-21 by CD4(+) T Cells is Directly Associated with Neurological Disability in Neuromyelitis Optica Patients" *J Clin Immunol*, 2012, DOI 10.1007/s10875-012-9780-2, 11 pages.

Lopez-Robles, E. et al., "TNFalpha and IL-6 are mediators in the blistering process of pemphigus" *Int J Dermatol*, 2001. 40(3):185-8.

Lu, M.O. and J. Zhu, "The role of cytokines in Guillain-Barre syndrome" *J Neurol*, 2011. 258(4):533-48.

Ma, D. et al., "Profile of Th17 cytokines (IL-17, TGF-beta, IL-6) and Th1 cytokine (IFN-gamma) in patients with immune thrombocytopenic purpura" *Ann Hematol*, 2008. 87(11):899-904.

Mahad, D.J. and R.M. Ransohoff, "The role of MCP-1 (CCL2) and CCR2 in multiple sclerosis and experimental autoimmune encephalomyelitis (EAE)" *Semin Immunol*, 2003. 15(1):23-32.

Matzuk, M.M. et al., "Small-Molecule Inhibition of BRDT for Male Contraception" *Cell*, 2012. 150(4):673-684, with supplemental pp. S1-S8.

McLaughlin-Drubin, M.E. and K. Munger, "Viruses Associated with Human Cancer" *Biochim Biophys Acta*, 2008. 1782(3):127-150. NIH Public Access Author Manuscript; available in PMC Mar. 1, 2009 (50 pages).

McKinley, L. et al., "TH17 cells mediate steroid-resistant airway inflammation and airway hyperresponsiveness in mice" *J Immunol*, 2008. 181(6):4089-97.

McMahon, G. "VEGF Receptor Signaling in Tumor Angiogenesis" *The Oncologist*, 5(Suppl 1):3-10 (2000).

Mendrzyk, F. et al., "Genomic and protein expression profiling identifies CDK6 as novel independent prognostic marker in medulloblastoma" *J Clin Oncol*, 2005. 23(34):8853-62.

Mertz, J.A., "Targeting MYC Dependence in Cancer by Inhibiting BET Bromodomains", *PNAS*, 108(40):16669-16674 (2011).

Min, C.K. et al., "Cutaneous leucoclastic vasculitis (LV) following bortezomib therapy in a myeloma patient; association with pro-inflammatory cytokines" *Eur J Haematol*, 2006. 76(3):265-8.

Mirguet, O. et al., "From ApoA1 upregulation to BET family bromodomain inhibition: discovery of I-BET151" *Bioorg Med Chem Lett*, Article in Press, 2012. doi: 10.1016/j.bmcl.2012.01.125, 5 pages. Final publication in vol. 22, No. 8, pp. 2963-2967.

Mitsuyama, K. et al., "STAT3 activation via interleukin 6 trans-signalling contributes to ileitis in SAMP1/Yit mice" *Gut*, 2006. 55(9):1263-9.

Miyazaki, et al. "Intravenous Injection of Rabbit Apolipoprotein A-I Inhibits the Progression of Atherosclerosis in Cholesterol-Fed Rabbits" *Arterioscler. Thromb. Vasc. Biol.* 15: 1882-1888 (1995).

Mok, M.Y. et al., "The relation of interleukin 17 (IL-17) and IL-23 to Th1/Th2 cytokines and disease activity in systemic lupus erythematosus" *J Rheumatol*, 2010. 37(10):2046-52.

Morin, R.D. et al., "Frequent mutation of histone-modifying genes in non-Hodgkin lymphoma" *Nature*, 2011. 476(7360):298-303. (Author manuscript, 17 pages.).

Mudter, J. and M.F. Neurath, "IL-6 signaling in inflammatory bowel disease: pathophysiological role and clinical relevance" *Inflamm Bowel Dis*, 2007. 13(8):1016-23.

Muller Kobold, A.C. et al., "In vitro up-regulation of E-selectin and induction of interleukin-6 in endothelial cells by autoantibodies in Wegener's granulomatosis and microscopic polyangiitis" *Clin Exp Rheumatol*, 1999. 17(4):433-40.

Muller, S. et al., "Bromodomains as therapeutic targets" *Expert Rev Mol Med*, 2011. 13: e29, 21 pages.

Nakahama, H. et al., "Distinct responses of interleukin-6 and other laboratory parameters to treatment in a patient with Wegener's granulomatosis" *Intern Med*, 1993. 32(2):189-92.

Nelken, N.A. et al., "Monocyte chemoattractant protein-1 in human atheromatous plaques" *J Clin Invest*, 1991. 88(4):1121-7.

Ni, J. et al., "Involvement of Interleukin-17A in Pancreatic Damage in Rat Experimental Acute Necrotizing Pancreatitis" *Inflammation*, 2012. [online] DOI: 10.1007/s10753-012-9519-5, published Sep. 19, 2012 (13 pages).

Niu, J. and P.E. Kolattukudy, "Role of MCP-1 in cardiovascular disease: molecular mechanisms and clinical implications" *Clin Sci*, 2009. 117(3):95-109.

Ooi, J.D. et al, "Review: T helper 17 cells: their role in glomerulonephritis" *Nephrology*, 2010. 15(5):513-21.

Ortiz-Lucas, M. et al., "Irritable bowel syndrome immune hypothesis. Part two: the role of cytokines" *Rev Esp Enferm Dig*, 2010. 102(12):711-7.

Ott, C.J. et al., "BET bromodomain inhibition targets both c-Myc and IL7R in high-risk acute lymphoblastic leukemia" *Blood*, 2012. 120(14):2843-52.

Pakrashi, S.C. "4-Quinazolinones. II. Self-condensation of anthranilamide" *J Org Chem*, 36(5):642-645 (1971).

Palermo, R.D. et al., "RNA polymerase II stalling promotes nucleosome occlusion and pTEFb recruitment to drive immortalization by Epstein-Barr virus." *PLoS Pathog*, 2011. 7(10): e1002334, 15 pages.

Paquet, P. and G.E. Pierard, "Interleukin-6 and the skin" *Int Arch Allergy Immunol*, 1996. 109(4):308-17.

Patton, J.T. et al., "Silvestrol Modulates Direct Anti-Tumor Activity Against Epstein-Barr Virus (EBV)-Associated Lymphomas While Sparing Innate and Antigen Specific Adaptive Immunity" *Blood*, 2011. 118:Abstract 104 (2 pages).

Peserico, A. and C. Simone, "Physical and functional HAT/HDAC interplay regulates protein acetylation balance" *J Biomed Biotechnol*, 2011. 371832, 10 pages.

(56) References Cited

OTHER PUBLICATIONS

Pinedo, H.M. and D.J. Slamon, "Translational Research: The Role of VEGF in Tumor Angiogenesis" *The Oncologist*, 5(Suppl. 1):1-2 (2000).
Poreba, E. et al., "Epigenetic mechanisms in virus-induced tumorigenesis" *Clin Epigenetics*, 2011. 2(2):233-47.
Prabakaran, K. et al., "Iridium bromide catalysed, ultrasound-assisted, region-selective synthesis of ethyl-5-(trifluoromethyl)-1-(3-substituted-isoquinolin-I-yl)-1H-pyrazole-4-carboxylates", *Res. Chem. Intermed.*, 38:429-441 (2012).
Prinjha, R.K. et al., "Place your BETs: the therapeutic potential of bromodomains" *Trends Pharmacol Sci*, 2012. 33(3):146-53.
Radstake, T.R. et al., "The pronounced Th17 profile in systemic sclerosis (SSc) together with intracellular expression of TGFbeta and IFNgamma distinguishes SSc phenotypes" *PLoS One*, 2009. 4(6):e5903. 9 pages.
Ramsay, R.G. and T.J. Gonda, "MYB function in normal and cancer cells" *Nat Rev Cancer*, 2008. 8(7):523-34.
Raychaudhuri, S.P. et al., "IL-17 receptor and its functional significance in psoriatic arthritis" *Mol Cell Biochem*, 2012. 359(1-2):419-29.
Rhodus, N.L. et al., "Proinflammatory cytokine levels in saliva before and after treatment of (erosive) oral lichen planus with dexamethasone" *Oral Dis*, 2006. 12(2):112-6.
Rodriguez, R.M. et al., "Aberrant epigenetic regulation of bromodomain BRD4 in human colon cancer" *J Mol Med*, 2012. 90(5):587-95.
Roger, V.L. et al., "Heart disease and stroke statistics—2012 update: a report from the American Heart Association" *Circulation*, 2012. 125(1):3-e220.
Ruden, M. and N. Puri, "Novel anticancer therapeutics targeting telomerase" *Cancer Treat Rev*, 2012. Article in Press: http://dx.doi.org/10.1016/j.ctrv.2012.06.007, 13 pages.
Rudloff, U. and Y. Samuels, "TYRO3-mediated regulation of MITF: a novel target in melanoma?" *Pigment Cell Melanoma Res*, 2010. 23(1):9-11.
Sanchez, R. and M.M. Zhou, "The role of human bromodomains in chromatin biology and gene transcription" *Curr Opin Drug Discov Devel*, 2009. 12(5):659-65. (Author manuscript, 12 pages.).
Scanlan, M.J. et al., "Expression of cancer-testis antigens in lung cancer: definition of bromodomain testis-specific gene (BRDT) as a new CT gene, CT9" *Cancer Lett*, 2000. 150(2):155-64.
Seal, J. et al., "Identification of a novel series of BET family bromodomain inhibitors: Binding mode and profile of I-BET15I(GSK121051A)" *Bioorg. Med. Chem. Lett.*, 22:2968-2972 (2012).
Segura, M.F. et al., "BRD4 is a novel therapeutic target in melanoma" Poster Presentation, AACR 103rd Annual Meeting, Mar. 31-Apr. 4, 2012 in Chicago, IL. *Cancer Research*, 2012. 72(8), Supplement 1, Abstract 2185.
Shang, E. et al., "The first bromodomain of Brdt, a testis-specific member of the BET sub-family of double-bromodomain-containing proteins, is essential for male germ cell differentiation" *Development*, 2007. 134(19):3507-15.
Shibuya, M. et al., "Successful treatment with tocilizumab in a case of Cogan's syndrome complicated with aortitis" *Mod Rheumatol*, 2012, online: DOI 10.1007/s10165-012-0691-0, 5 pages.
Simmons, E.M. et al., "Plasma cytokine levels predict mortality in patients with acute renal failure" *Kidney Int*, 2004. 65(4):1357-65.
Simone, C. and A. Giordano, "Abrogation of signal-dependent activation of the cdk9/cyclin T2a complex in human RD rhabdomyosarcoma cells" *Cell Death Differ*, 2007. 14(1):192-5.
Soltesz, P. et al., "Immunological features of primary anti-phospholipid syndrome in connection with endothelial dysfunction" *Rheumatology*, 2008. 47(11):1628-34.
Stenman, G. et al., "New tricks from an old oncogene: gene fusion and copy number alterations of MYB in human cancer" *Cell Cycle*, 2010. 9(15):2986-95.
Sun, Y. et al., "MMP-9 and IL-6 are potential biomarkers for disease activity in Takayasu's arteritis" *Int J Cardiol*, 2012. 156(2):236-8.

Tang, X. et al., "Assessment of Brd4 inhibition in idiopathic pulmonary fibrosis lung fibroblasts and in vivo models of lung fibrosis" *Am. J. Pathol.*, 183(2):470-479 (2013).
Taylan, A. et al., "Evaluation of the T helper 17 axis in ankylosing spondylitis" *Rheumatol Int*, 2012. 32(8):2511-5.
Tong, W.G. et al., "Phase I and pharmacologic study of SNS-032, a potent and selective Cdk2, 7, and 9 inhibitor, in patients with advanced chronic lymphocytic leukemia and multiple myeloma" *J Clin Oncol*, 2010. 28(18):3015-22.
Traves, S.L. and L.E. Donnelly, "Th17 cells in airway diseases" *Curr. Mol. Med.*, 2008. 8(5):416-26.
Uchida, T. et al., "Antitumor effect of bcl-2 antisense phosphorothioate oligodeoxynucleotides on human renal-cell carcinoma cells in vitro and in mice" *Mol Urol*, 2001. 5(2):71-8.
Urano, W. et al., "The inflammatory process in the mechanism of decreased serum uric acid concentrations during acute gouty arthritis" *J Rheumatol*, 2002. 29(9):1950-3.
Utsunomiya, I. et al., "Preparation of Alkyl-Substituted Indoles in the Benzene Portion. Part 13. Enantiospecific Synthesis of Mitosene Analogues Related to FFR 900482 and FR 66979" *Chem Pharm Bull*, 43(1):37-48.
Velisek, L. et al., "GABAergic neuron deficit as an idiopathic generalized epilepsy mechanism: the role of BRD2 haploinsufficiency in juvenile myoclonic epilepsy" *PLoS One*, 2011. 6(8):e23656, 8 pages.
Vernarecci, S. et al., "Tuning acetylated chromatin with HAT inhibitors: a novel tool for therapy" *Epigenetics*, 2010. 5(2): p. 105-11.
Vippagunta, S.R. et al., "Crystalline solids" *Adv Drug Del Rev*, 2001. 48:3-26.
Vita, M. and M. Henriksson, "The Myc oncoprotein as a therapeutic target for human cancer" *Semin Cancer Biol*, 2006. 16(4):318-30.
Wang, F. et al., "Brd2 disruption in mice causes severe obesity without Type 2 diabetes" *Biochem J*, 2010. 425(1): p. 71-83, with supplemental online material, 2 pages.
Wang, G. et al., "Increased cyclin-dependent kinase 6 expression in bladder cancer" *Oncol Lett*, 2012. 4(1): p. 43-46.
Wang, S. and P.M. Fischer, "Cyclin-dependent kinase 9: a key transcriptional regulator and potential drug target in oncology, virology and cardiology" *Trends Pharmacol Sci*, 2008. 29(6):302-13.
Watson, J.D., "Curing 'incurable' cancer" *Cancer Discov*, 2011. 1(6):477-80.
Whelligan, D.K. et al. "Aminopyrazine inhibitors binding to an unusual inactive conformation of the mitotic kinase Nek2: SAR and structural characterization" *J Med Chem*, 53(21):7682-7698 (2010).
Wu, S.Y. and C.M. Chiang, "The double bromodomain-containing chromatin adaptor Brd4 and transcriptional regulation" *J Biol Chem*, 2007. 282(18):13141-5.
Xu, L. et al., "Critical role of Th17 cells in development of autoimmune hemolytic anemia" *Exp Hematol*, 2012. Article in Press: http://dx.doi.org/10.1016/j.exphem.2012.08.008, 15 pages.
Yamaguchi, M. et al., "Novel Antiasthmatic Agents with Dual Activities of Thromboxane $A_2$ Synthetase Inhibition and Bronchodilation. 1. 2-[2-(1-Imidazolyl)alkyl]-1(2H)-phthalazinones" *J. Med. Chem.*, 36:4052-4060 (1993).
Yamashita, T. et al., "IL-6-mediated Th17 differentiation through RORγt is essential for the initiation of experimental autoimmune myocarditis" *Cardiovasc Res*, 2011. 91(4):640-8.
Yoshii, T. et al., "Local levels of interleukin-1beta, -4, -6 and tumor necrosis factor alpha in an experimental model of murine osteomyelitis due to Staphylococcus aureus" *Cytokine*, 2002. 19(2):59-65.
Yoshimura, T. et al., "Involvement of Th17 cells and the effect of anti-IL-6 therapy in autoimmune uveitis" *Rheumatology*, 48(4):347-354 (2009).
You, J. et al., "Kaposi's sarcoma-associated herpesvirus latency-associated nuclear antigen interacts with bromodomain protein Brd4 on host mitotic chromosomes" *J Virol*, 2006. 80(18):8909-19.
Yu et al., "Toll-Like Receptor 7 Agonists: Chemical Feature Based Pharmacophore Identification and Molecular Docking Studies" *PLoS ONE* 8(3):e56514, doi:10.1371/journal.pone.0056514 (2013).
Zhang, G. et al., "Down-regulation of NF-kappaB Transcriptional Activity in HIVassociated Kidney Disease by BRD4 Inhibition"

(56) References Cited

OTHER PUBLICATIONS

*JBC Papers in Press*, 2012. M112.359505 with supplement, 38 pages. Final publication in: *J Biol Chem*, 287(34):28840-51.

Zhang, W.S. et al., "Bromodomain-Containing-Protein 4 (BRD4) Regulates RNA Polymerase II Serine 2 Phosphorylation in Human CD4+ T Cells" JBC Papers in Press, 2012. M112.413047, 30 pages. Final publication in: *J Biol Chem*, 287:43137-55.

Zhao, L. et al., "Interleukin-17 contributes to the pathogenesis of autoimmune hepatitis through inducing hepatic interleukin-6 expression" *PLoS One*, 2011. 6(4):e18909, 8 pages.

Zhou, M. et al., "Bromodomain protein Brd4 regulates human immunodeficiency virus transcription through phosphorylation of CDK9 at threonine 29" *J Virol*, 2009. 83(2):1036-44.

Zhu, J. et al., "Reactivation of Latent HIV-1 by Inhibition of BRD4" *Cell Rep*, 2012. 2:1-10, with supplemental pp. S1-S7.

Zuber, J. et al., "RNAi screen identifies Brd4 as a therapeutic target in acute myeloid leukaemia" *Nature*, 2011. 478(7370):524-8.

Bernstein, J. (2002) Polymorphism in Molecular Crystals. Oxford: Clarendon Press; pp. 115-118,272.

Braga, D. et al. (2005) "Making crystals from crystals: a green route to crystal engineering and polymorphism" J Royal Soc Chem Commun, 2005:3635-3645.

Davidovich, M. et al. (2004) "Detection of Polymorphism by Powder X-Ray Diffraction: Interference by Preferred Orientation" Am Pharm Rev, 7(1):10,12,14,16,100.

Dean, J.A. (1995) Analytical Chemistry Handbook. McGraw-Hill, Inc.; pp. 10.24-10.26.

Dikov, A. et al. (1996) "New fluorogenic substrates in histochemistry of peptidases. II. Histochemical demonstration of dipeptidyl peptidase IV" Comptes rendus de l'Acacémie bulgare des Sciences, 49(6):99-102.

Grant, D.J.W., "Theory and Origin of Polymorphism" in Polymorphism in Pharmaceutical Solids. Brittain, Harry G. (Ed.) New York, NY: Marcel Dekker, Inc., 1999; pp. 1-2.

Guillory, J.K. "Generation of Polymorphs, Hydrates, Solvates, and Amorphous Solids" in Polymorphism in Pharmaceutical Solids. Brittain, Harry G. (Ed.) New York, NY: Marcel Dekker, Inc., 1999; pp. 183-226.

Ivanisevic, I. et al. (2010) "Uses of X-Ray Powder Diffraction in the Pharmaceutical Industry" in Pharmaceutical Sciences Encyclopedia: Drug Discovery, Development, and Manufacturing. Gad, Shayne C. (Ed.) John Wiley & Sons, Inc.: pp. 1-42.

Jain, N.K. et al. (1986) "Polymorphism in Pharmacy" Indian Drugs, 23(6):315-329.

Jordan, V.C. (2003) "Tamoxifen: a most unlikely pioneering medicine" Nat Rev Drug Disc, 2:205-213.

Kirk-Othmer Encyclopedia of Chemical Technology, 8, 2002, pp. 95-147.

Liu et al. (2014) HCAPLUS database, Accession No. 2014:1037890, Columbus, Ohio: STN International, Retrieved Mar. 5, 2018 (2 pages).

Morris, K.R. "Structural Aspects of Hydrates and Solvates" in Polymorphism in Pharmaceutical Solids. Brittain, Harry G. (Ed.) New York, NY: Marcel Dekker. Inc., 1999, pp. 125-181.

Seddon, K.R. (2004) "Pseudopolymorph: A Polemic" Crystal Growth & Design, 4(6):1087; doi: 10.1021/cg030084yS1528-7483(03)00084-6 [online]. Retrieved from: http://pubs.acs.org, on Nov. 6, 2006 (2 pages).

Ulrich, J. "Crystallization" in Kirk-Othmer Encyclopedia of Chemical Technolooy. John Wiley & Sons, Inc., vol. 8, pp. 95-147 (2002).

Yu, L. et al. (1998) "Physical characterization of polymorphic drugs: an integrated characterization strategy" PSTT, 1(3):118-127.

\* cited by examiner

SUBSTITUTED BICYCLIC COMPOUNDS AS BROMODOMAIN INHIBITORS

CROSS-REFERENCE TO RELATED PATENT APPLICATIONS

This application is a divisional of U.S. application Ser. No. 14/900,138, filed Dec. 18, 2015, now U.S. Pat. No. 9,636,328, which is a U.S. national stage of International Patent Application No. PCT/IB2014/002240, filed Jun. 20, 2014, which claims the benefit of priority to U.S. Provisional Application No. 61/837,830, filed Jun. 21, 2013, and U.S. Provisional Application No. 61/911,668, filed Dec. 4, 2013, each of which are hereby incorporated by reference in their entirety.

This application claims priority from U.S. Provisional Patent Application No. 61/837,830, filed Jun. 21, 2013, and U.S. Provisional Patent Application No. 61/911,668, filed Dec. 4, 2013, both which are hereby incorporated by reference in their entirety.

The invention provides novel compounds, pharmaceutical compositions containing such compounds, and their use in prevention and treatment of diseases and conditions associated with bromodomain and extra terminal domain (BET) proteins. Post-translational modifications (PTMs) of histones are involved in regulation of gene expression and chromatin organization in eukaryotic cells. Histone acetylation at specific lysine residues is a PTM that is regulated by histone acetylases (HATs) and deacetylases (HDACs). Peserico, A. and C. Simone, "Physical and functional HAT/HDAC interplay regulates protein acetylation balance," *J Biomed Biotechnol,* 2011:371832 (2011). Small molecule inhibitors of HDACs and HATs are being investigated as cancer therapy. Hoshino, I. and H. Matsubara, "Recent advances in histone deacetylase targeted cancer therapy" *Surg Today* 40(9):809-15 (2010); Vernarecci, S., F. Tosi, and P. Filetici, "Tuning acetylated chromatin with HAT inhibitors: a novel tool for therapy" *Epigenetics* 5(2):105-11 (2010); Bandyopadhyay, K., et al., "Spermidinyl-CoA-based HAT inhibitors block DNA repair and provide cancer-specific chemo- and radiosensitization," *Cell Cycle* 8(17): 2779-88 (2009); Arif, M., et al., "Protein lysine acetylation in cellular function and its role in cancer manifestation," *Biochim Biophys Acta* 1799(10-12):702-16 (2010). Histone acetylation controls gene expression by recruiting protein complexes that bind directly to acetylated lysine via bromodomains. Sanchez, R. and M. M. Zhou, "The role of human bromodomains in chromatin biology and gene transcription," *Curr Opin Drug Discov Devel* 12(5):659-65 (2009). One such family, the bromodomain and extra terminal domain (BET) proteins, comprises Brd2, Brd3, Brd4, and BrdT, each of which contains two bromodomains in tandem that can independently bind to acetylated lysines, as reviewed in Wu, S. Y. and C. M. Chiang, "The double bromodomain-containing chromatin adaptor Brd4 and transcriptional regulation," *J Biol Chem* 282(18):13141-5 (2007).

Interfering with BET protein interactions via bromodomain inhibition results in modulation of transcriptional programs that are often associated with diseases characterized by dysregulation of cell cycle control, inflammatory cytokine expression, viral transcription, hematopoietic differentiation, insulin transcription, and adipogenesis. Belkina, A. C. and G. V. Denis, "BET domain co-regulators in obesity, inflammation and cancer," *Nat Rev Cancer* 12(7): 465-77 (2012). BET inhibitors are believed to be useful in the treatment of diseases or conditions related to systemic or tissue inflammation, inflammatory responses to infection or hypoxia, cellular activation and proliferation, lipid metabolism, fibrosis, and the prevention and treatment of viral infections. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends Pharmacol Sci* 33(3):146-53 (2012).

Autoimmune diseases, which are often chronic and debilitating, are a result of a dysregulated immune response, which leads the body to attack its own cells, tissues, and organs. Pro-inflammatory cytokines including IL-1β, TNF-α, IL-6, MCP-1, and IL-17 are overexpressed in autoimmune disease. IL-17 expression defines the T cell subset known as Th17 cells, which are differentiated, in part, by IL-6, and drive many of the pathogenic consequences of autoimmune disease. Thus, the IL-6/Th17 axis represents an important, potentially druggable target in autoimmune disease therapy. Kimura, A. and T. Kishimoto, "IL-6: regulator of Treg/Th17 balance," *Eur J Immunol* 40(7):1830-5 (2010). BET inhibitors are expected to have anti-inflammatory and immunomodulatory properties. Belkina, A. C. and G. V. Denis, "BET domain co-regulators in obesity, inflammation and cancer," *Nat Rev Cancer* 12(7):465-77 (2012); Prinjha, R. K., J. Witherington, and K. Lee, "Place your BETs: the therapeutic potential of bromodomains," *Trends Pharmacol Sci* 33(3):146-53 (2012). BET inhibitors have been shown to have a broad spectrum of anti-inflammatory effects in vitro including the ability to decrease expression of pro-inflammatory cytokines such as IL-1β, MCP-1, TNF-α, and IL-6 in activated immune cells. Mirguet, O., et al., "From ApoA1 upregulation to BET family bromodomain inhibition: discovery of I-BET151," *Bioorg Med Chem Lett* 22(8):2963-7 (2012); Nicodeme, E., et al., "Suppression of inflammation by a synthetic histone mimic," *Nature* 468(7327):1119-23 (2010); Seal, J., et al., "Identification of a novel series of BET family bromodomain inhibitors: binding mode and profile of I-BET151 (GSK1210151A)," *Bioorg Med Chem Lett* 22(8):2968-72 (2012). The mechanism for these anti-inflammatory effects may involve BET inhibitor disruption of Brd4 co-activation of NF-κB-regulated pro-inflammatory cytokines and/or displacement of BET proteins from cytokine promoters, including IL-6. Nicodeme, E., et al., "Suppression of inflammation by a synthetic histone mimic," *Nature* 468(7327):1119-23 (2010); Zhang, G., et al., "Down-regulation of NF-kappaB Transcriptional Activity in HIV associated Kidney Disease by BRD4 Inhibition," *J Biol Chem,* 287(34):8840-51 (2012); Zhou, M., et al., "Bromodomain protein Brd4 regulates human immunodeficiency virus transcription through phosphorylation of CDK9 at threonine 29," *J Virol* 83(2):1036-44 (2009). In addition, because Brd4 is involved in T-cell lineage differentiation, BET inhibitors may be useful in inflammatory disorders characterized by specific programs of T cell differentiation. Zhang, W. S., et al., "Bromodomain-Containing-Protein 4 (BRD4) Regulates RNA Polymerase II Serine 2 Phosphorylation in Human CD4+ T Cells," *J Biol Chem* (2012).

The anti-inflammatory and immunomodulatory effects of BET inhibition have also been confirmed in vivo. A BET inhibitor prevented endotoxin- or bacterial sepsis-induced death and cecal ligation puncture-induced death in mice, suggesting utility for BET inhibitors in sepsis and acute inflammatory disorders. Nicodeme, E., et al., "Suppression of inflammation by a synthetic histone mimic," *Nature* 468(7327):1119-23 (2010). A BET inhibitor has been shown to ameliorate inflammation and kidney injury in HIV-1 transgenic mice, an animal model for HIV-associated nephropathy, in part through inhibition of Brd4 interaction with NF-κB. Zhang, G., et al., "Down-regulation of NF-kappaB Transcriptional Activity in HIV associated Kidney Disease by BRD4 Inhibition," *J Biol Chem,* 287(34):8840-51 (2012). The utility of BET inhibition in autoimmune disease was demonstrated in a mouse model of multiple sclerosis, where BET inhibition resulted in abrogation of clinical signs of disease, in part, through inhibition of IL-6 and IL-17. R. Jahagirdar, S. M. et al., "An Orally Bioavailable Small Molecule RVX-297 Significantly Decreases Disease in a Mouse Model of Multiple Sclerosis," *World Congress of Inflammation,* Paris, France (2011). These results were supported in a similar mouse model where it was shown that treatment with a BET inhibitor inhibited T cell differentiation into pro-autoimmune Th1 and Th17 subsets in vitro, and further abrogated disease induction by pro-inflammatory Th1 cells. Bandukwala, H. S., et al., "Selective inhibition of CD4+ T-cell cytokine production and autoimmunity by BET protein and c-Myc inhibitors," *Proc Natl Acad Sci USA,* 109(36):14532-7 (2012).

BET inhibitors may be useful in the treatment of a variety of chronic autoimmune inflammatory conditions. Thus, one aspect of the invention provides compounds, compositions, and methods for treating autoimmune and/or inflammatory diseases by administering one or more compounds of the invention or pharmaceutical compositions comprising one or more of those compounds. Examples of autoimmune and inflammatory diseases, disorders, and syndromes that may be treated using the compounds and methods of the invention include but are not limited to, inflammatory pelvic disease, urethritis, skin sunburn, sinusitis, pneumonitis, encephalitis, meningitis, myocarditis, nephritis (Zhang, G., et al., "Down-regulation of NF-kappaB Transcriptional Activity in HIV associated Kidney Disease by BRD4 Inhibition," *J Biol Chem,* 287(34):8840-51 (2012)), osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis (Prinjha, R. K., J. Witherington, and K. Lee, "Place your BETs: the therapeutic potential of bromodomains," *Trends Pharmacol Sci* 33(3):146-53 (2012)), Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis (Bandukwala, H. S., et al., "Selective inhibition of CD4+ T-cell cytokine production and autoimmunity by BET protein and c-Myc inhibitors," *Proc Natl Acad Sci USA,* 109(36):14532-7 (2012)), scleroderma, vasculitis, autoimmune hemolytic and thrombocytopenic states, Goodpasture's syndrome, atherosclerosis, Addison's disease, Parkinson's disease, Alzheimer's disease, Type I diabetes (Belkina, A. C. and G. V. Denis, "BET domain co-regulators in obesity, inflammation and cancer," *Nat Rev Cancer* 12(7):465-77 (2012)), septic shock (Zhang, G., et al., "Down-regulation of NF-kappaB Transcriptional Activity in HIV associated Kidney Disease by BRD4 Inhibition," *J Biol Chem,* 287(34):8840-51 (2012)), systemic lupus erythematosus (SLE) (Prinjha, R. K., J. Witherington, and K. Lee, "Place your BETs: the therapeutic potential of bromodomains," *Trends Pharmacol Sci* 33(3):146-53 (2012)), rheumatoid arthritis (Denis, G. V., "Bromodomain coactivators in cancer, obesity, type 2 diabetes, and inflammation," *Discov Med* 10(55):489-99 (2010)), psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, uveitis, dry eye disease, scleroderma, mycosis fungoides, and Graves' disease.

BET inhibitors may be useful in the treatment of a wide variety of acute inflammatory conditions. Thus, one aspect of the invention provides compounds, compositions, and methods for treating inflammatory conditions including but not limited to, acute gout, giant cell arteritis, nephritis including lupus nephritis, vasculitis with organ involvement, such as glomerulonephritis, vasculitis, including giant cell arteritis, Wegener's granulomatosis, polyarteritis nodosa, Behcet's disease, Kawasaki disease, and Takayasu's arteritis.

BET inhibitors may be useful in the prevention and treatment of diseases or conditions that involve inflammatory responses to infections with bacteria, viruses, fungi, parasites, and their toxins, such as, but not limited to sepsis, sepsis syndrome, septic shock (Nicodeme, E., et al., "Suppression of inflammation by a synthetic histone mimic," *Nature* 468(7327):1119-23 (2010)), systemic inflammatory response syndrome (SIRS), multi-organ dysfunction syndrome, toxic shock syndrome, acute lung injury, adult respiratory distress syndrome (ARDS), acute renal failure, fulminant hepatitis, burns, post-surgical syndromes, sarcoidosis, Herxheimer reactions, encephalitis, myelitis, meningitis, malaria, and SIRS associated with viral infections, such as influenza, herpes zoster, herpes simplex, and coronavirus. Belkina, A. C. and G. V. Denis, "BET domain co-regulators in obesity, inflammation and cancer," *Nat Rev Cancer* 12(7):465-77 (2012). Thus, one aspect of the invention provides compounds, compositions, and methods for treating these inflammatory responses to infections with bacteria, viruses, fungi, parasites, and their toxins described herein.

Cancer is a group of diseases caused by dysregulated cell proliferation. Therapeutic approaches aim to decrease the numbers of cancer cells by inhibiting cell replication or by inducing cancer cell differentiation or death, but there is still significant unmet medical need for more efficacious therapeutic agents. Cancer cells accumulate genetic and epigenetic changes that alter cell growth and metabolism, promoting cell proliferation and increasing resistance to programmed cell death, or apoptosis. Some of these changes include inactivation of tumor suppressor genes, activation of oncogenes, and modifications of the regulation of chromatin structure, including deregulation of histone PTMs. Watson, J. D., "Curing 'incurable' cancer," *Cancer Discov* 1(6):477-80 (2011); Morin, R. D., et al., "Frequent mutation of histone-modifying genes in non-Hodgkin lymphoma" *Nature* 476(7360):298-303 (2011).

One aspect of the invention provides compounds, compositions, and methods for treating human cancer, including, but not limited to, cancers that result from aberrant translocation or overexpression of BET proteins (e.g., NUT midline carcinoma (NMC) (French, C. A., "NUT midline carcinoma," *Cancer Genet Cytogenet* 203(1):16-20 (2010) and B-cell lymphoma (Greenwald, R. J., et al., "E mu-BRD2 transgenic mice develop B-cell lymphoma and leukemia," *Blood* 103(4):1475-84 (2004)). NMC tumor cell growth is driven by a translocation of the Brd4 or Brd3 gene to the nutlin 1 gene. Filippakopoulos, P., et al., "Selective inhibition of BET bromodomains," *Nature* 468(7327):1067-73 (2010). BET inhibition has demonstrated potent antitumor activity in murine xenograft models of NMC, a rare but lethal form of cancer. The present disclosure provides a method for treating human cancers, including, but not limited to, cancers dependent on a member of the myc family of oncoproteins including c-myc, MYCN, and L-myc. Vita, M. and M. Henriksson, "The Myc oncoprotein as a therapeutic target for human cancer," *Semin Cancer Biol* 16(4): 318-30 (2006). These cancers include Burkitt's lymphoma, acute myelogenous leukemia, multiple myeloma, and aggressive human medulloblastoma. Vita, M. and M. Henriksson, "The Myc oncoprotein as a therapeutic target for human cancer," *Semin Cancer Biol* 16(4):318-30 (2006). Cancers in which c-myc is overexpressed may be particularly susceptible to BET protein inhibition; it has been shown that treatment of tumors that have activation of c-myc with a BET inhibitor resulted in tumor regression through inactivation of c-myc transcription. Dawson, M. A., et al., Inhibition of BET recruitment to chromatin as an effective treatment for MLL-fusion leukaemia. Nature, 2011. 478 (7370): p. 529-33; Delmore, J. E., et al., "BET bromodomain inhibition as a therapeutic strategy to target c-Myc," *Cell* 146(6):904-17 (2010); Mertz, J. A., et al., "Targeting MYC dependence in cancer by inhibiting BET bromodomains," *Proc Natl Acad Sci USA* 108(40):16669-74 (2011); Ott, C. J., et al., "BET bromodomain inhibition targets both c-Myc and IL7R in highrisk acute lymphoblastic leukemia," *Blood* 120(14):2843-52 (2012); Zuber, J., et al., "RNAi screen identifies Brd4 as a therapeutic target in acute myeloid leukaemia," *Nature* 478(7370):524-8 (2011).

Embodiments of the invention include methods for treating human cancers that rely on BET proteins and pTEFb (Cdk9/CyclinT) to regulate oncogenes (Wang, S. and P. M. Fischer, "Cyclin-dependent kinase 9: a key transcriptional regulator and potential drug target in oncology, virology and cardiology," *Trends Pharmacol Sci* 29(6):302-13 (2008)), and cancers that can be treated by inducing apoptosis or senescence by inhibiting Bcl2, cyclin-dependent kinase 6 (CDK6) (Dawson, M. A., et al., "Inhibition of BET recruitment to chromatin as an effective treatment for MLL-fusion leukaemia," *Nature* 478(7370):529-33 (2011)), or human telomerase reverse transcriptase (hTERT). Delmore, J. E., et al., "BET bromodomain inhibition as a therapeutic strategy to target c-Myc," *Cell* 146(6):904-17 (2010); Ruden, M. and N. Puri, "Novel anticancer therapeutics targeting telomerase," *Cancer Treat Rev* (2012).

BET inhibitors may be useful in the treatment of cancers including, but not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute myeloid leukemia (Dawson, M. A., et al., "Inhibition of BET recruitment to chromatin as an effective treatment for MLL-fusion leukaemia," *Nature* 478(7370):529-33 (2011); Mertz, J. A., et al., "Targeting MYC dependence in cancer by inhibiting BET bromodomains," *Proc Natl Acad Sci USA* 108(40): 16669-74 (2011); Zuber, J., et al., "RNAi screen identifies Brd4 as a therapeutic target in acute myeloid leukaemia," *Nature* 478(7370):524-8 (2011)), adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell acute lymphoblastic leukemia (Ott, C. J., et al., "BET bromodomain inhibition targets both c-Myc and IL7R in highrisk acute lymphoblastic leukemia," *Blood* 120(14):2843-52 (2012)), B-cell chronic lymphocytic leukemia, B-cell prolymphocytic leukemia, B-cell lymphoma (Greenwald, R. J., et al., "E mu-BRD2 transgenic mice develop B-cell lymphoma and leukemia,". *Blood* 103(4):1475-84 (2004)), basal cell carcinoma, biliary tract cancer, bladder cancer, blastoma, bone cancer, Brenner tumor, Brown tumor, Burkitt's lymphoma (Mertz, J. A., et al., "Targeting MYC dependence in cancer by inhibiting BET bromodomains," *Proc Natl Acad Sci USA* 108(40):16669-74 (2011)), breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, Leydig cell tumor, liposarcoma, lung cancer, lymphangioma, lymphangiosarcoma, lymphoepithelioma, lymphoma, acute lymphocytic leukemia, acute myelogenous leukemia (Mertz, J. A., et al., "Targeting MYC dependence in cancer by inhibiting BET bromodomains," *Proc Natl Acad Sci USA* 108(40):16669-74 (2011)), chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma (Miguel F. Segura, et al, "BRD4 is a novel therapeutic target in melanoma," *Cancer Research.* 72(8): Supplement 1 (2012)), meningioma, Merkel cell cancer, mesothelioma, metastatic urothelial carcinoma, mixed Mullerian tumor, mixed lineage leukemia (Dawson, M. A., et al., "Inhibition of BET recruitment to chromatin as an effective treatment for MLL-fusion leukaemia," *Nature* 478(7370): 529-33 (2011)), mucinous tumor, multiple myeloma (Delmore, J. E., et al., "BET bromodomain inhibition as a therapeutic strategy to target c-Myc," *Cell* 146(6):904-17 (2010)), muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, NUT-midline carcinoma (Filippakopoulos, P., et al., "Selective inhibition of BET bromodomains," *Nature* 468(7327):1067-73 (2010)), ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. Thus, one aspect of the inventions provides compounds, compositions, and methods for treating such cancers.

BET inhibitors may be useful in the treatment of benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, post-operative stricture, keloid formation, scleroderma, and cardiac fibrosis. Tang, X et al., "Assessment of Brd4 Inhibition in Idiopathic Pulmonary Fibrosis Lung Fibroblasts and in Vivo Models of Lung Fibrosis,". Am J Pathology in press (2013). Thus, one aspect of the invention provides compounds, compositions, and methods for treating such benign proliferative and fibrotic disorders.

Cardiovascular disease (CVD) is the leading cause of mortality and morbidity in the United States. Roger, V. L., et al., "Heart disease and stroke statistics—2012 update: a report from the American Heart Association," *Circulation* 125(1):e2-e220 (2012). Atherosclerosis, an underlying cause of CVD, is a multifactorial disease characterized by dyslipidemia and inflammation. BET inhibitors are expected to be efficacious in atherosclerosis and associated conditions because of aforementioned anti-inflammatory effects as well as ability to increase transcription of ApoA-I, the major constituent of HDL. Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). Accordingly, one aspect of the invention provides compounds, compositions, and methods for treating cardiovascular disease, including but not limited to atherosclerosis.

Up-regulation of ApoA-I is considered to be a useful strategy in treatment of atherosclerosis and CVD. Degoma, E. M. and D. J. Rader, "Novel HDL-directed pharmacotherapeutic strategies," *Nat Rev Cardiol* 8(5):266-77 (2011) BET inhibitors have been shown to increase ApoA-I transcription and protein expression. Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011). It has also been shown that BET inhibitors bind directly to BET proteins and inhibit their binding to acetylated histones at the ApoA-1 promoter, suggesting the presence of a BET protein repression complex on the ApoA-1 promoter, which can be functionally disrupted by BET inhibitors. It follows that, BET inhibitors may be useful in the treatment of disorders of lipid metabolism via the regulation of ApoA-I and HDL such as hypercholesterolemia, dyslipidemia, atherosclerosis (Degoma, E. M. and D. J. Rader, "Novel HDL-directed pharmacotherapeutic strategies," *Nat Rev Cardiol* 8(5):266-77 (2011)), and Alzheimer's disease and other neurological disorders. Elliott, D. A., et al., "Apolipoproteins in the brain: implications for neurological and psychiatric disorders," *Clin Lipidol* 51(4):555-573 (2010). Thus, one aspect of the invention provides compounds, compositions, and methods for treating cardiovascular disorders by upregulation of ApoA-1.

BET inhibitors may be useful in the prevention and treatment of conditions associated with ischemia-reperfusion injury such as, but not limited to, myocardial infarction, stroke, acute coronary syndromes (Prinjha, R. K., J. Witherington, and K. Lee, "Place your BETs: the therapeutic potential of bromodomains," *Trends Pharmacol Sci* 33(3): 146-53 (2012)), renal reperfusion injury, organ transplantation, coronary artery bypass grafting, cardio-pulmonary bypass procedures, hypertension, pulmonary, renal, hepatic, gastro-intestinal, or peripheral limb embolism. Accordingly, one aspect of the invention provides compounds, compositions, and methods for prevention and treatment of conditions described herein that are associated with ischemia-reperfusion injury.

Obesity-associated inflammation is a hallmark of type II diabetes, insulin resistance, and other metabolic disorders. Belkina, A. C. and G. V. Denis, "BET domain co-regulators in obesity, inflammation and cancer," *Nat Rev Cancer* 12(7): 465-77 (2012); Denis, G. V., "Bromodomain coactivators in cancer, obesity, type 2 diabetes, and inflammation," *Discov Med* 10(55):489-99 (2010). Consistent with the ability of BET inhibitors to inhibit inflammation, gene disruption of Brd2 in mice ablates inflammation and protects animals from obesity-induced insulin resistance. Wang, F., et al., "Brd2 disruption in mice causes severe obesity without Type 2 diabetes," *Biochem J* 425(1):71-83 (2010). It has been shown that Brd2 interacts with PPAR☒☒ and opposes its transcriptional function. Knockdown of Brd2 in vitro promotes transcription of PPAR ☒ -regulated networks, including those controlling adipogenesis. Denis, G. V., et al, "An emerging role for bromodomain-containing proteins in chromatin regulation and transcriptional control of adipogenesis," *FEBS Lett* 584(15):3260-8 (2010). In addition Brd2 is highly expressed in pancreatic ☒ -cells and regulates proliferation and insulin transcription. Wang, F., et al., "Brd2 disruption in mice causes severe obesity without Type 2 diabetes," *Biochem J* 425(1):71-83 (2010). Taken together, the combined effects of BET inhibitors on inflammation and metabolism decrease insulin resistance and may be useful in the treatment of pre-diabetic and type II diabetic individuals as well as patients with other metabolic complications. Belkina, A. C. and G. V. Denis, "BET domain co-regulators in obesity, inflammation and cancer," *Nat Rev Cancer* 12(7): 465-77 (2012). Accordingly, one aspect of the invention provides compounds, compositions, and methods for treatment and prevention of metabolic disorders, including but not limited to, obesity-associated inflammation, type II diabetes, and insulin resistance.

Host-encoded BET proteins have been shown to be important for transcriptional activation and repression of viral promoters. Brd4 interacts with the E2 protein of human papilloma virus (HPV) to enable E2 mediated transcription of E2-target genes. Gagnon, D., et al., "Proteasomal degradation of the papillomavirus E2 protein is inhibited by overexpression of bromodomain-containing protein 4," *J Virol* 83(9):4127-39 (2009). Similarly, Brd2, Brd3, and Brd4 all bind to latent nuclear antigen 1 (LANA1), encoded by Kaposi's sarcoma-associated herpes virus (KSHV), promoting LANA1-dependent proliferation of KSHV-infected cells. You, J., et al., "Kaposi's sarcoma-associated herpesvirus latency-associated nuclear antigen interacts with bromodomain protein Brd4 on host mitotic chromosomes," *J Virol* 80(18):8909-19 (2006). A BET inhibitor has been shown to inhibit the Brd4-mediated recruitment of the transcription elongation complex pTEFb to the Epstein-Barr virus (EBV) viral C promoter, suggesting therapeutic value for EBV-associated malignancies. Palermo, R. D., et al., "RNA polymerase II stalling promotes nucleosome occlusion and pTEFb recruitment to drive immortalization by Epstein-Barr virus," *PLoS Pathog* 7(10):e1002334 (2011). Also, a BET inhibitor reactivated HIV in models of latent T cell infection and latent monocyte infection, potentially allowing for viral eradication by complementary anti-retroviral therapy. Zhu, J., et al., "Reactivation of Latent HIV-1 by Inhibition of BRD4," *Cell Rep* (2012); Banerjee, C., et al., "BET bromodomain inhibition as a novel strategy for reactivation of HIV-1," *J Leukoc Biol* (2012); Bartholomeeusen, K., et al., "BET bromodomain inhibition activates transcription via a transient release of P-TEFb from 7SK snRNP," *J Biol Chem* (2012); Li, Z., et al., "The BET bromodomain inhibitor JQ1 activates HIV latency through antagonizing Brd4 inhibition of Tat-transactivation," *Nucleic Acids Res* (2012).

BET inhibitors may be useful in the prevention and treatment of episome-based DNA viruses including, but not limited to, human papillomavirus, herpes virus, Epstein-Barr virus, human immunodeficiency virus (Belkina, A. C. and G. V. Denis, "BET domain co-regulators in obesity, inflammation and cancer," *Nat Rev Cancer* 12(7):465-77 (2012)), adenovirus, poxvirus, hepatitis B virus, and hepatitis C virus. Thus, the invention also provides compounds, compositions, and methods for treatment and prevention of episome-based DNA virus infections described herein.

Some central nervous system (CNS) diseases are characterized by disorders in epigenetic processes. Brd2 haploinsufficiency has been linked to neuronal deficits and epilepsy. Velisek, L., et al., "GABAergic neuron deficit as an idiopathic generalized epilepsy mechanism: the role of BRD2 haploinsufficiency in juvenile myoclonic epilepsy," *PLoS One* 6(8): e23656 (2011) SNPs in various bromodomain-containing proteins have also been linked to mental disorders including schizophrenia and bipolar disorders. Prinjha, R. K., J. Witherington, and K. Lee, "Place your BETs: the therapeutic potential of bromodomains," *Trends Pharmacol Sci* 33(3):146-53 (2012). In addition, the ability of BET inhibitors to increase ApoA-I transcription may make BET inhibitors useful in Alzheimer's disease therapy considering the suggested relationship between increased ApoA-I and Alzheimer's disease and other neurological disorders. Elliott, D. A., et al., "Apolipoproteins in the brain: implications for neurological and psychiatric disorders," *Clin Lipidol* 51(4):555-573 (2010). Accordingly, one aspect of the invention provides compounds, compositions, and methods for treating such CNS diseases and disorders.

BRDT is the testis-specific member of the BET protein family which is essential for chromatin remodeling during spermatogenesis. Gaucher, J., et al., "Bromodomain-dependent stage-specific male genome programming by Brdt," *EMBO J* 31(19):3809-20 (2012); Shang, E., et al., "The first bromodomain of Brdt, a testis-specific member of the BET sub-family of double-bromodomain-containing proteins, is essential for male germ cell differentiation," *Development* 134(19):3507-15 (2007). Genetic depletion of BRDT or inhibition of BRDT interaction with acetylated histones by a BET inhibitor resulted in a contraceptive effect in mice, which was reversible when small molecule BET inhibitors were used. Matzuk, M. M., et al., "Small-Molecule Inhibition of BRDT for Male Contraception," *Cell* 150(4): 673-684 (2012); Berkovits, B. D., et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012). These data suggest potential utility of BET inhibitors as a novel and efficacious approach to male contraception. Thus, another aspect of the invention provides compounds, compositions, and methods for male contraception.

Monocyte chemotactic protein-1 (MCP-1, CCL2) plays an important role in cardiovascular disease. Niu, J. and P. E. Kolattukudy, "Role of MCP-1 in cardiovascular disease: molecular mechanisms and clinical implications," *Clin Sci (Lond)* 117(3):95-109 (2009). MCP-1, by its chemotactic activity, regulates recruitment of monocytes from the arterial lumen to the subendothelial space, where they develop into macrophage foam cells, and initiate the formation of fatty streaks which can develop into atherosclerotic plaque. Dawson, J., et al., "Targeting monocyte chemoattractant protein-1 signalling in disease," *Expert Opin Ther Targets* 7(1):35-48 (2003). The critical role of MCP-1 (and its cognate receptor CCR2) in the development of atherosclerosis has been examined in various transgenic and knockout mouse models on a hyperlipidemic background. Boring, L., et al., "Decreased lesion formation in CCR2−/− mice reveals a role for chemokines in the initiation of atherosclerosis," *Nature* 394(6696):894-7 (1998); Gosling, J., et al., "MCP-1 deficiency reduces susceptibility to atherosclerosis in mice that overexpress human apolipoprotein B," *J Clin Invest* 103(6):773-8 (1999); Gu, L., et al., "Absence of monocyte chemoattractant protein-1 reduces atherosclerosis in low density lipoprotein receptor-deficient mice," *Mol Cell* 2(2): 275-81 (1998); Aiello, R. J., et al., "Monocyte chemoattractant protein-1 accelerates atherosclerosis in apolipoprotein E-deficient mice," *Arterioscler Thromb Vasc Biol* 19(6): 1518-25 (1999). These reports demonstrate that abrogation of MCP-1 signaling results in decreased macrophage infiltration to the arterial wall and decreased atherosclerotic lesion development.

The association between MCP-1 and cardiovascular disease in humans is well-established. Niu, J. and P. E. Kolattukudy, "Role of MCP-1 in cardiovascular disease: molecular mechanisms and clinical implications," *Clin Sci (Lond)* 117(3):95-109 (2009). MCP-1 and its receptor are overexpressed by endothelial cells, smooth muscle cells, and infiltrating monocytes/macrophages in human atherosclerotic plaque. Nelken, N. A., et al., "Monocyte chemoattractant protein-1 in human atheromatous plaques," *J Clin Invest* 88(4):1121-7 (1991). Moreover, elevated circulating levels of MCP-1 are positively correlated with most cardiovascular risk factors, measures of coronary atherosclerosis burden, and the incidence of coronary heart disease (CHD). Deo, R., et al., "Association among plasma levels of monocyte chemoattractant protein-1, traditional cardiovascular risk factors, and subclinical atherosclerosis," *J Am Coll Cardiol* 44(9):1812-8 (2004). CHD patients with among the highest levels of MCP-1 are those with acute coronary syndrome (ACS). de Lemos, J. A., et al., "Association between plasma levels of monocyte chemoattractant protein-1 and long-term clinical outcomes in patients with acute coronary syndromes," *Circulation* 107(5):690-5 (2003). In addition to playing a role in the underlying inflammation associated with CHD, MCP-1 has been shown to be involved in plaque rupture, ischemic/reperfusion injury, restenosis, and heart transplant rejection. Niu, J. and P. E. Kolattukudy, "Role of MCP-1 in cardiovascular disease: molecular mechanisms and clinical implications," *Clin Sci (Lond)* 117(3):95-109 (2009).

MCP-1 also promotes tissue inflammation associated with autoimmune diseases including rheumatoid arthritis (RA) and multiple sclerosis (MS). MCP-1 plays a role in the infiltration of macrophages and lymphocytes into the joint in RA, and is overexpressed in the synovial fluid of RA patients. Koch, A. E., et al., "Enhanced production of monocyte chemoattractant protein-1 in rheumatoid arthritis," *J Clin Invest* 90(3):772-9 (1992). Blockade of MCP-1 and MCP-1 signaling in animal models of RA have also shown the importance of MCP-1 to macrophage accumulation and proinflammatory cytokine expression associated with RA. Brodmerkel, C. M., et al., "Discovery and pharmacological characterization of a novel rodent-active CCR2 antagonist, INCB3344," *J Immunol* 175(8):5370-8 (2005); Bruhl, H., et al., "Dual role of CCR2 during initiation and progression of collagen-induced arthritis: evidence for regulatory activity of CCR2+ T cells," *J Immunol* 172(2):890-8 (2004); Gong, J. H., et al., "An antagonist of monocyte chemoattractant protein 1 (MCP-1) inhibits arthritis in the MRL-lpr mouse model," *J Exp Med* 186(1):131-7 (1997); 65. Gong, J. H., et al., "Post-onset inhibition of murine arthritis using combined chemokine antagonist therapy," *Rheumatology* (Oxford 43(1): 39-42 (2004).

Overexpression of MCP-1, in the brain, cerebrospinal fluid (CSF), and blood, has also been associated with chronic and acute MS in humans. Mahad, D. J. and R. M. Ransohoff, "The role of MCP-1 (CCL2) and CCR2 in multiple sclerosis and experimental autoimmune encephalomyelitis (EAE)," *Semin Immunol* 15(1):23-32 (2003). MCP-1 is overexpressed by a variety of cell types in the brain during disease progression and contributes to the infiltration of macrophages and lymphocytes which mediate the tissue damage associated with MS. Genetic depletion of MCP-1 or CCR2 in the experimental autoimmune encephalomyelitis (EAE) mouse model, a model resembling human MS, results in resistance to disease, primarily because of decreased macrophage infiltration to the CNS. Fife, B. T., et al., "CC chemokine receptor 2 is critical for induction of experimental autoimmune encephalomyelitis," *J Exp Med* 192(6):899-905 (2000); Huang, D. R., et al., "Absence of monocyte chemoattractant protein 1 in mice leads to decreased local macrophage recruitment and antigen-specific T helper cell type 1 immune response in experimental autoimmune encephalomyelitis," *J Exp Med* 193(6):713-26 (2001).

Preclinical data have suggested that small- and large-molecule inhibitors of MCP-1 and CCR2 have potential as therapeutic agents in inflammatory and autoimmune indications. Thus, one aspect of the invention provides compounds, compositions, and methods for treating cardiovascular, inflammatory, and autoimmune conditions associated with MCP-1 and CCR2.

Accordingly, the invention provides compounds that are useful for inhibition of BET protein function by binding to bromodomains, pharmaceutical compositions comprising one or more of those compounds, and use of these compounds or compositions in the treatment and prevention of diseases and conditions, including, but not limited to, cancer, autoimmune, and cardiovascular diseases.

The compounds of the invention are defined by Formula I:

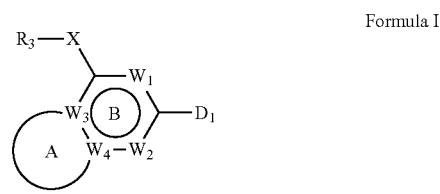

Formula I or a stereoisomer, tautomer, pharmaceutically acceptable salt, or hydrate thereof, wherein:

A is a 5-membered monocyclic heterocycle having the formula

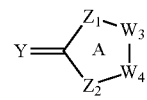

and is fused to ring B to form an A-B bicyclic ring,

B is a six-membered carbocycle or heterocycle;

$W_1$ is selected from N and $CR_1$;

$W_2$ is $CR_2$;

$W_3$ and $W_4$ are C;

$R_1$ and $R_2$ are independently selected from hydrogen, deuterium, alkyl, —OH, —$NH_2$, -thioalkyl, and alkoxy;

X is optionally present, and if present, is selected from —(NH)—, —$NHCR_xR_y$—, —$NHSO_2$—, oxygen, —$CH_2CH_2$—, —CH=CH—, —$CR_xR_yNH$—, —$OCR_xR_y$—, —$CR_xR_yO$—, —$SCR_xR_y$—, —$CR_xR_yS$—, where S might be oxidized to sulfoxide or sulfone, or —NHC(O)—, wherein the nitrogen is connected to the B ring;

$Z_1$ and $Z_2$ are independently selected from oxygen and —N—$R_a$;

Y is selected from O and S;

each $R_a$ is independently selected from hydrogen, deuterium, and alkyl($C_1$-) (methyl, ethyl, propyl, cyclopropyl);

$R_x$ and $R_y$ are each independently selected from hydrogen, alkyl($C_{1-5}$), halogen, —OH, —$CF_3$, deuterium, amino, alkoxy($C_{1-5}$), or two substituents selected from $R_x$, $R_y$, and $R_1$ may be connected in a 5- or 6-membered ring to form a bicyclic carbocycle or bicyclic heterocycle;

$R_3$ is selected from hydrogen, 4-7 membered carbocycles, 4-7-membered heterocycles, bicyclic carbocycles, and bicyclic heterocycles;

with the proviso that $R_3$ cannot be hydrogen if X is different from —NH—, and $D_1$ is selected from 5-membered monocyclic carbocycles and heterocycles connected to the B-ring via a carbon-carbon bond, with the proviso that $D_1$ cannot be a substituted or unsubstituted furan, thiophene, cyclopentane, tetrahydrofurane, and tetrahydrothiophene.

Other compounds of the invention are described by Formula IA:

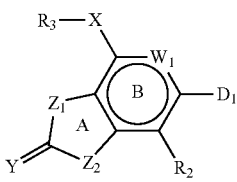

Formula IA or a stereoisomer, tautomer, pharmaceutically acceptable salt, or hydrate thereof,
wherein:
$W_1$ is selected from N and $CR_1$;
$R_1$ and $R_2$ are independently selected from hydrogen, deuterium, alkyl, —OH, —NH$_2$, -thioalkyl, and alkoxy;
Y is selected from O and S;
$Z_1$ and $Z_2$ are independently selected from oxygen and —N—$R_a$;
each $R_a$ is independently selected from hydrogen, deuterium, and alkyl($C_{1-5}$) (such as, e.g., methyl, ethyl, propyl, cyclopropyl);
X is optionally present, and if present, is selected from —(NH)—, —NHCR$_x$R$_y$—, —NHSO$_2$—, oxygen, —CH$_2$CH$_2$—, —CH=CH—, —CR$_x$R$_y$NH—, —OCR$_x$R$_y$—, —CR$_x$R$_y$O—, —SCR$_x$R$_y$—, —CR$_x$R$_y$S—, where S might be oxidized to sulfoxide or sulfone, or —NHC(O)—, wherein the nitrogen is connected to the B ring;
$R_x$ and $R_y$ are each independently selected from hydrogen, alkyl($C_{1-5}$), halogen, —OH, —CF$_3$, deuterium, amino, alkoxy($C_{1-5}$), or two substituents selected from $R_x$, $R_y$ and $R_1$ may be connected in a 5- or 6-membered ring to form a bicyclic carbocycle or bicyclic heterocycle;
$R_3$ is selected from hydrogen, 4-7 membered carbocycles, 4-7-membered heterocycles, bicyclic carbocycles, and bicyclic heterocycles;
with the proviso that $R_3$ cannot be hydrogen if X is different from —NH—, and
$D_1$ is selected from 5-membered monocyclic carbocycles and heterocycles connected to the B-ring via a carbon-carbon bond,
with the proviso that $D_1$ cannot be a substituted or unsubstituted furan, thiophene, cyclopentane, tetrahydrofurane, and tetrahydrothiophene.

In another aspect of the invention, a pharmaceutical composition comprising a compound of Formula I, or stereoisomer, tautomer, pharmaceutically acceptable salt, or hydrate thereof and one or more pharmaceutically acceptable carriers, diluents or excipients is provided.

In yet another aspect of the invention there is provided a compound of Formula I or Formula IA, or a stereoisomer, tautomer, pharmaceutically acceptable salt, or hydrate thereof for use in therapy, in particular in the treatment of diseases or conditions for which a bromodomain inhibitor is indicated.

In yet another aspect of the invention there is provided a compound of Formula I or Formula IA, or a stereoisomer, tautomer, pharmaceutically acceptable salt, or hydrate thereof in the manufacture of a medicament for the treatment of diseases or conditions for which a bromodomain inhibitor is indicated.

Definitions

As used in the present specification, the following words, phrases and symbols are generally intended to have the meanings as set forth below, except to the extent that the context in which they are used indicates otherwise. The following abbreviations and terms have the indicated meanings throughout.

As used herein, "cardiovascular disease" refers to diseases, disorders and conditions of the heart and circulatory system that are mediated by BET inhibition. Exemplary cardiovascular diseases, including cholesterol- or lipid-related disorders, include, but are not limited to, acute coronary syndrome, angina, arteriosclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemias, dyslipoproteinemias, endothelium dysfunctions, familial hypercholesterolemia, familial combined hyperlipidemia, hypoalphalipoproteinemia, hypertriglyceridemia, hyperbetalipoproteinemia, hypercholesterolemia, hypertension, hyperlipidemia, intermittent claudication, ischemia, ischemia reperfusion injury, ischemic heart diseases, cardiac ischemia, metabolic syndrome, multi-infarct dementia, myocardial infarction, obesity, peripheral vascular disease, reperfusion injury, restenosis, renal artery atherosclerosis, rheumatic heart disease, stroke, thrombotic disorder, transitory ischemic attacks, and lipoprotein abnormalities associated with Alzheimer's disease, obesity, diabetes mellitus, syndrome X, impotence, multiple sclerosis, Parkinson's disease, and inflammatory diseases.

As used herein, "inflammatory diseases" refers to diseases, disorders, and conditions that are mediated by BET inhibition. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cancer" refers to diseases, disorders, and conditions that are mediated by BET inhibition. Exemplary cancers, include, but are not limited to, chronic lymphocytic leukemia and multiple myeloma, follicular lymphoma, diffuse large B cell lymphoma with germinal center phenotype, Burkitt's lymphoma, Hodgkin's lymphoma, follicular lymphomas and activated, anaplastic large cell lymphoma, neuroblastoma and primary neuroectodermal tumor, rhabdomyosarcoma, prostate cancer, breast cancer, NMC (NUT-midline carcinoma), acute myeloid leukemia (AML), acute B lymphoblastic leukemia (B-ALL), Burkitt's Lymphoma, B-cell lymphoma, melanoma, mixed lineage leukemia, multiple myeloma, pro-myelocytic leukemia (PML), non-Hodgkin's lymphoma, neuroblastoma, medulloblastoma, lung carcinoma (NSCLC, SCLC), and colon carcinoma.

"Subject" refers to an animal, such as a mammal, that has been or will be the object of treatment, observation, or experiment. The methods described herein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "hydrate" refers to a crystal form with either a stoichiometric or non-stoichiometric amount of water is incorporated into the crystal structure.

The term "alkenyl" as used herein refers to an unsaturated straight or branched hydrocarbon having at least one carbon-carbon double bond, such as a straight or branched group of 2-8 carbon atoms, referred to herein as $(C_2-C_8)$alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-8 carbon atoms, referred to herein as $(C_1-C_8)$alkoxy. Exemplary alkoxy groups include, but are not limited to methoxy and ethoxy.

The term "alkyl" as used herein refers to a saturated straight or branched hydrocarbon, such as a straight or branched group of 1-8 carbon atoms, referred to herein as $(C_1-C_8)$alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkynyl" as used herein refers to an unsaturated straight or branched hydrocarbon having at least one carbon-carbon triple bond, such as a straight or branched group of 2-8 carbon atoms, referred to herein as $(C_2-C_8)$alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "amide" as used herein refers to the form —NR$_a$C(O)(R$_b$)— or —C(O)NR$_b$R$_c$, wherein R$_a$, R$_b$ and R$_c$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, R$_b$, or R$_c$. The amide also may be cyclic, for example R$_b$ and R$_c$, may be joined to form a 3- to 8-membered ring, such as 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa, an amino group attached to a carboxy group (e.g., -amino-COOH or salts such as -amino-COONa).

The term "amine" or "amino" as used herein refers to the form —NR$_d$R$_e$ or —N(R$_d$)R$_e$—, where R$_d$ and R$_e$ are independently selected from alkyl, alkenyl, alkynyl, aryl, arylalkyl, carbamate, cycloalkyl, haloalkyl, heteroaryl, heterocycle, and hydrogen. The amino can be attached to the parent molecular group through the nitrogen. The amino also may be cyclic, for example any two of R$_d$ and R$_e$ may be joined together or with the N to form a 3- to 12-membered ring (e.g., morpholino or piperidinyl). The term amino also includes the corresponding quaternary ammonium salt of any amino group. Exemplary amino groups include alkylamino groups, wherein at least one of R$_d$ or R$_e$ is an alkyl group. In some embodiments Rd and Re each may be optionally substituted with one or more hydroxyl, halogen, alkoxy, ester, or amino.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl."

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl."

The term "carbamate" as used herein refers to the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_g$, $R_h$ and $R_i$ are independently selected from aryl or heteroaryl, such as pyridine, pyridazine, pyrimidine, and pyrazine).

The term "carbocycle" as used herein refers to an aryl or cycloalkyl group.

The term "carboxy" as used herein refers to —COOH or its corresponding carboxylate salts (e.g., —COONa). The term carboxy also includes "carboxycarbonyl," e.g. a carboxy group attached to a carbonyl group, e.g., —C(O)—COOH or salts, such as —C(O)—COONa.

The term "cyano" as used herein refers to —CN.

The term "cycloalkoxy" as used herein refers to a cycloalkyl group attached to an oxygen.

The term "cycloalkyl" as used herein refers to a saturated or unsaturated cyclic, bicyclic, or bridged bicyclic hydrocarbon group of 3-12 carbons, or 3-8 carbons, referred to herein as "$(C_3-C_8)$cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl saturated or unsaturated, aryl, or heterocyclyl groups.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydrogen, hydroxyl, ketone, nitro, phosphate, sulfide, sulfinyl, sulfonyl, sulfonic acid, sulfonamide and thioketone. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "ester" refers to the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of Rj or Rk is alkyl, such as —O—C(O)-alkyl, —C(O)—O-alkyl-, and -alkyl-C(O)—O-alkyl-. Exemplary esters also include aryl or heteoraryl esters, e.g. wherein at least one of Rj or Rk is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecule. Exemplary reverse esters include succinate, D-argininate, argininate, L-lysinate and D-lysinate. Esters also include carboxylic acid anhydrides and acid halides.

The terms "halo" or "halogen" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "$(C_2-C_5)$heteroaryl."

The terms "heterocycle," "heterocyclyl," or "heterocyclic" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—Rn (such as acetyl, —C(O)CH_3) or —$R_n$—C(O)—$R_o$—. The ketone can be attached to another group through $R_n$ or $R_o$. $R_n$ or $R_o$ can be alkyl, alkenyl, alkynyl, cycloalkyl, heterocyclyl or aryl, or $R_n$ or $R_o$ can be joined to form a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "phenyl" as used herein refers to a 6-membered carbocyclic aromatic ring. The phenyl group can also be fused to a cyclohexane or cyclopentane ring. Phenyl can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide and thioketone.

The term "thioalkyl" as used herein refers to an alkyl group attached to a sulfur (—S— alkyl-).

"Alkyl," "alkenyl," "alkynyl", "alkoxy", "amino" and "amide" groups can be optionally substituted with or interrupted by or branched with at least one group selected from alkoxy, aryloxy, alkyl, alkenyl, alkynyl, amide, amino, aryl, arylalkyl, carbamate, carbonyl, carboxy, cyano, cycloalkyl, ester, ether, formyl, halogen, haloalkyl, heteroaryl, heterocyclyl, hydroxyl, ketone, phosphate, sulfide, sulfinyl, sulfonyl, sulfonic acid, sulfonamide, thioketone, ureido and N. The substituents may be branched to form a substituted or unsubstituted heterocycle or cycloalkyl.

As used herein, a suitable substitution on an optionally substituted substituent refers to a group that does not nullify the synthetic or pharmaceutical utility of the compounds of the present disclosure or the intermediates useful for preparing them. Examples of suitable substitutions include, but are not limited to: $C_{1-8}$ alkyl, alkenyl or alkynyl; $C_{1-6}$ aryl, $C_{2-5}$ heteroaryl; $C_{37}$ cycloalkyl; $C_{1-8}$ alkoxy; $C_6$ aryloxy; —CN; —OH; oxo; halo, carboxy; amino, such as —NH($C_{1-8}$ alkyl), —N($C_{1-8}$ alkyl)$_2$, —NH(($C_6$)aryl), or —N(($C_6$) aryl)$_2$; formyl; ketones, such as —CO($C_{1-8}$ alkyl), —CO(($C_6$ aryl) esters, such as —CO$_2$($C_{1-8}$ alkyl) and —CO$_2$ ($C_6$ aryl). One of skill in art can readily choose a suitable substitution based on the stability and pharmacological and synthetic activity of the compound of the present disclosure.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," *ACS Symposium Series*, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

Exemplary Embodiments of the Invention

The invention provides compounds and pharmaceutical composition comprising one or more of those compounds wherein the structure of the compound is defined by Formula I:

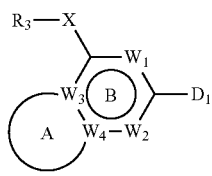

Formula I or a stereoisomer, tautomer, pharmaceutically acceptable salt, or hydrate thereof,
wherein:
A is a 5-membered monocyclic heterocycle having the formula

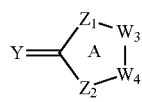

and is fused to ring B to form an A-B bicyclic ring,
B is a six-membered carbocycle or heterocycle;
$W_1$ is selected from N and $CR_1$;
$W_2$ is $CR_2$;
$W_3$ and $W_4$ are C;
Y is selected from O and S;
$Z_1$ and $Z_2$ are independently selected from oxygen and —N—$R_a$;
each $R_a$ is independently selected from hydrogen, deuterium, and alkyl($C_{1-3}$) (methyl, ethyl, propyl, cyclopropyl);
$R_1$ and $R_2$ are independently selected from hydrogen, deuterium, alkyl, —OH, —NH$_2$, -thioalkyl, and alkoxy;

X is optionally present, and if present, is selected from —(NH)—, —NHCR$_x$R$_y$—, —NHSO$_2$—, oxygen, —CH$_2$CH$_2$—, —CH=CH—, —CR$_x$R$_y$NH—, —OCR$_x$R$_y$—, —CR$_x$R$_y$O—, —SCR$_x$R$_y$—, —CR$_x$R$_y$S—, where S might be oxidized to sulfoxide or sulfone, or —NHC(O)—, wherein the nitrogen is connected to the B ring;

$R_x$ and $R_y$ are each independently selected from hydrogen, alkyl($C_{1-5}$), halogen, —OH, —CF$_3$, deuterium, amino, alkoxy($C_{1-5}$), or two substituents selected from $R_x$, $R_y$, and $R_1$ may be connected in a 5- or 6-membered ring to form a bicyclic carbocycle or bicyclic heterocycle;

$R_3$ is selected from hydrogen, 4-7 membered carbocycles, 4-7-membered heterocycles, bicyclic carbocycles, and bicyclic heterocycles;

with the proviso that $R_3$ cannot be hydrogen if X is different from —NH—, and $D_1$ is selected from 5-membered monocyclic carbocycles and heterocycles connected to the B-ring via a carbon-carbon bond, with the proviso that D cannot be a substituted or unsubstituted furan, thiophene, cyclopentane, tetrahydrofurane, and tetrahydrothiophene.

In some embodiments of Formula I, the A-B ring is a substituted or unsubstituted

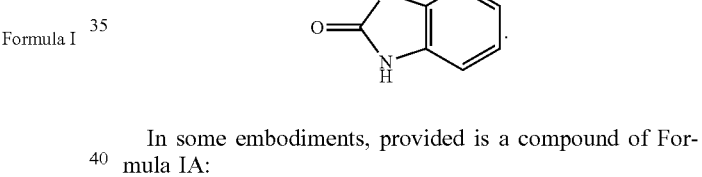

In some embodiments, provided is a compound of Formula IA:

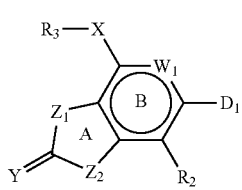

Formula IA or a stereoisomer, tautomer, pharmaceutically acceptable salt, or hydrate thereof,
wherein:
$W_1$ is selected from N and $CR_1$;
$R_1$ and $R_2$ are independently selected from hydrogen, deuterium, alkyl, —OH, —NH$_2$, -thioalkyl, and alkoxy;
Y is selected from O and S;
$Z_1$ and $Z_2$ are independently selected from oxygen and —N—$R_a$;
each $R_a$ is independently selected from hydrogen, deuterium, and alkyl($C_{1-5}$) (such as, e.g., methyl, ethyl, propyl, cyclopropyl);
X is optionally present, and if present, is selected from —(NH)—, —NHCR$_x$R$_y$—, —NHSO$_2$—, oxygen, —CH$_2$CH$_2$—, —CH=CH—, —CR$_x$R$_y$NH—, —OCR$_x$R$_y$—, —CR$_x$R$_y$O—, —SCR$_x$R$_y$—, —CR$_x$R$_y$S—, where S might be oxidized to sulfoxide or sulfone, or —NHC(O)—, wherein the nitrogen is connected to the B ring;

$R_x$ and $R_y$ are each independently selected from hydrogen, alkyl($C_{1-5}$), halogen, —OH, —$CF_3$, deuterium, amino, alkoxy($C_{1-5}$), or two substituents selected from $R_x$, $R_y$ and $R_1$ may be connected in a 5- or 6-membered ring to form a bicyclic carbocycle or bicyclic heterocycle;

$R_3$ is selected from hydrogen, 4-7 membered carbocycles, 4-7-membered heterocycles, bicyclic carbocycles, and bicyclic heterocycles;

with the proviso that $R_3$ cannot be hydrogen if X is different from —NH—, and $D_1$ is selected from 5-membered monocyclic carbocycles and heterocycles connected to the B-ring via a carbon-carbon bond, with the proviso that $D_1$ cannot be a substituted or unsubstituted furan, thiophene, cyclopentane, tetrahydrofurane, and tetrahydrothiophene.

In some embodiments of Formula IA, the A-B bicyclic ring is selected from

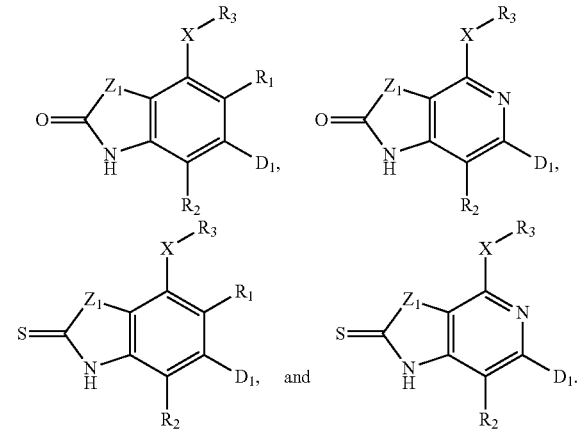

In certain embodiments of Formula IA, the A-B bicyclic ring is selected from

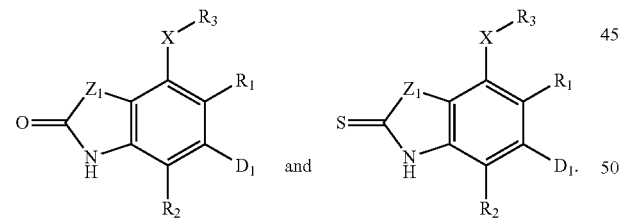

In some embodiments of Formula IA, the A-B bicyclic ring is selected from

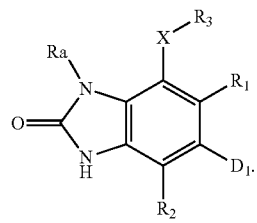

In some embodiments of Formula IA, the A-B bicyclic ring is selected from

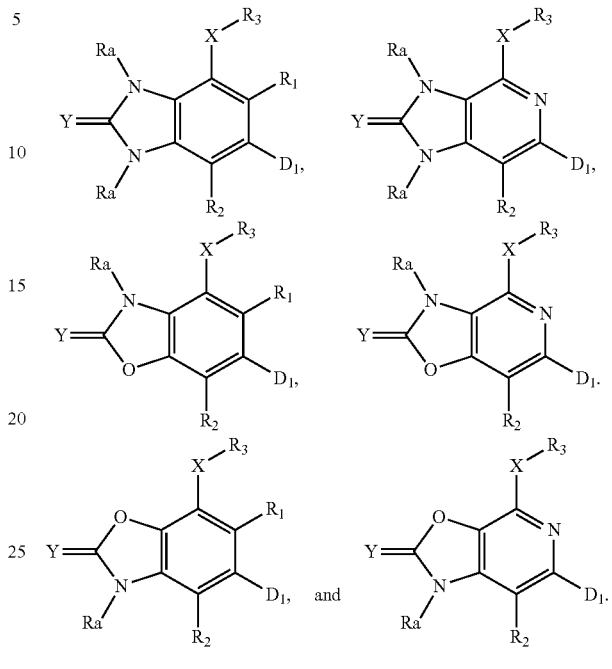

In some embodiments of Formula IA, $R_2$ is selected from hydrogen and methyl.

In some embodiments of Formula IA, one or more hydrogen atoms is replaced with deuterium.

In certain embodiments of Formula IA, $D_1$ is selected from a 5-membered monocyclic heterocycle selected from

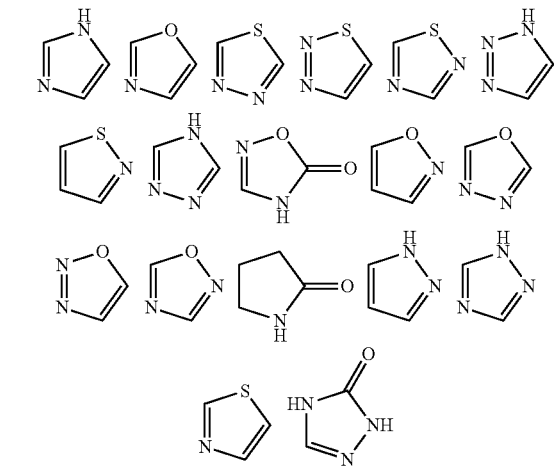

wherein the $D_1$ ring is optionally substituted with one or more deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —SO$_2$Me, —SO$_2$Et, —SO$_2$Pr), -thioalkyl(C$_1$-C$_4$) (such as —SMe, —SEt, —SPr, —SBu), —COOH, and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with one or more F, Cl, Br, —OH, —NH$_2$, —NHMe, —OMe, —SMe, oxo, and/or thio-oxo. In certain embodiments D$_1$ is optionally substituted with one or more deuterium, and C$_{(1-3)}$alkyl.

In some embodiments of Formula IA, D$_1$ is selected from a 5-membered monocyclic heterocycle selected from

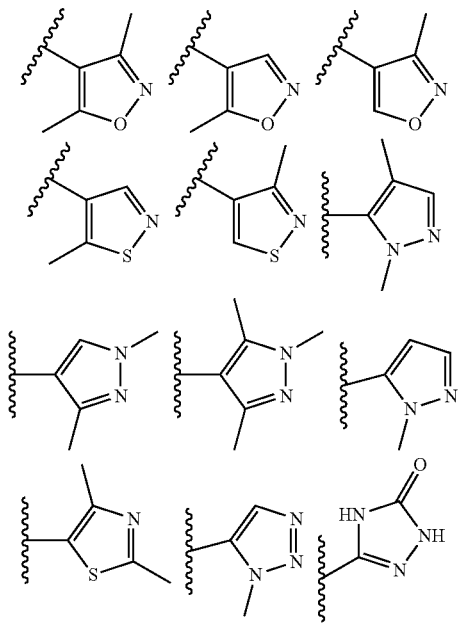

optionally substituted with one or more deuterium, alkyl (C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), —COOH, and/or ester (such as —C(O)OMe, —C(O)OEt, —C(O)OBu), wherein said alkyl (C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with one or more F, Cl, Br, —OH, —NH$_2$, —NHMe, —OMe, —SMe, oxo, and/or thio-oxo. In certain embodiments D$_1$ is optionally substituted with one or more deuterium, and C$_{(1-3)}$alkyl such as methyl.

In certain embodiments of Formula IA, D$_1$ is optionally substituted with one or more deuterium, alkyl(C$_1$-C$_4$)(such as methyl, ethyl, propyl, isopropyl, butyl), alkoxy(C$_1$-C$_4$) (such as methoxy, ethoxy, isopropoxy), wherein said alkyl (C$_1$-C$_4$) and alkoxy(C$_1$-C$_4$) may be optionally substituted with one or more F, Cl, Br, —OH, or —NH$_2$.

In other embodiments of Formula IA, D$_1$ is selected from a 5-membered monocyclic heterocycle containing one oxygen and one or two nitrogens, where the heterocycle is connected to the rest of the molecule via a carbon-carbon bond, optionally substituted with one or more hydrogen, deuterium, alkyl(C$_1$-C$_4$)(such as methyl, ethyl, propyl, isopropyl, butyl), each of which may be optionally substituted with one or more F, Cl, Br, —OH, or —NH$_2$.

In certain embodiments of Formula IA, D$_1$ is an isoxazole or pyrazole optionally substituted with one or more deuterium, alkyl(C$_1$-C$_4$)(such as methyl, ethyl, propyl, isopropyl, butyl), wherein said alkyl(C$_1$-C$_4$) may be optionally substituted with one or more F, —OH, or —NH$_2$.

In some embodiments of Formula IA, D$_1$ is an isoxazole optionally substituted with one or more one or two groups independently selected from deuterium, alkyl(C$_1$-C$_4$)(such as methyl, ethyl, propyl, isopropyl, butyl), wherein said alkyl(C$_1$-C$_4$) may be optionally substituted with one or more F, —OH, or —NH$_2$.

In some embodiments of Formula IA, D$_1$ is

In some embodiments of Formula IA, Z$_1$ is —NRa, and Ra is methyl.

In certain embodiments of Formula IA, Z$_2$ is oxygen.

In certain embodiments of Formula IA, W$_1$ is CR$_1$.

In some embodiments of Formula IA, X is optionally present, and if present, is selected from —(NH)—, —NHCR$_x$R$_y$—, —NHSO$_2$—, oxygen, —CH$_2$CH$_2$—, —CH=CH—, —CR$_x$R$_y$NH—, —OCR$_x$R$_y$—, —CR$_x$R$_y$O—, —SCR$_x$R$_y$—, where S might be oxidized to sulfoxide or sulfone, or —NHC(O)—, wherein the nitrogen is connected to the B ring. In some embodiments, X is optionally present, and if present, is selected from —(NH)—, —NHCR$_x$R$_y$—, —CR$_x$R$_y$NH—.

In certain embodiments of Formula IA, X is not present.

In certain embodiments of Formula IA, X is oxygen.

In some embodiments of Formula IA, X is —NH— and R$_3$ is hydrogen.

In other embodiments of Formula IA, R$_x$ and R$_y$ are each independently selected from hydrogen, alkyl(C$_{1-5}$), halogen, —OH, —CF$_3$, deuterium, amino, and alkoxy(C$_{1-5}$). In some embodiments, R$_x$ and R$_y$, are each independently selected from hydrogen, methyl, halogen, —CF$_3$, and deuterium.

In some embodiments of Formula IA, R$_1$ is selected from hydrogen, deuterium, alkyl, —OH, and —NH$_2$. In certain embodiments of Formula IA, R$_1$ is selected from hydrogen and methoxy. In certain embodiments of Formula IA, R$_1$ is selected from hydrogen, deuterium, —NH$_2$, and methyl. In some embodiments of Formula IA, R$_1$ is hydrogen.

In other embodiments of Formula IA, R$_2$ is selected from hydrogen, —Br, and —NH$_2$. In certain embodiments of Formula IA, R$_2$ is hydrogen.

In some embodiments of Formula IA, R$_3$ is selected from 5-6 membered carbocycles, 5-6-membered heterocycles, bicyclic carbocycles, and bicyclic heterocycles. In certain embodiments of Formula IA, R$_3$ is selected from 5-6 membered heterocycles. In certain embodiments of Formula IA, R$_3$ is selected from 5-6 membered heterocycles containing 1 or 2 nitrogens, such as unsubstituted and substituted pyrimidyl rings. In some embodiments of Formula IA, R$_3$ is selected from 6-membered heterocycles containing at least one nitrogen, such as unsubstituted and substituted pyridyl rings.

In some embodiments of Formula IA, $R_3$ is selected from

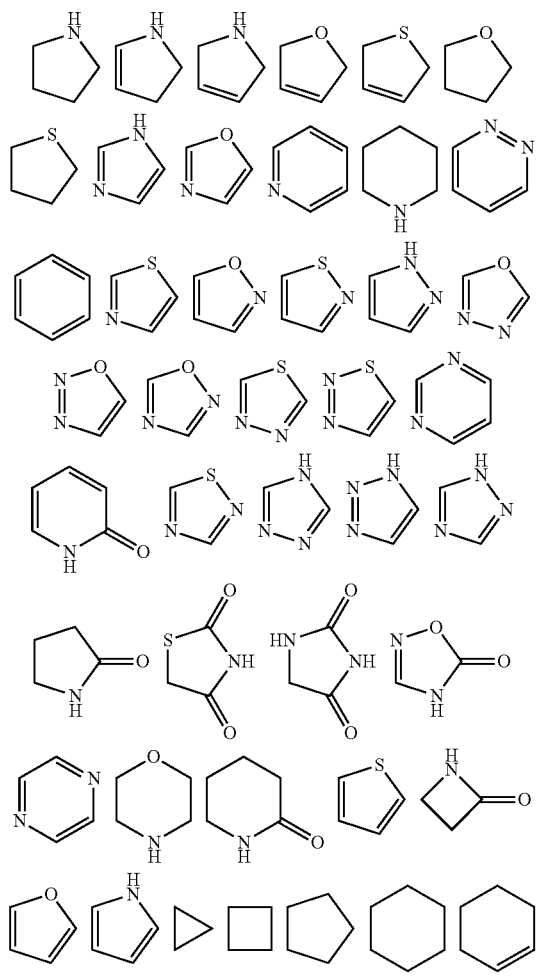

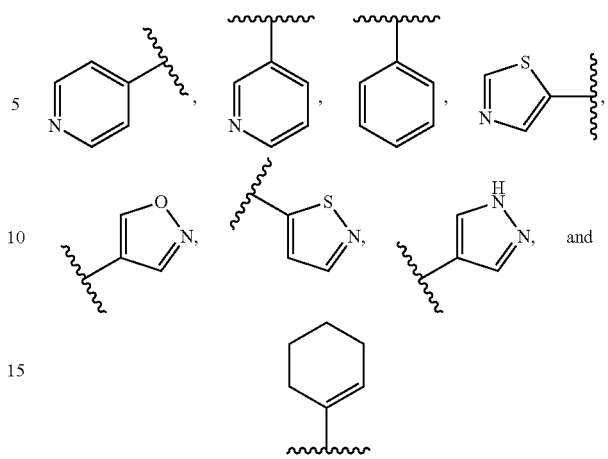

optionally substituted with one or more groups independently selected from deuterium, alkyl($C_1$-$C_4$)(such as methyl, ethyl, propyl, isopropyl, butyl), alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)$NH_2$, —C(O)NHMe, —C(O)$NEt_2$, —C(O)NiPr), —$CF_3$, and CN.

In certain embodiments of Formula IA, $R_3$ is an isoxazole or pyrazole optionally substituted with one or more groups independently selected from deuterium, alkyl($C_1$-$C_4$)(such as methyl, ethyl, propyl, isopropyl, butyl), —OH, alkoxy ($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)$NEt_2$, —C(O)NiPr), —$CF_3$, CN, —$N_3$, ketone ($C_1$-$C_4$) (such as acetyl, —C(O)Et, —C(O)Pr), —S(O)Alkyl($C_1$-$C_4$) (such as —S(O)Me, —S(O)Et), —$SO_2$alkyl($C_1$-$C_4$) (such as —$SO_2$Me, —$SO_2$Et, —$SO_2$Pr), -thioalkyl($C_1$-$C_4$) (such as —SMe, —SEt, —SPr, —SBu), carboxyl (such as —COOH), and/or ester (such as —C(O)OMe, —C(O)OEt, —C(O)OBu), wherein said alkyl($C_1$-$C_4$), alkoxy($C_1$-$C_4$), amino, amide, ketone ($C_1$-$C_4$), —S(O)Alkyl ($C_1$-$C_4$), —$SO_2$alkyl($C_1$-$C_4$), -thioalkyl($C_1$-$C_4$), and ester may be optionally substituted with one or more hydrogen, F, Cl, Br, —OH, —$NH_2$, —NHMe, —OMe, —SMe, oxo, and/or thio-oxo.

In some embodiments of Formula IA, $R_3$ is selected from 5-6 membered carbocycles, such as a substituted or unsubstituted phenyl ring. In certain embodiments $R_3$ is a 5-6 membered carbocycle substituted with a group selected from Methyl, —CF3, —OCF3, —OMe, —OEt, MeOCH2-, —Cl, —F, —CN, —NH2, —C(O)NH2, —C(O)NHMe, —NHC(O)CH3, N,N-dimethylaminomethyl, —SO2Me, and oxo.

In some embodiments of Formula IA, $R_3$ is an isoxazolyl, oxazolyl, pyrazolyl, pyridyl, pyridonyl, thiazolyl, isothiazolyl, pyrimidinyl, thiozoly, pyrazinyl, pyridazinyl, azetidinyl, pyrrolidyl, piperidinyl, morpholinyl, cyclopropyl, cyclobutyl, cyclopentyl, cyclohexyl or phenyl optionally substituted with one or more groups independently selected from hydrogen, deuterium, alkyl($C_1$-$C_4$)(such as methyl, ethyl, propyl, isopropyl, butyl), —OH, alkoxy($C_1$-$C_4$) (such as methoxy, ethoxy, isopropoxy), amino (such as —$NH_2$, —NHMe, —NHEt, —NHiPr, —NHBu —$NMe_2$, NMeEt, —$NEt_2$, —NEtBu, —NHC(O)NHalkyl), halogen (such as F, Cl), amide (such as —NHC(O)Me, —NHC(O)Et, —C(O)NHMe, —C(O)NEt₂, —C(O)NiPr), —CF₃, CN, —N₃, ketone (C₁-C₄) (such as acetyl, —C(O)Et, —C(O)Pr), —S(O)Alkyl(C₁-C₄) (such as —S(O)Me, —S(O)Et), —SO₂alkyl(C₁-C₄) (such as —SO₂Me, —SO₂Et, —SO₂Pr), -thioalkyl(C₁-C₄) (such as —SMe, —SEt, —SPr, —SBu), carboxyl (such as —COOH), and/or ester (such as —C(O)OMe, —C(O)OEt, —C(O)OBu), each of which may be optionally substituted with one or more hydrogen, F, Cl, Br, —OH, —NH₂, —NHMe, —OMe, —SMe, oxo, and/or thio-oxo.

In some embodiments of Formula IA, R₃ is optionally substituted with one or more methyl, CF₃, —OCF₃, methoxy, ethoxy, methoxymethyl, Cl, CN, F, —NH₂, amide (—CONH₂, —CONHMe, —NHCOCH₃), —COOH, —COOMe, N,N-dimethylaminomethyl, —SO₂Me, and oxo.

In certain embodiments of Formula IA, R₃ is selected from

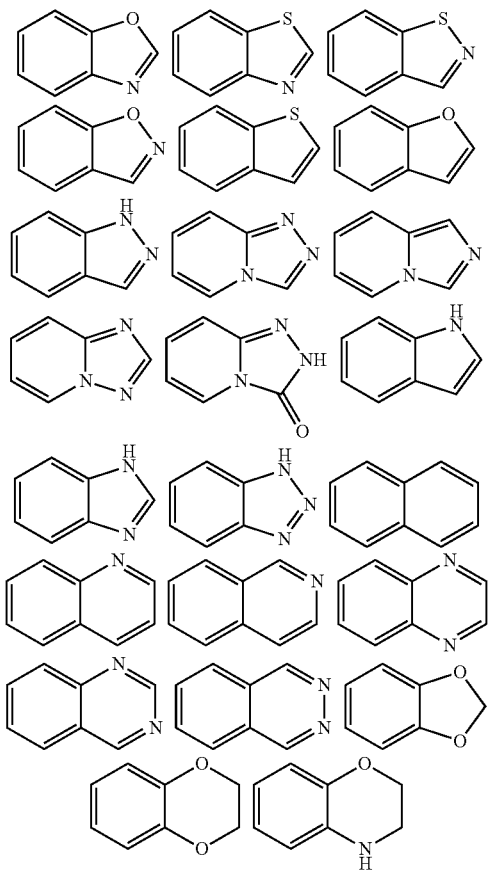

optionally substituted with one or more groups independently selected from deuterium, alkyl(C₁-C₄)(such as methyl, ethyl, propyl, isopropyl, butyl), —OH, alkoxy(C₁-C₄) (such as methoxy, ethoxy, isopropoxy), amino (such as —NH₂, —NHMe, —NHEt, —NHiPr, —NHBu —NMe₂, NMeEt, —NEt₂, —NEtBu, —NHC(O)NHalkyl), halogen (such as F, Cl), amide (such as —NHC(O)Me, —NHC(O)Et, —C(O)NHMe, —C(O)NEt₂, —C(O)NiPr), —CF₃, CN, —N₃, ketone (C₁-C₄) (such as acetyl, —C(O)Et, —C(O)Pr), —S(O)Alkyl(C₁-C₄) (such as —S(O)Me, —S(O)Et), —SO₂alkyl(C₁-C₄) (such as —SO₂Me, —SO₂Et, —SO₂Pr), -thioalkyl(C₁-C₄) (such as —SMe, —SEt, —SPr, —SBu), carboxyl (such as —COOH), and/or ester (such as —C(O)OMe, —C(O)OEt, —C(O)OBu), wherein said alkyl(C₁-C₄), alkoxy(C₁-C₄), amino, amide, ketone (C₁-C₄), —S(O)Alkyl(C₁-C₄), —SO₂alkyl(C₁-C₄), -thioalkyl(C₁-C₄), and ester may be optionally substituted with one or more hydrogen, F, Cl, Br, —OH, —NH₂, —NHMe, —OMe, —SMe, oxo, and/or thio-oxo.

In certain embodiments of Formula IA, R₃ is selected from

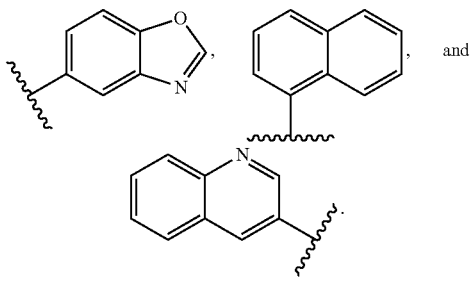

In some embodiments of Formula IA, —X—R₃ is selected from —NHAryl.

In certain embodiments of Formula IA, R₃ is pyridyl.

In some embodiments of Formula IA, the A-B bicyclic ring is selected from

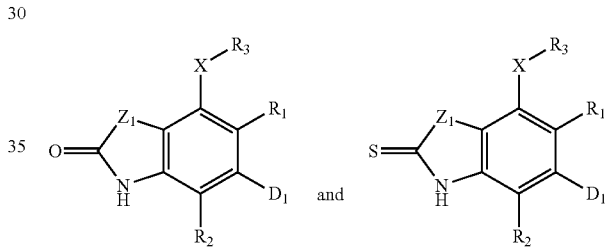

D₁ is an isoxazole or pyrazole optionally substituted with one or more deuterium, alkyl(C₁-C₄) (such as methyl, ethyl, propyl, isopropyl, butyl), alkoxy(C₁-C₄) (such as methoxy, ethoxy, isopropoxy), amino (such as —NH₂, —NHMe, —NHEt, —NHiPr, —NHBu —NMe₂, NMeEt, —NEt₂, —NEtBu, —NHC(O)NHalkyl), halogen (such as F, Cl), amide (such as —NHC(O)Me, —NHC(O)Et, —C(O)NHMe, —C(O)NEt₂, —C(O)NiPr), —CF₃, CN, —N₃, ketone (C₁-C₄) (such as acetyl, —C(O)Et, —C(O)Pr), —S(O)Alkyl(C₁-C₄) (such as —S(O)Me, —S(O)Et), —SO₂alkyl(C₁-C₄) (such as —SO₂Me, —SO₂Et, —SO₂Pr), -thioalkyl(C₁-C₄) (such as —SMe, —SEt, —SPr, —SBu), —COOH, and/or ester (such as —C(O)OMe, —C(O)OEt, —C(O)OBu), wherein said alkyl(C₁-C₄), alkoxy(C₁-C₄), amino, amide, ketone (C₁-C₄), —S(O)Alkyl(C₁-C₄), —SO₂alkyl(C₁-C₄), -thioalkyl(C₁-C₄), and ester may be optionally substituted with one or more hydrogen, F, Cl, Br, —OH, —NH₂, —NHMe, —OMe, —SMe, oxo, and/or thio-oxo;

X is optionally present, and if present, is selected from —(NH)—, —O—, —NHCR$_x$R$_y$—, —NHSO₂—, and —CR$_x$R$_y$NH; and Z₁ is —NRa; and R₃ is an isoxazole, pyrazole, pyridyl, thiazole, isothiazole, pyrimidine, phenyl, cyclohexene, benzo[d]oxazolyl, nathyl, or quinolyl, optionally substituted with one or more groups independently selected from deuterium, alkyl(C₁-C₄)(such as methyl, ethyl, propyl, isopropyl, butyl), —OH, alkoxy (C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl (C$_1$-C$_4$), —SO$_2$alkyl(C$_1$-C$_4$), -thioalkyl(C$_1$-C$_4$), and ester may be optionally substituted with one or more hydrogen, F, Cl, Br, —OH, —NH$_2$, —NHMe, —OMe, —SMe, oxo, and/or thio-oxo. In some embodiments, when X is —(NH)— then R$_3$ may be hydrogen. Alternatively, R$_3$ is selected from

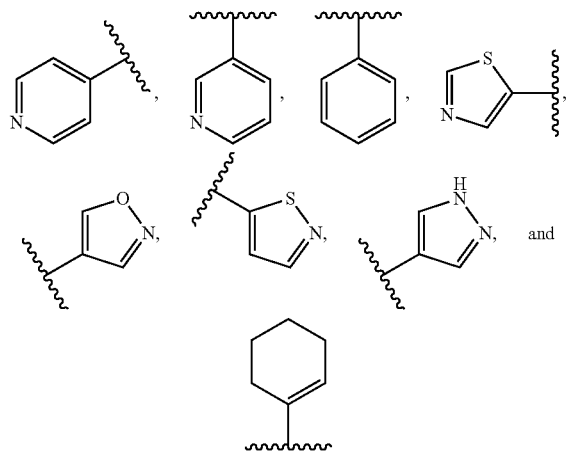

optionally substituted with one or more groups independently selected from deuterium, alkyl(C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NH$_2$, —C(O)NHMe, —C(O)NEt$_2$, —C(O)NiPr), —CF$_3$, and CN.

In some embodiments of Formula IA, the A-B bicyclic ring is selected from

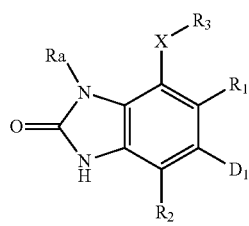

D$_1$ is an isoxazole or pyrazole optionally substituted with one or more deuterium, alkyl(C$_1$-C$_4$)(such as methyl, ethyl, propyl, isopropyl, butyl), alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —C(O)cycloamino, —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), —COOH, and/or ester (such as —C(O)OMe, —C(O)OEt, —C(O)OBu), wherein said alkyl (C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester may be optionally substituted with one or more hydrogen, F, Cl, Br, —OH, —NH$_2$, —NHMe, —OMe, —SMe, oxo, and/or thio-oxo;

X is optionally present, and if present, is selected from —(NH)—, —NHCR$_x$R$_y$—, —NHSO$_2$—, —CR$_x$R$_y$NH—, or —NH$_2$ and R$_3$ is absent; and R$_3$ is an isoxazole, pyrazole, pyridyl, thiazole, pyrimidine, or phenyl optionally substituted with one or more groups independently selected from deuterium, alkyl(C$_1$-C$_4$)(such as methyl, ethyl, propyl, isopropyl, butyl), —OH, alkoxy (C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), amide (such as —NHC(O)Me, —NHC(O)Et, —C(O)NHMe, —C(O)NEt$_2$, —C(O)NiPr), —CF$_3$, CN, —N$_3$, ketone (C$_1$-C$_4$) (such as acetyl, —C(O)Et, —C(O)Pr), —S(O)Alkyl(C$_1$-C$_4$) (such as —S(O)Me, —S(O)Et), —SO$_2$alkyl(C$_1$-C$_4$) (such as —SO$_2$Me, —SO$_2$Et, —SO$_2$Pr), -thioalkyl(C$_1$-C$_4$) (such as —SMe, —SEt, —SPr, —SBu), carboxyl (such as —COOH), and/or ester (such as —C(O)OMe, —C(O)OEt, —C(O)OBu), wherein said alkyl(C$_1$-C$_4$), alkoxy(C$_1$-C$_4$), amino, amide, ketone (C$_1$-C$_4$), —S(O)Alkyl (C$_1$-C$_4$), —SO$_2$alkyl(C$_1$-C$_4$), -thioalkyl(C$_1$-C$_4$), and ester may be optionally substituted with one or more hydrogen, F, Cl, Br, —OH, —NH$_2$, —NHMe, —OMe, —SMe, oxo, and/or thio-oxo.

In certain embodiments of Formula IA, the A-B bicyclic ring is

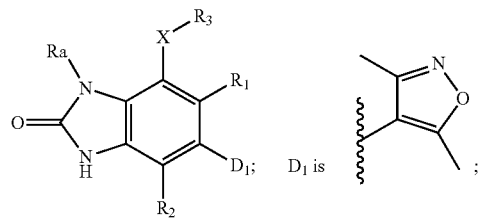

X is absent; and

R$_3$ is an isoxazole, pyrazole, or pyridyl optionally substituted with one or more groups independently selected from deuterium, alkyl(C$_1$-C$_4$)(such as methyl, ethyl, propyl, isopropyl, butyl), —OH, alkoxy(C$_1$-C$_4$) (such as methoxy, ethoxy, isopropoxy), amino (such as —NH$_2$, —NHMe, —NHEt, —NHiPr, —NHBu —NMe$_2$, NMeEt, —NEt$_2$, —NEtBu, —NHC(O)NHalkyl), halogen (such as F, Cl), —CF$_3$.

In some embodiments of Formula IA, the compound is selected from:

4,6-bis(3,5-dimethylisoxazol-4-yl)-1H-benzo[d]imidazol-2 (3H)-one;

5,7-bis(3,5-dimethylisoxazol-4-yl)-1-methyl-1H-benzo[d] imidazol-2(3H)-one;

5,7-bis(3,5-dimethylisoxazol-4-yl)benzo[d]oxazol-2(3H)-one;

5-(3,5-dimethylisoxazol-4-yl)-1-methyl-7-(2-methylpyridin-3-yl)-1H-benzo[d]imidazol-2(3H)-one;

5-(3,5-dimethylisoxazol-4-yl)-1-methyl-7-(2-(trifluoromethyl)phenyl)-1H-benzo[d]imidazol-2(3H)-one;

5-(3,5-dimethylisoxazol-4-yl)-1-methyl-7-(4-methylpyridin-3-yl)-1H-benzo[d]imidazol-2(3H)-one;

7-(1,3-dimethyl-1H-pyrazol-4-yl)-5-(3,5-dimethylisoxazol-4-yl)-1-methyl-1H-benzo[d]imidazol-2(3H)-one;

5-(3,5-dimethylisoxazol-4-yl)-1-methyl-7-(2-(trifluoromethyl)pyridin-3-yl)-1H-benzo[d]imidazol-2(3H)-one;

5-(3,5-dimethylisoxazol-4-yl)-1-methyl-7-(1,3,5-trimethyl-1H-pyrazol-4-yl)-1H-benzo[d]imidazol-2(3H)-one;

5-(3,5-dimethylisoxazol-4-yl)-1-methyl-7-(4-methylisothiazol-5-yl)-1H-benzo[d]imidazol-2(3H)-one;

5-(3,5-dimethylisoxazol-4-yl)-7-(4-fluoro-2-(trifluoromethyl)phenyl)-1-methyl-1H-benzo[d]imidazol-2(3H)-one;

5-(3,5-dimethylisoxazol-4-yl)-7-(2-methoxy-5-methylphenyl)-1-methyl-1H-benzo[d]imidazol-2(3H)-one;

5-(3,5-dimethylisoxazol-4-yl)-7-(2-methoxypyridin-3-yl)-1-methyl-1H-benzo[d]imidazol-2(3H)-one;

3-(6-(3,5-dimethylisoxazol-4-yl)-3-methyl-2-oxo-2,3-dihydro-1H-benzo[d]imidazol-4-yl)-2-methylbenzonitrile;

4,6-bis(3,5-dimethylisoxazol-4-yl)-1,3-dimethyl-1H-benzo[d]imidazol-2(3H)-one;

3-(6-(3,5-dimethylisoxazol-4-yl)-3-methyl-2-oxo-2,3-dihydro-1H-benzo[d]imidazol-4-yl)-4-methylbenzonitrile;

5-(3,5-dimethylisoxazol-4-yl)-7-(4-methoxypyridin-3-yl)-1-methyl-1H-benzo[d]imidazol-2(3H)-one;

5-(3,5-dimethylisoxazol-4-yl)-7-(5-fluoro-2-methoxyphenyl)-1-methyl-1H-benzo[d]imidazol-2(3H)-one;

7-(5-chloro-2-methylphenyl)-5-(3,5-dimethylisoxazol-4-yl)-1-methyl-1H-benzo[d]imidazol-2(3H)-one;

7-(6-amino-2-methylpyridin-3-yl)-5-(3,5-dimethylisoxazol-4-yl)-1-methyl-1H-benzo[d]imidazol-2(3H)-one;

7-(3,5-dimethyl-1H-pyrazol-4-yl)-5-(3,5-dimethylisoxazol-4-yl)-1-methyl-1H-benzo[d]imidazol-2(3H)-one;

6-(3,5-dimethylisoxazol-4-yl)-4-(1,3,5-trimethyl-1H-pyrazol-4-yl)-1H-benzo[d]imidazol-2(3H)-one;

6-(3,5-dimethylisoxazol-4-yl)-4-(1,3,5-trimethyl-1H-pyrazol-4-yl)-1H-benzo[d]imidazole-2(3H)-thione;

6-(3,5-dimethylisoxazol-4-yl)-4-(4-methylpyridin-3-yl)-1H-benzo[d]imidazole-2-thiol;

3-(6-(3,5-dimethylisoxazol-4-yl)-2-thioxo-2,3-dihydro-1H-benzo[d]imidazol-4-yl)-4-methylbenzonitrile;

5-(3,5-dimethylisoxazol-4-yl)-1-methyl-7-((1,3,5-trimethyl-1H-pyrazol-4-yl)amino)-1H-benzo[d]imidazol-2(3H)-one;

5-(3,5-dimethylisoxazol-4-yl)-1-methyl-7-((2-methylpyridin-3-yl)amino)-1H-benzo[d]imidazol-2(3H)-one;

5-(5-(hydroxymethyl)-3-methylisoxazol-4-yl)-1-methyl-7-(1,3,5-trimethyl-1H-pyrazol-4-yl)-1H-benzo[d]imidazol-2(3H)-one;

3-(6-(3,5-dimethylisoxazol-4-yl)-3-methyl-2-oxo-2,3-dihydro-1H-benzo[d]imidazol-4-yl)-4-methylbenzamide;

3-(6-(3,5-dimethylisoxazol-4-yl)-3-methyl-2-oxo-2,3-dihydro-1H-benzo[d]imidazol-4-yl)-2-methylbenzamide;

5-(3,5-dimethylisoxazol-4-yl)-1-methyl-7-((2-methylpyridin-3-yl)oxy)-1H-benzo[d]imidazol-2(3H)-one;

7-(3,5-dimethyl-1H-pyrazol-4-yl)-5-(5-(hydroxymethyl)-3-methylisoxazol-4-yl)-1-methyl-1H-benzo[d]imidazol-2(3H)-one;

5-(3,5-dimethylisoxazol-4-yl)-7-((3,5-dimethylisoxazol-4-yl)amino)-1-methyl-1H-benzo[d]imidazol-2(3H)-one;

5-(3,5-dimethylisoxazol-4-yl)-1-methyl-7-(naphthalen-1-yl)-1H-benzo[d]imidazol-2(3H)-one;

7-(3,5-dichloropyridin-4-yl)-5-(3,5-dimethylisoxazol-4-yl)-1-methyl-1H-benzo[d]imidazol-2(3H)-one;

5-(3,5-dimethylisoxazol-4-yl)-1-methyl-7-(quinolin-3-yl)-1H-benzo[d]imidazol-2(3H)-one;

7-(2-chlorophenyl)-5-(3,5-dimethylisoxazol-4-yl)-1-methyl-1H-benzo[d]imidazol-2(3H)-one;

5-(3,5-dimethylisoxazol-4-yl)-1-methyl-7-(3-methylpyridin-4-yl)-1H-benzo[d]imidazol-2(3H)-one;

5-(3,5-dimethylisoxazol-4-yl)-7-(3,5-dimethylpyridin-4-yl)-1-methyl-1H-benzo[d]imidazol-2(3H)-one;

5-(3,5-dimethylisoxazol-4-yl)-1-methyl-7-(o-tolyl)-1H-benzo[d]imidazol-2(3H)-one;

5-(3,5-dimethylisoxazol-4-yl)-7-(2-fluoro-5-methoxyphenyl)-1-methyl-1H-benzo[d]imidazol-2(3H)-one;

7-(5-chloro-2-methoxyphenyl)-5-(3,5-dimethylisoxazol-4-yl)-1-methyl-1H-benzo[d]imidazol-2(3H)-one;

5-(3,5-dimethylisoxazol-4-yl)-7-(2-fluoro-3-methoxyphenyl)-1-methyl-1H-benzo[d]imidazol-2(3H)-one;

5-(3,5-dimethylisoxazol-4-yl)-7-(2,4-dimethylthiazol-5-yl)-1-methyl-1H-benzo[d]imidazol-2(3H)-one;

5-(3,5-dimethylisoxazol-4-yl)-7-(2-methoxy-6-methylpyridin-3-yl)-1-methyl-1H-benzo[d]imidazol-2(3H)-one;

7-(benzo[d]oxazol-5-yl)-5-(3,5-dimethylisoxazol-4-yl)-1-methyl-1H-benzo[d]imidazol-2(3H)-one; and 7-(cyclohex-1-en-1-yl)-5-(3,5-dimethylisoxazol-4-yl)-1-methyl-1H-benzo[d]imidazol-2(3H)-one, or a stereoisomer, tautomer, pharmaceutically acceptable salt, or hydrate thereof.

Another aspect of the invention provides a method for inhibition of BET protein function by binding to bromodomains, and their use in the treatment and prevention of diseases and conditions in a mammal (e.g., a human) comprising administering a therapeutically effective amount of a compound of Formula I.

In one embodiment, because of potent effects of BET inhibitors in vitro on IL-6 and IL-17 transcription, BET inhibitor compounds of Formula I may be used as therapeutics for inflammatory disorders in which IL-6 and/or IL-17 have been implicated in disease. The following autoimmune diseases are amenable to therapeutic use of BET inhibition by administration of a compound of Formula I or stereoisomer, tautomer, pharmaceutically acceptable salt, or hydrate thereof because of a prominent role of IL-6 and/or IL-17: Acute Disseminated Encephalomyelitis (Ishizu, T., et al., "CSF cytokine and chemokine profiles in acute disseminated encephalomyelitis," *J Neuroimmunol* 175(1-2): 52-8 (2006)), Agammaglobulinemia (Gonzalez-Serrano, M. E., et al., "Increased Pro-inflammatory Cytokine Production After Lipopolysaccharide Stimulation in Patients with X-linked Agammaglobulinemia," *J Clin Immunol* 32(5):967-74 (2012)), Allergic Disease (McKinley, L., et al., "TH17 cells mediate steroid-resistant airway inflammation and airway hyperresponsiveness in mice," *J Immunol* 181(6):4089-97 (2008)), Ankylosing spondylitis (Taylan, A., et al., "Evaluation of the T helper 17 axis in ankylosing spondylitis," *Rheumatol Int* 32(8):2511-5 (2012)), Anti-GBM/Anti-TBM nephritis (Ito, Y., et al., "Pathogenic significance of interleukin-6 in a patient with antiglomerular basement membrane antibody-induced glomerulonephritis with multinucleated giant cells," *Am J Kidney Dis* 26(1):72-9 (1995)), Anti-phospholipid syndrome (Soltesz, P., et al., "Immunological features of primary anti-phospholipid syndrome in connection with endothelial dysfunction," *Rheumatology* (Oxford) 47(11):1628-34 (2008)), Autoimmune aplastic anemia (Gu, Y., et al., "Interleukin (IL)-17 promotes macrophages to produce IL-8, IL-6 and tumour necrosis factor-alpha in aplastic anaemia," *Br J Haematol* 142(1):109-14 (2008)), Autoimmune hepatitis (Zhao, L., et al., "Interleukin-17 contributes to the pathogenesis of autoimmune hepatitis through inducing hepatic interleukin-6 expression," *PLoS One* 6(4):e18909 (2011)), Autoimmune inner ear disease (Gloddek, B., et al., "Pharmacological influence on inner ear endothelial cells in relation to the pathogenesis of sensorineural hearing loss," *Adv Otorhinolaryngol* 59:75-83 (2002)), Autoimmune myocarditis (Yamashita, T., et al., "IL-6-mediated Th17 differentiation through RORgammat is essential for the initiation of experimental autoimmune myocarditis," *Cardiovasc Res* 91(4):640-8 (2011)), Autoimmune pancreatitis (Ni, J., et al., "Involvement of Interleukin-17A in Pancreatic Damage in Rat Experimental Acute Necrotizing Pancreatitis," *Inflammation* (2012)), Autoimmune retinopathy (Hohki, S., et al., "Blockade of interleukin-6 signaling suppresses experimental autoimmune uveoretinitis by the inhibition of inflammatory Th17 responses," *Exp Eye Res* 91(2):162-70 (2010)), Autoimmune thrombocytopenic purpura (Ma, D., et al., "Profile of Th17 cytokines (IL-17, TGF-beta, IL-6) and Th1 cytokine (IFN-gamma) in patients with immune thrombocytopenic purpura," *Ann Hematol* 87(11):899-904 (2008)), Behcet's Disease (Yoshimura, T., et al., "Involvement of Th17 cells and the effect of anti-IL-6 therapy in autoimmune uveitis," *Rheumatology* (Oxford) 48(4):347-54 (2009)), Bullous pemphigoid (D'Auria, L., P. et al., "Cytokines and bullous pemphigoid," *Eur Cytokine Netw* 10(2):123-34 (1999)), Castleman's Disease (El-Osta, H. E. and R. Kurzrock, "Castleman's disease: from basic mechanisms to molecular therapeutics," *Oncologist* 16(4):497-511 (2011)), Celiac Disease (Landenpera, A. I., et al., "Up-regulation of small intestinal interleukin-17 immunity in untreated coeliac disease but not in potential coeliac disease or in type 1 diabetes," *Clin Exp Immunol* 167(2):226-34 (2012)), Churg-Strauss syndrome (Fujioka, A., et al., "The analysis of mRNA expression of cytokines from skin lesions in Churg-Strauss syndrome," *J Dermatol* 25(3):171-7 (1998)), Crohn's Disease (Holtta, V., et al., "IL-23/IL-17 immunity as a hallmark of Crohn's disease," *Inflamm Bowel Dis* 14(9):1175-84 (2008)), Cogan's syndrome (Shibuya, M., et al., "Successful treatment with tocilizumab in a case of Cogan's syndrome complicated with aortitis," *Mod Rheumatol* (2012)), Dry eye syndrome (De Paiva, C. S., et al., "IL-17 disrupts corneal barrier following desiccating stress," *Mucosal Immunol* 2(3):243-53 (2009)), Essential mixed cryoglobulinemia (Antonelli, A., et al., "Serum levels of proinflammatory cytokines interleukin-1beta, interleukin-6, and tumor necrosis factor alpha in mixed cryoglobulinemia," *Arthritis Rheum* 60(12):3841-7 (2009)), Dermatomyositis (Chevrel, G., et al., "Interleukin-17 increases the effects of IL-1 beta on muscle cells: arguments for the role of T cells in the pathogenesis of myositis," *J Neuroimmunol* 137(1-2):125-33 (2003)), Devic's Disease (Linhares, U. C., et al., "The Ex Vivo Production of IL-6 and IL-21 by CD4(+) T Cells is Directly Associated with Neurological Disability in Neuromyelitis Optica Patients," *J Clin Immunol* (2012)), Encephalitis (Kyburz, D. and M. Corr, "Th17 cells generated in the absence of TGF-beta induce experimental allergic encephalitis upon adoptive transfer," *Expert Rev Clin Immunol* 7(3):283-5 (2011)), Eosinophlic esophagitis (Dias, P. M. and G. Banerjee, "The Role of Th17/IL-17 on Eosinophilic Inflammation," *J Autoimmun* (2012)), Eosinophilic fasciitis (Dias, P. M. and G. Banerjee, "The Role of Th17/IL-17 on Eosinophilic Inflammation," *J Autoimmun* (2012)), Erythema nodosum (Kahawita, I. P. and D. N. Lockwood, "Towards understanding the pathology of erythema nodosum leprosum," *Trans R Soc Trop Med Hyg* 102(4):329-37 (2008)), Giant cell arteritis (Deng, J., et al., "Th17 and Th1 T-cell responses in giant cell arteritis," *Circulation* 121(7): 906-15 (2010)), Glomerulonephritis (Ooi, J. D., et al., "Review: T helper 17 cells: their role in glomerulonephritis," *Nephrology* (Carlton) 15(5):513-21 (2010)), Goodpasture's syndrome (Ito, Y., et al., "Pathogenic significance of interleukin-6 in a patient with antiglomerular basement membrane antibody-induced glomerulonephritis with multinucleated giant cells," *Am J Kidney Dis* 26(1):72-9 (1995)), Granulomatosis with Polyangiitis (Wegener's) (Nakahama, H., et al., "Distinct responses of interleukin-6 and other laboratory parameters to treatment in a patient with Wegener's granulomatosis," *Intern Med* 32(2):189-92 (1993)), Graves' Disease (Kim, S. E., et al., "Increased serum interleukin-17 in Graves' ophthalmopathy," *Graefes Arch Clin Exp Ophthalmol* 250(10):1521-6 (2012)), Guillain-Barre syndrome (Lu, M. O. and J. Zhu, "The role of cytokines in Guillain-Barre syndrome," *J Neurol* 258(4): 533-48 (2011)), Hashimoto's thyroiditis (Figueroa-Vega, N., et al., "Increased circulating pro-inflammatory cytokines and Th17 lymphocytes in Hashimoto's thyroiditis," *J Clin Endocrinol Metab* 95(2):953-62 (2009)), Hemolytic anemia (Xu, L., et al., "Critical role of Th17 cells in development of autoimmune hemolytic anemia," *Exp Hematol* (2012)), Henoch-Schonlein purpura (Jen, H. Y., et al., "Increased serum interleukin-17 and peripheral Th17 cells in children with acute Henoch-Schonlein purpura," *Pediatr Allergy Immunol* 22(8):862-8 (2011)), IgA nephropathy (Lin, F. J., et al., "Imbalance of regulatory T cells to Th17 cells in IgA nephropathy," *Scand J Clin Lab Invest* 72(3):221-9 (2012)), Inclusion body myositis (Baron, P., et al., "Production of IL-6 by human myoblasts stimulated with Abeta: relevance in the pathogenesis of IBM," *Neurology* 57(9):1561-5 (2001)), Type I diabetes (Belkina, A. C. and G. V. Denis, "BET domain co-regulators in obesity, inflammation and cancer," *Nat Rev Cancer* 12(7):465-77 (2012)), Interstitial cystitis (Lamale, L. M., et al., "Interleukin-6, histamine, and methylhistamine as diagnostic markers for interstitial cystitis," *Urology* 68(4):702-6 (2006)), Kawasaki's Disease (Jia, S., et al., "The T helper type 17/regulatory T cell imbalance in patients with acute Kawasaki disease," *Clin Exp Immunol* 162(1):131-7 (2010)), Leukocytoclastic vasculitis (Min, C. K., et al., "Cutaneous leucocytic vasculitis (LV) following bortezomib therapy in a myeloma patient; association with pro-inflammatory cytokines,"*Eur J Haematol* 76(3):265-8 (2006)), Lichen planus (Rhodus, N. L., et al., "Proinflammatory cytokine levels in saliva before and after treatment of (erosive) oral lichen planus with dexamethasone," *Oral Dis* 12(2):112-6 (2006)), Lupus (SLE) (Mok, M. Y., et al., "The relation of interleukin 17 (IL-17) and IL-23 to Th1/Th2 cytokines and disease activity in systemic lupus erythematosus," *J Rheumatol* 37(10):2046-52 (2010)), Microscopic polyangitis (Muller Kobold, A. C., et al., "In vitro up-regulation of E-selectin and induction of interleukin-6 in endothelial cells by autoantibodies in Wegener's granulomatosis and microscopic polyangiitis," *Clin Exp Rheumatol* 17(4):433-40 (1999)), Multiple sclerosis (Jadidi-Niaragh, F. and Mirshafiey A., "Th17 cell, the new player of neuroinflammatory process in multiple sclerosis," *Scand J Immunol* 74(1):1-13 (2011)), Myasthenia gravis (Aricha, R., et al., "Blocking of IL-6 suppresses experimental autoimmune myasthenia gravis," *J Autoimmun* 36(2):135-41 (2011)), myositis (Chevrel, G., et al., "Interleukin-17 increases the effects of IL-1 beta on muscle cells: arguments for the role of T cells in the pathogenesis of myositis," *J Neuroimmunol*

137(1-2):125-33 (2003)), Optic neuritis (Icoz, S., et al., "Enhanced IL-6 production in aquaporin-4 antibody positive neuromyelitis optica patients," *Int j Neurosci* 120(1):71-5 (2010)), Pemphigus (Lopez-Robles, E., et al., "TNFalpha and IL-6 are mediators in the blistering process of pemphigus," *Int J Dermatol* 40(3):185-8 (2001)), POEMS syndrome (Kallen, K. J., et al., "New developments in IL-6 dependent biology and therapy: where do we stand and what are the options?" *Expert Opin Investig Drugs* 8(9):1327-49 (1999)), Polyarteritis nodosa (Kawakami, T., et al., "Serum levels of interleukin-6 in patients with cutaneous polyarteritis nodosa," *Acta Derm Venereol* 92(3):322-3 (2012)), Primary biliary cirrhosis (Harada, K., et al., "Periductal interleukin-17 production in association with biliary innate immunity contributes to the pathogenesis of cholangiopathy in primary biliary cirrhosis," *Clin Exp Immunol* 157(2):261-70 (2009)), Psoriasis (Fujishima, S., et al., "Involvement of IL-17F via the induction of IL-6 in psoriasis," *Arch Dermatol Res* 302(7):499-505 (2010)), Psoriatic arthritis (Raychaudhuri, S. P., et al., IL-17 receptor and its functional significance in psoriatic arthritis," *Mol Cell Biochem* 359 (1-2):419-29 (2012)), Pyoderma gangrenosum (Kawakami, T., et al., "Reduction of interleukin-6, interleukin-8, and anti-phosphatidylserine-prothrombin complex antibody by granulocyte and monocyte adsorption apheresis in a patient with pyoderma gangrenosum and ulcerative colitis," *Am J Gastroenterol* 104(9):2363-4 (2009)), Relapsing polychondritis (Kawai, M., et al., "Sustained response to tocilizumab, anti-interleukin-6 receptor antibody, in two patients with refractory relapsing polychondritis," *Rheumatology* (Oxford) 48(3):318-9 (2009)), Rheumatoid arthritis (Ash, Z. and P. Emery, "The role of tocilizumab in the management of rheumatoid arthritis," *Expert Opin Biol Ther,* 12(9):1277-89 (2012)), Sarcoidosis (Belli, F., et al., "Cytokines assay in peripheral blood and bronchoalveolar lavage in the diagnosis and staging of pulmonary granulomatous diseases," *Int J Immunopathol Pharmacol* 13(2):61-67 (2000)), Scleroderma (Radstake, T. R., et al., "The pronounced Th17 profile in systemic sclerosis (SSc) together with intracellular expression of TGFbeta and IFNgamma distinguishes SSc phenotypes," *PLoS One,* 4(6): e5903 (2009)), Sjogren's syndrome (Katsifis, G. E., et al., "*Systemic and local interleukin-17 and linked cytokines associated with Sjogren's syndrome immunopathogenesis,"* Am J Pathol* 175(3):1167-77 (2009)), Takayasu's arteritis (Sun, Y., et al., "MMP-9 and IL-6 are potential biomarkers for disease activity in Takayasu's arteritis," *Int J Cardiol* 156(2):236-8 (2012)), Transverse myelitis (Graber, J. J., et al., "Interleukin-17 in transverse myelitis and multiple sclerosis," *J Neuroimmunol* 196(1-2):124-32 (2008)), Ulcerative colitis (Mudter, J. and M. F. Neurath, "Il-6 signaling in inflammatory bowel disease: pathophysiological role and clinical relevance," *Inflamm Bowel Dis* 13(8):1016-23 (2007)), Uveitis (Haruta, H., et al., "Blockade of interleukin-6 signaling suppresses not only th17 but also interphotoreceptor retinoid binding protein-specific Th1 by promoting regulatory T cells in experimental autoimmune uveoretinitis," *Invest Ophthalmol Vis Sci* 52(6):3264-71 (2011)), and Vitiligo (Bassiouny, D. A. and O. Shaker, "Role of interleukin-17 in the pathogenesis of vitiligo," *Clin Exp Dermatol* 36(3):292-7 115. (2011)). Thus, the invention includes compounds of Formula I, stereoisomers, tautomers, pharmaceutically acceptable salts, or hydrates thereof; pharmaceutical compositions comprising one or more of those compounds; and methods of using those compounds or compositions for treating these diseases.

Acute and chronic (non-autoimmune) inflammatory diseases characterized by increased expression of pro-inflammatory cytokines, including IL-6, MCP-1, and IL-17, would also be amenable to therapeutic BET inhibition. These include, but are not limited to, sinusitis (Bradley, D. T. and S. E. Kountakis, "Role of interleukins and transforming growth factor-beta in chronic rhinosinusitis and nasal polyposis," Laryngoscope 115(4):684-6 (2005)), pneumonitis (Besnard, A. G., et al., "*Inflammasome-IL-1-Th17 response in allergic lung inflammation"* J Mol Cell Biol* 4(1):3-10 (2012)), osteomyelitis (Yoshii, T., et al., "Local levels of interleukin-1beta, -4, -6 and tumor necrosis factor alpha in an experimental model of murine osteomyelitis due to *staphylococcus aureus,*" *Cytokine* 19(2):59-65 2002), gastritis (Bayraktaroglu, T., et al., "Serum levels of tumor necrosis factor-alpha, interleukin-6 and interleukin-8 are not increased in dyspeptic patients with *Helicobacter pylori*-associated gastritis," *Mediators Inflamm* 13(1):25-8 (2004)), enteritis (Mitsuyama, K., et al., "STAT3 activation via interleukin 6 trans-signalling contributes to ileitis in SAMP1/Yit mice," *Gut* 55(9):1263-9. (2006)), gingivitis (Johnson, R. B., et al., "Interleukin-11 and IL-17 and the pathogenesis of periodontal disease," *J Periodontol* 75(1): 37-43 (2004)), appendicitis (Latifi, S. Q., et al., "Persistent elevation of serum interleukin-6 in intraabdominal sepsis identifies those with prolonged length of stay," *J Pediatr Surg* 39(10):1548-52 (2004)), irritable bowel syndrome (Ortiz-Lucas, M., et al., "Irritable bowel syndrome immune hypothesis. Part two: the role of cytokines," *Rev Esp Enferm Dig* 102(12):711-7 (2010)), tissue graft rejection (Kappel, L. W., et al., "IL-17 contributes to CD4-mediated graft-versus-host disease," *Blood* 113(4):945-52 (2009)), chronic obstructive pulmonary disease (COPD) (Traves, S. L. and L. E. Donnelly, "Th17 cells in airway diseases," *Curr Mol Med* 8(5):416-26 (2008)), septic shock (toxic shock syndrome, SIRS, bacterial sepsis, etc) (Nicodeme, E., et al., "Suppression of inflammation by a synthetic histone mimic," *Nature* 468(7327):1119-23 (2010)), osteoarthritis (Chen, L., et al., "IL-17RA aptamer-mediated repression of IL-6 inhibits synovium inflammation in a murine model of osteoarthritis," *Osteoarthritis Cartilage* 19(6):711-8 (2011)), acute gout (Urano, W., et al., "The inflammatory process in the mechanism of decreased serum uric acid concentrations during acute gouty arthritis," *J Rheumatol* 29(9):1950-3 (2002)), acute lung injury (Traves, S. L. and L. E. Donnelly, "Th17 cells in airway diseases," *Curr Mol Med* 8(5):416-26 (2008)), acute renal failure (Simmons, E. M., et al., "Plasma cytokine levels predict mortality in patients with acute renal failure," *Kidney Int* 65(4):1357-65 (2004)), burns (Paquet, P. and G. E. Pierard, "Interleukin-6 and the skin," *Int Arch Allergy Immunol* 109(4):308-17 (1996)), Herxheimer reaction (Kaplanski, G., et al., "Jarisch-Herxheimer reaction complicating the treatment of chronic Q fever endocarditis: elevated TNFalpha and IL-6 serum levels," *J Infect* 37(1): 83-4 (1998)), and SIRS associated with viral infections (Belkina, A. C. and G. V. Denis, "BET domain co-regulators in obesity, inflammation and cancer," *Nat Rev Cancer* 12(7): 465-77 (2012)). Thus, the invention includes compounds of Formula I, stereoisomers, tautomers, pharmaceutically acceptable salts, or hydrates thereof; pharmaceutical compositions comprising one or more of those compounds; and methods of using those compounds or compositions for treating these diseases.

In one embodiment, BET inhibitor compounds of Formula I, stereoisomers, tautomers, pharmaceutically acceptable salts, or hydrates thereof, or compositions comprising one or more of those compounds may be used for treating rheumatoid arthritis (RA) and multiple sclerosis (MS). Strong proprietary data exist for the utility of BET inhibitors in preclinical models of RA and MS. R. Jahagirdar, S. M. et al., "An Orally Bioavailable Small Molecule RVX-297 Significantly Decreases Disease in a Mouse Model of Multiple Sclerosis," *World Congress of Inflammation*, Paris, France (2011). Both RA and MS are characterized by a dysregulation of the IL-6 and IL-17 inflammatory pathways (Kimura, A. and T. Kishimoto, "IL-6: regulator of Treg/Th17 balance,"*Eur J Immunol* 40(7):1830-5 (2010)) and thus would be especially sensitive to BET inhibition. In another embodiment, BET inhibitor compounds of Formula I may be used for treating sepsis and associated afflictions. BET inhibition has been shown to inhibit development of sepsis, in part, by inhibiting IL-6 expression, in preclinical models in both published (Nicodeme, E., et al., "Suppression of inflammation by a synthetic histone mimic," *Nature* 468 (7327):1119-23 (2010)) and proprietary data.

In one embodiment, BET inhibitor compounds of Formula I, stereoisomers, tautomers, pharmaceutically acceptable salts, or hydrates thereof, or compositions comprising one or more of those compounds may be used to treat cancer. Cancers that have an overexpression, translocation, amplification, or rearrangement c-myc or other myc family oncoproteins (MYCN, L-myc) are particularly sensitive to BET inhibition. Delmore, J. E., et al., "BET bromodomain inhibition as a therapeutic strategy to target c-Myc," *Cell* 146(6):904-17 (2010); Mertz, J. A., et al., "Targeting MYC dependence in cancer by inhibiting BET bromodomains," *Proc Natl Acad Sci USA* 108(40):16669-74 (2011). These cancers include, but are not limited to, B-acute lymphocytic leukemia, Burkitt's lymphoma, Diffuse large cell lymphoma, Multiple myeloma, Primary plasma cell leukemia, Atypical carcinoid lung cancer, Bladder cancer, Breast cancer, Cervix cancer, Colon cancer, Gastric cancer, Glioblastoma, Hepatocellular carcinoma, Large cell neuroendocrine carcinoma, Medulloblastoma, Melanoma, nodular, Melanoma, superficial spreading, Neuroblastoma, esophageal squamous cell carcinoma, Osteosarcoma, Ovarian cancer, Prostate cancer, Renal clear cell carcinoma, Retinoblastoma, Rhabdomyosarcoma, and Small cell lung carcinoma. Vita, M. and M. Henriksson, "The Myc oncoprotein as a therapeutic target for human cancer," *Semin Cancer Biol* 16(4): 318-30 (2006).

In one embodiment, BET inhibitor compounds of Formula I, stereoisomers, tautomers, pharmaceutically acceptable salts, or hydrates thereof, or compositions comprising one or more of those compounds may be used to treat cancers that result from an aberrant regulation (overexpression, translocation, etc) of BET proteins. These include, but are not limited to, NUT midline carcinoma (Brd3 or Brd4 translocation to nutlin 1 gene) (French, C. A., "NUT midline carcinoma," *Cancer Genet Cytogenet* 203(1):16-20 (2010)), B-cell lymphoma (Brd2 overexpression) (Greenwald, R. J., et al., "E mu-BRD2 transgenic mice develop B-cell lymphoma and leukemia,". *Blood* 103(4):1475-84 (2004)), nonsmall cell lung cancer (BrdT overexpression) (Grunwald, C., et al., "Expression of multiple epigenetically regulated cancer/germline genes in nonsmall cell lung cancer," *Int J Cancer* 118(10):2522-8 (2006)), esophageal cancer and head and neck squamous cell carcinoma (BrdT overexpression) (Scanlan, M. J., et al., "Expression of cancer-testis antigens in lung cancer: definition of bromodomain testis-specific gene (BRDT) as a new CT gene, CT9,*"Cancer Lett* 150(2):55-64 (2000)), and colon cancer (Brd4) (Rodriguez, R. M., et al., "Aberrant epigenetic regulation of bromodomain BRD4 in human colon cancer," *J Mol Med* (Berl) 90(5):587-95 (2012)).

In one embodiment, because BET inhibitors decrease Brd-dependent recruitment of pTEFb to genes involved in cell proliferation, BET inhibitor compounds of Formula I, stereoisomers, tautomers, pharmaceutically acceptable salts, or hydrates thereof, or compositions comprising one or more of those compounds may be used to treat cancers that rely on pTEFb (Cdk9/cyclin T) and BET proteins to regulate oncogenes. These cancers include, but are not limited to, chronic lymphocytic leukemia and multiple myeloma (Tong, W. G., et al., "Phase I and pharmacologic study of SNS-032, a potent and selective Cdk2, 7, and 9 inhibitor, in patients with advanced chronic lymphocytic leukemia and multiple myeloma," *J Clin Oncol* 28(18):3015-22 (2010)), follicular lymphoma, diffuse large B cell lymphoma with germinal center phenotype, Burkitt's lymphoma, Hodgkin's lymphoma, follicular lymphomas and activated, anaplastic large cell lymphoma (Bellan, C., et al., "CDK9/CYCLIN T1 expression during normal lymphoid differentiation and malignant transformation," *J Pathol* 203(4):946-52 (2004)), neuroblastoma and primary neuroectodermal tumor (De Falco, G., et al., "Cdk9 regulates neural differentiation and its expression correlates with the differentiation grade of neuroblastoma and PNET tumors," *Cancer Biol Ther* 4(3): 277-81 (2005)), rhabdomyosarcoma (Simone, C. and A. Giordano, "Abrogation of signal-dependent activation of the cdk9/cyclin T2a complex in human RD rhabdomyosarcoma cells," *Cell Death Differ* 14(1):192-5 (2007)), prostate cancer (Lee, D. K., et al., "Androgen receptor interacts with the positive elongation factor P-TEFb and enhances the efficiency of transcriptional elongation," *J Biol Chem* 276(13): 9978-84 (2001)), and breast cancer (Bartholomeeusen, K., et al., "BET bromodomain inhibition activates transcription via a transient release of P-TEFb from 7SK snRNP,"*J Biol Chem* (2012)).

In one embodiment, BET inhibitor compounds of Formula I, stereoisomers, tautomers, pharmaceutically acceptable salts, or hydrates thereof, or compositions comprising one or more of those compounds may be used to treat cancers in which BET-responsive genes, such as CDK6, Bcl2, TYRO3, MYB, and hTERT are up-regulated. Dawson, M. A., et al., "Inhibition of BET recruitment to chromatin as an effective treatment for MLL-fusion leukaemia," *Nature* 478(7370):529-33 (2011); Delmore, J. E., et al., "BET bromodomain inhibition as a therapeutic strategy to target c-Myc," *Cell* 146(6):904-17 (2010). These cancers include, but are not limited to, pancreatic cancer, breast cancer, colon cancer, glioblastoma, adenoid cystic carcinoma, T-cell prolymphocytic leukemia, malignant glioma, bladder cancer, medulloblastoma, thyroid cancer, melanoma, multiple myeloma, Barret's adenocarcinoma, hepatoma, prostate cancer, pro-myelocytic leukemia, chronic lymphocytic leukemia, mantle cell lymphoma, diffuse large B-cell lymphoma, small cell lung cancer, and renal carcinoma. Ruden, M. and N. Puri, "Novel anticancer therapeutics targeting telomerase," *Cancer Treat Rev* (2012); Kelly, P. N. and A. Strasser, "The role of Bcl-2 and its pro-survival relatives in tumourigenesis and cancer therapy" *Cell Death Differ* 18(9): 1414-24 (2011); Uchida, T., et al., "Antitumor effect of bcl-2 antisense phosphorothioate oligodeoxynucleotides on human renal-cell carcinoma cells in vitro and in mice," *Mol Urol* 5(2):71-8 (2001).

Published and proprietary data have shown direct effects of BET inhibition on cell proliferation in various cancers. In one embodiment, BET inhibitor compounds of Formula I, stereoisomers, tautomers, pharmaceutically acceptable salts, or hydrates thereof, or compositions comprising one or more of those compounds may be used to treat cancers for which exist published and, for some, proprietary, in vivo and/or in vitro data showing a direct effect of BET inhibition on cell proliferation. These cancers include NMC (NUT-midline carcinoma), acute myeloid leukemia (AML), acute B lymphoblastic leukemia (B-ALL), Burkitt's Lymphoma, B-cell Lymphoma Melanoma, mixed lineage leukemia, multiple myeloma, pro-myelocytic leukemia (PML), and non-Hodgkin's lymphoma. Filippakopoulos, P., et al., "Selective inhibition of BET bromodomains," *Nature* 468(7327):1067-73 (2010); Dawson, M. A., et al., "Inhibition of BET recruitment to chromatin as an effective treatment for MLL-fusion leukaemia," *Nature* 478(7370):529-33 (2011); Zuber, J., et al., "RNAi screen identifies Brd4 as a therapeutic target in acute myeloid leukaemia," *Nature* 478(7370):524-8 (2011); Miguel F. Segura, et al, "BRD4 is a novel therapeutic target in melanoma," *Cancer Research*. 72(8):Supplement 1 (2012). The compounds of the invention have a demonstrated BET inhibition effect on cell proliferation in vitro for the following cancers: Neuroblastoma, Medulloblastoma, lung carcinoma (NSCLC, SCLC), and colon carcinoma.

In one embodiment, because of potential synergy or additive effects between BET inhibitors and other cancer therapy, BET inhibitor compounds of Formula I, stereoisomers, tautomers, pharmaceutically acceptable salts, or hydrates thereof, or compositions comprising one or more of those compounds may be combined with other therapies, chemotherapeutic agents, or anti-proliferative agents to treat human cancer and other proliferative disorders. The list of therapeutic agents which can be combined with BET inhibitors in cancer treatment includes, but is not limited to, ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

In one embodiment, BET inhibitor compounds of Formula I, stereoisomers, tautomers, pharmaceutically acceptable salts, or hydrates thereof, or compositions comprising one or more of those compounds may be used to treat benign proliferative and fibrotic disorders, including benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, juvenile polyposis syndrome, idiopathic pulmonary fibrosis, renal fibrosis, and post-operative stricture, keloid formation, scleroderma, and cardiac fibrosis. Tang, X et al., "Assessment of Brd4 Inhibition in Idiopathic Pulmonary Fibrosis Lung Fibroblasts and in Vivo Models of Lung Fibrosis,". Am J Pathology in press (2013).

In one embodiment, because of their ability to up-regulate ApoA-1 transcription and protein expression (Mirguet, O., et al., "From ApoA1 upregulation to BET family bromodomain inhibition: discovery of I-BET151," *Bioorg Med Chem Lett* 22(8):2963-7 (2012); Chung, C. W., et al., "Discovery and characterization of small molecule inhibitors of the BET family bromodomains," *J Med Chem* 54(11):3827-38 (2011)), BET inhibitor compounds of Formula I, stereoisomers, tautomers, pharmaceutically acceptable salts, or hydrates thereof, or compositions comprising one or more of those compounds may be used to treat cardiovascular diseases that are generally associated with including dyslipidemia, atherosclerosis, hypercholesterolemia, and metabolic syndrome (Belkina, A. C. and G. V. Denis, "BET domain co-regulators in obesity, inflammation and cancer," *Nat Rev Cancer* 12(7):465-77 (2012); Denis, G. V., "Bromodomain coactivators in cancer, obesity, type 2 diabetes, and inflammation," *Discov Med* 10(55):489-99 (2010)). In another embodiment, BET inhibitor compounds of Formula I may be used to treat non-cardiovascular disease characterized by deficits in ApoA-1, including Alzheimer's disease. Elliott, D. A., et al., "Apolipoproteins in the brain: implications for neurological and psychiatric disorders," *Clin Lipidol* 51(4): 555-573 (2010).

In one embodiment, BET inhibitor compounds of Formula I, stereoisomers, tautomers, pharmaceutically acceptable salts, or hydrates thereof, or compositions comprising one or more of those compounds may be used in patients with insulin resistance and type II diabetes. Belkina, A. C. and G. V. Denis, "BET domain co-regulators in obesity, inflammation and cancer," *Nat Rev Cancer* 12(7):465-77 (2012); Denis, G. V., "Bromodomain coactivators in cancer, obesity, type 2 diabetes, and inflammation," *Discov Med* 10(55):489-99 (2010); Wang, F., et al., "Brd2 disruption in mice causes severe obesity without Type 2 diabetes," *Biochem J* 425(1):71-83 (2010); Denis, G. V., et al, "An emerging role for bromodomain-containing proteins in chromatin regulation and transcriptional control of adipogenesis," *FEBS Lett* 584(15):3260-8 (2010). The anti-inflammatory effects of BET inhibition would have additional value in decreasing inflammation associated with diabetes and metabolic disease. Alexandraki, K., et al., "Inflammatory process in type 2 diabetes: The role of cytokines," *Ann N Y Acad Sci* 1084:89-117 (2006).

In one embodiment, because of their ability to downregulate viral promoters, BET inhibitor compounds of Formula I, stereoisomers, tautomers, pharmaceutically acceptable salts, or hydrates thereof, or compositions comprising one or more of those compounds may be used as therapeutics for cancers that are associated with viruses including Epstein-Barr Virus (EBV), hepatitis virus (HBV, HCV), Kaposi's sarcoma associated virus (KSHV), human papilloma virus (HPV), Merkel cell polyomavirus, and human cytomegalovirus (CMV). Gagnon, D., et al., "Proteasomal degradation of the papillomavirus E2 protein is inhibited by overexpression of bromodomain-containing protein 4," *J Virol* 83(9):4127-39 (2009); You, J., et al., "Kaposi's sarcoma-associated herpesvirus latency-associated nuclear antigen interacts with bromodomain protein Brd4 on host mitotic chromosomes," *J Virol* 80(18):8909-19 (2006); Palermo, R. D., et al., "RNA polymerase II stalling promotes nucleosome occlusion and pTEFb recruitment to drive immortalization by Epstein-Barr virus," *PLoS Pathog* 7(10): e1002334 (2011); Poreba, E., et al., "Epigenetic mechanisms in virus-induced tumorigenesis," *Clin Epigenetics* 2(2):233-47. 2011. In another embodiment, because of their ability to reactivate HIV-1 in models of latent T cell infection and latent monocyte infection, BET inhibitors could be used in combination with anti-retroviral therapeutics for treating HIV. Zhu, J., et al., "Reactivation of Latent HIV-1 by Inhibition of BRD4," *Cell Rep* (2012); Banerjee, C., et al., "BET bromodomain inhibition as a novel strategy for reactivation of HIV-1," *J Leukoc Biol* (2012); Bartholomeeusen, K., et al., "BET bromodomain inhibition activates transcription via a transient release of P-TEFb from 7SK snRNP," *J Biol Chem* (2012); Li, Z., et al., "The BET bromodomain inhibitor JQ1 activates HIV latency through antagonizing Brd4 inhibition of Tat-transactivation," *Nucleic Acids Res* (2012.)

In one embodiment, because of the role of epigenetic processes and bromodomain-containing proteins in neurological disorders, BET inhibitor compounds of Formula I, stereoisomers, tautomers, pharmaceutically acceptable salts, or hydrates thereof, or compositions comprising one or more of those compounds may be used to treat diseases including, but not limited to, Alzheimer's disease, Parkinson's disease, Huntington disease, bipolar disorder, schizophrenia, Rubinstein-Taybi syndrome, and epilepsy. Prinjha, R. K., J. Witherington, and K. Lee, "Place your BETs: the therapeutic potential of bromodomains," *Trends Pharmacol Sci* 33(3): 146-53 (2012); Muller, S., et al., "Bromodomains as therapeutic targets," *Expert Rev Mol Med* 13:e29 (2011).

In one embodiment, because of the effect of BRDT depletion or inhibition on spermatid development, BET inhibitor compounds of Formula I, stereoisomers, tautomers, pharmaceutically acceptable salts, or hydrates thereof, or compositions comprising one or more of those compounds may be used as reversible, male contraceptive agents. Matzuk, M. M., et al., "Small-Molecule Inhibition of BRDT for Male Contraception," *Cell* 150(4): p. 673-684 (2012); Berkovits, B. D., et al., "The testis-specific double bromodomain-containing protein BRDT forms a complex with multiple spliceosome components and is required for mRNA splicing and 3'-UTR truncation in round spermatids," *Nucleic Acids Res* 40(15):7162-75 (2012).

Pharmaceutical Compositions

Pharmaceutical compositions of the present disclosure comprise at least one compound of Formula I, or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula I or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula I or tautomers, stereoisomers, pharmaceutically acceptable salts, and hydrates thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 μg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer. Chemother. Reports* 50(4):219-244 (1966) and the following Table for Equivalent Surface Area Dosage Factors).

Equivalent Surface Area Dosage Factors:

|  | To: | | | | |
|---|---|---|---|---|---|
| From: | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

In one embodiment, a compound of Formula I or a tautomer, stereoisomer, pharmaceutically acceptable salt or hydrate thereof, is administered in combination with another therapeutic agent. The other therapeutic agent can provide additive or synergistic value relative to the administration of a compound of the present disclosure alone. The therapeutic agent can be, for example, a statin; a PPAR agonist, e.g., a thiazolidinedione or fibrate; a niacin, a RVX, FXR or LXR agonist; a bile-acid reuptake inhibitor; a cholesterol absorption inhibitor; a cholesterol synthesis inhibitor; a cholesteryl ester transfer protein (CETP), an ion-exchange resin; an antioxidant; an inhibitor of AcylCoA cholesterol acyltransferase (ACAT inhibitor); a tyrophostine; a sulfonylurea-based drug; a biguanide; an alpha-glucosidase inhibitor; an apolipoprotein E regulator; a HMG-CoA reductase inhibitor, a microsomal triglyceride transfer protein; an LDL-lowing drug; an HDL-raising drug; an HDL enhancer; a regulator of the apolipoprotein A-IV and/or apolipoprotein genes; or any cardiovascular drug.

In another embodiment, a compound of Formula I or a tautomer, stereoisomer, pharmaceutically acceptable salt or hydrate thereof, is administered in combination with one or more anti-inflammatory agents. Anti-inflammatory agents can include immunosuppressants, TNF inhibitors, corticosteroids, non-steroidal anti-inflammatory drugs (NSAIDs), disease-modifying anti-rheumatic drugs (DMARDS), and the like. Exemplary anti-inflammatory agents include, for example, prednisone; methylprenisolone (Medrol®), triamcinolone, methotrexate (Rheumatrex®, Trexall®), hydroxychloroquine (Plaquenil®), sulfasalzine (Azulfidine®), leflunomide (Arava®), etanercept (Enbrel®), infliximab (Remicade®), adalimumab (Humira®), rituximab (Rituxan®), abatacept (Orencia®), interleukin-1, anakinra (Kineret™), ibuprofen, ketoprofen, fenoprofen, naproxen, aspirin, acetominophen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine, or sulfasalazine.

EXAMPLES

General Methods.

Unless otherwise noted, reagents and solvents were used as received from commercial suppliers. Proton nuclear magnetic resonance spectra were obtained on a Bruker AVANCE 300 spectrometer at 300 MHz or Bruker AVANCE 500 spectrometer at 500 MHz. Spectra are given in ppm (δ) and coupling constants, J values, are reported in hertz (Hz). Tetramethylsilane was used as an internal standard for $^1$H nuclear magnetic resonance. Mass spectra analyses were performed on Waters Aquity UPLC Mass Spectrometer in ESI or APCI mode when appropriate, Agilent 6130A Mass Spectrometer in ESI, APCI, or MultiMode mode when appropriate or Applied Biosystems API-150EX Spectrometer in ESI or APCI mode when appropriate. Silica gel chromatography were in general performed on a Teledyne

Preparation of 4,6-bis(3,5-dimethylisoxazol-4-yl)-1H-benzo[d]imidazol-2(3H)-one (Example Compound 1)

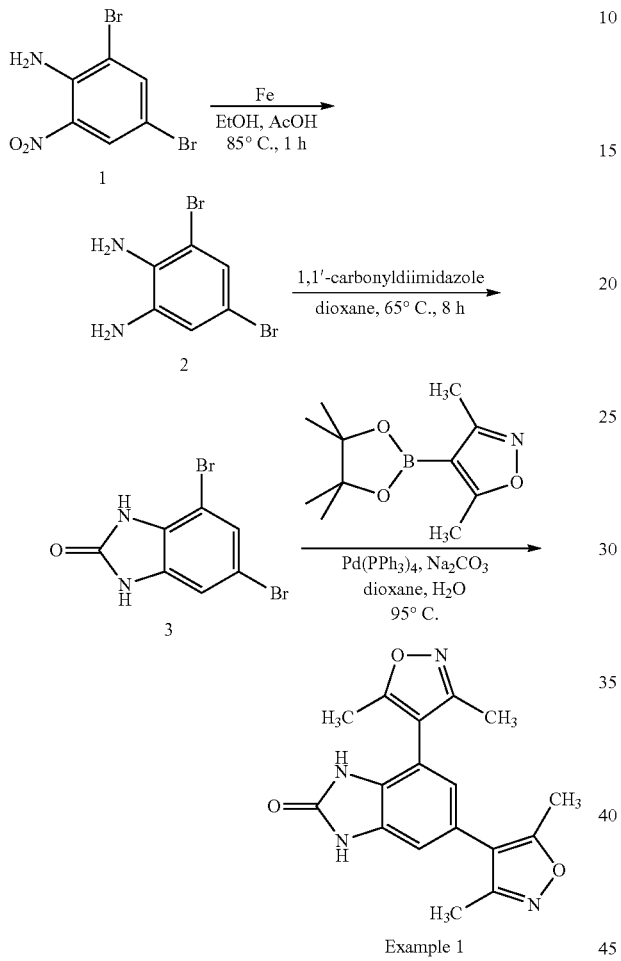

Example 1

Step 1:
To a solution of 1 (5.0 g, 16.9 mmol) in ethanol (35 mL) was added iron (4.7 g, 84.5 mmol) and acetic acid (15 mL). The reaction was heated at 85° C. for an hour. The reaction mixture was cooled to room temperature, diluted with methanol (150 mL) and neutralized with sodium carbonate. The organic layer was dried over sodium sulfate, filtered and concentrated. Purification by chromatography (silica gel, 0-20% ethyl acetate/hexanes) afforded 2 (3.15 g, 70%) as a brown solid: $^1$H NMR (300 MHz, DMSO-$d_6$) δ 6.77 (d, J=2.1 Hz, 1H), 6.65 (d, J=2.1 Hz, 1H), 5.17 (s, 2H), 4.77 (s, 2H).

Step 2:
To a solution of 2 (3.15 g, 11.8 mmol) in 1,4-dioxane (50 mL) was added 1,1'-carbonyldiimidazole (2.3 g, 14.2 mmol). The reaction was heated at 65° C. for 8 hours. The reaction mixture was cooled to room temperature and concentrated in vacuo. Purification by chromatography (silica gel, 0-10% methanol/ethyl acetate) and further trituration with methanol afforded 3 (2.9 g, 83%) as a white solid: $^1$H NMR (300 MHz, DMSO-$d_6$) δ 11.26 (s, 1H), 11.08 (s, 1H), 7.32 (d, J=1.8 Hz, 1H), 7.06 (d, J=1.8 Hz, 1H).

Step 3:
To a suspension of 3 (200 mg, 0.69 mmol) in 1,4-dioxane (5 mL) and water (1 mL) was added 3,5-dimethyl-4-(4,4,5,5-tetramethyl-1,3,2-dioxaborolan-2-yl)isoxazole (535 mg, 2.40 mmol), sodium carbonate (290 mg, 2.74 mmol) and tetrakis(triphenylphosphine)palladium (158 mg, 0.14 mmol). The reaction mixture was purged with nitrogen and was heated at 95° C. for 16 h. The mixture was diluted with methylene chloride (30 mL) and washed with brine (2×10 mL). The organic layer was dried over sodium sulfate, filtered and concentrated. Purification by chromatography (silica gel, 0-100% ethyl acetate/hexanes) afforded Example Compound 1 (70 mg, 32%) as a white solid: $^1$H NMR (300 MHz, DMSO-$d_6$) δ 10.85 (s, 1H), 10.72 (s, 1H), 6.91 (s, 1H), 6.83 (d, J=1.5 Hz, 1H), 2.41 (s, 3H), 2.31 (s, 3H), 2.24 (s, 3H), 2.15 (s, 3H); ESI m/z 325 [M+H]$^+$.

Preparation of 5,7-bis(3,5-dimethylisoxazol-4-yl)-1-methyl-1H-benzo[d]imidazol-2(3H)-one (Example Compound 2)

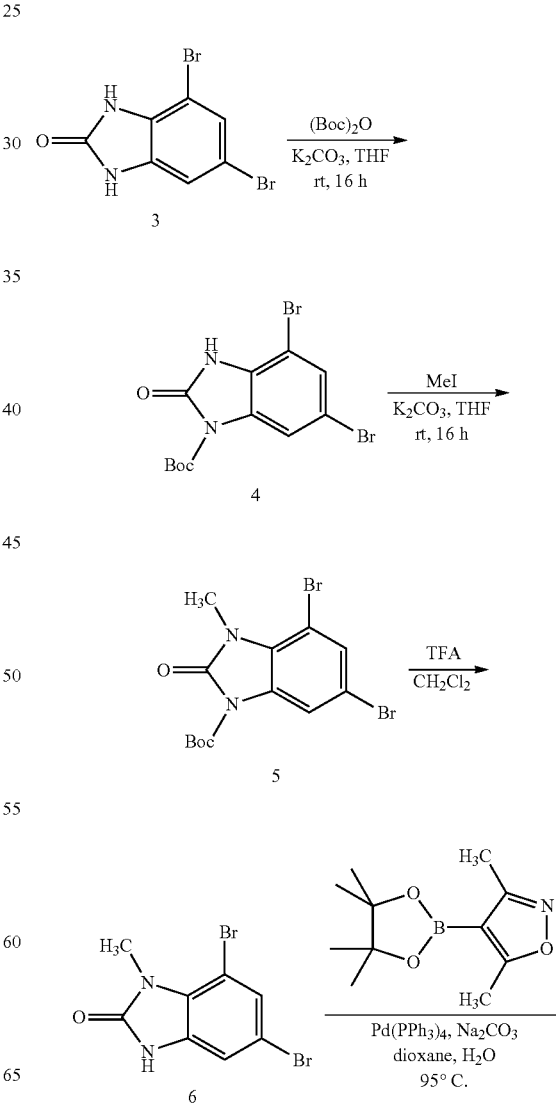

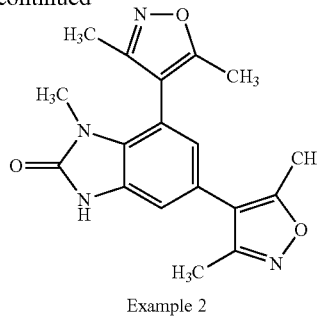

Example 2

Step 1:

To a solution of 3 (400 mg, 1.37 mmol) in tetrahydrofuran (15 mL) was added di-t-butyl dicarbonate (299 mg, 1.37 mmol) and potassium carbonate (189 mg, 1.37 mmol). The reaction was stirred at room temperature for 16 h. The reaction mixture was diluted with ethyl acetate (30 mL) and washed with water and brine. The organic layer was separated, dried over sodium sulfate and concentrated in vacuo to afford 4 (550 mg, >100%) as an off-white solid: $^1$H NMR (300 MHz, DMSO-$d_6$) δ 11.83 (s, 1H), 7.72 (s, 1H), 7.52 (d, J=6.0 Hz, 1H), 1.57 (s, 9H).

Step 2:

To a solution of 4 (550 mg, 1.40 mmol) in tetrahydrofuran (10 mL) was added methyl iodide (0.12 mL, 1.96 mmol) and potassium carbonate (232 mg, 1.68 mmol). The reaction was stirred at room temperature for 16 h. The reaction mixture was diluted with ethyl acetate (30 mL) and washed with sat. sodium bicarbonate and brine. The organic layer was separated, dried over sodium sulfate and concentrated in vacuo to afford 5 (550 mg, 96%) as an off-white solid: $^1$H NMR (300 MHz, DMSO-$d_6$) δ 7.89 (d, J=1.8 Hz, 1H), 7.63 (d, J=1.8 Hz, 1H), 3.56 (s, 3H), 1.58 (s, 9H).

Step 3:

To a solution of 5 (550 mg, 1.40 mmol) in methylene chloride (10 mL) was added trifluoroacetic acid (3.40 mL) and the reaction was stirred at room temperature for 30 min. The reaction mixture was concentrated in vacuo, and the residue was then diluted with ethyl acetate (30 mL), and washed with sat. sodium bicarbonate and brine. The organic layer was separated, dried over sodium sulfate and concentrated in vacuo to afford 6 (440 mg, >100%) as an off-white solid: $^1$H NMR (300 MHz, DMSO-$d_6$) δ 11.37 (bs, 1H), 7.32 (d, J=1.8 Hz, 1H), 7.11 (d, J=1.8 Hz, 1H), 3.53 (s, 3H).

Step 4:

To a solution of 6 (430 mg, 1.41 mmol) in 1,4-dioxane (13 mL) and water (3 mL) was added 3,5-dimethyl-4-(4,4,5,5-tetramethyl-1,3,2-dioxaborolan-2-yl)isoxazole (1.1 g, 4.92 mmol), sodium carbonate (598 mg, 5.64 mmol) and tetrakis(triphenylphosphine)palladium (0) (163 mg, 0.14 mmol). The reaction mixture was purged with nitrogen and then heated at 95° C. for 16 h. The mixture was diluted with methylene chloride (50 mL) and washed with brine (2×10 mL). The organic layer was dried over sodium sulfate, filtered and concentrated. Purification by chromatography (silica gel, 0-50% ethyl acetate/methylene chloride) afforded Example Compound 2 (220 mg, 46%) as a white solid: $^1$H NMR (300 MHz, DMSO-$d_6$) δ 11.17 (s, 1H), 7.01 (d, J=1.8 Hz, 1H), 6.79 (d, J=1.8 Hz, 1H), 2.95 (s, 3H), 2.49 (s, 3H), 2.41 (s, 3H), 2.23 (s, 3H), 2.10 (s, 3H); ESI m/z 339 [M+H]$^+$.

Preparation of 5,7-bis(3,5-dimethylisoxazol-4-yl)benzo[d]oxazol-2(3H)-one (Example Compound 3)

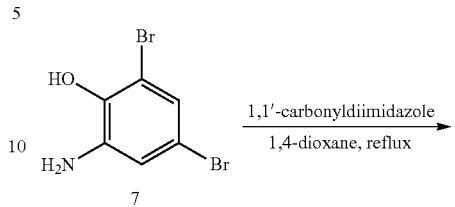

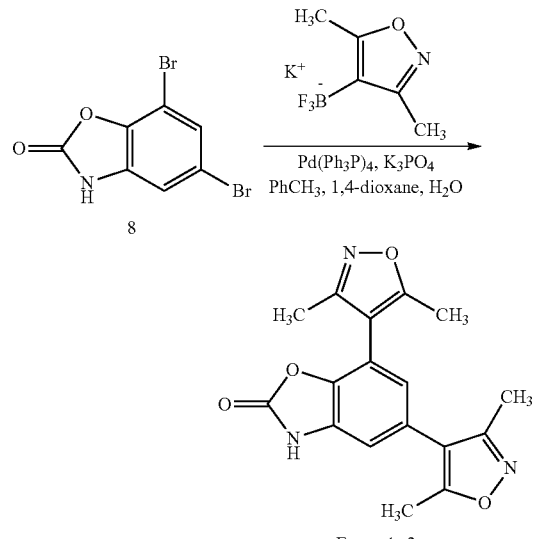

Example 3

Step 1:

A solution of 7 (1.73 g, 6.48 mmol) and 1,1'-carbonyldiimidazole (2.63 g, 16.23 mmol) in 1,4-dioxane (60 mL) was refluxed for 16 h. After cooling to room temperature, the reaction mixture was mixed with silica gel (10 g) and concentrated. The resulting residue was purified by chromatography (silica gel, 0-50% ethyl acetate/heptane) to afford 8 (1.62 g, 85%) as a light brown solid: $^1$H NMR (300 MHz, DMSO-$d_6$) δ 12.16 (br s, 1H), 7.53 (d, J=1.8 Hz, 1H), 7.29 (d, J=1.8 Hz, 1H); MM m/z 292 [M+H]$^+$.

Step 2:

A mixture of 8 (322 mg, 1.10 mmol), potassium (3,5-dimethylisoxazol-4-yl)trifluoroborate (782 mg, 3.85 mmol), potassium phosphate (1.05 g, 4.95 mmol) and tetrakis(triphenylphosphine)palladium(0) (153 mg, 0.13 mmol) in toluene (15 mL)/water (0.5 mL) was purged with nitrogen for 5 minutes. Then the reaction mixture was heated for 16 h at 90° C. After cooling to room temperature, potassium (3,5-dimethylisoxazol-4-yl)trifluoroborate (220 mg, 1.08 mmol), tetrakis(triphenylphosphine)palladium(0) (50 mg, 0.043 mmol), 1,4-dioxane (3 mL)/water (2 mL) were added. The reaction mixture was purged with nitrogen for two minutes, and then heated for 16 h at 90° C. After cooling to room temperature, the reaction mixture was concentrated. The resulting residue was purified by chromatography (silica gel, 0-50% ethyl acetate/heptane) followed by trituration with methylene chloride/hexanes to afford Example Compound 3 (45 mg, 13%) as a white solid: $^1$H NMR (300 MHz, DMSO-$d_6$) δ 11.90 (br s, 1H), 7.15-7.08 (m, 2H), 2.43 (s, 3H), 2.41 (s, 3H), 2.26 (s, 3H), 2.24 (s, 3H); MM m/z 324 [M−H]$^-$.

General Procedure A: 5-(3,5-dimethylisoxazol-4-yl)-1-methyl-7-(2-methylpyridin-3-yl)-1H-benzo[d]imidazol-2(3H)-one (Example Compound 4)

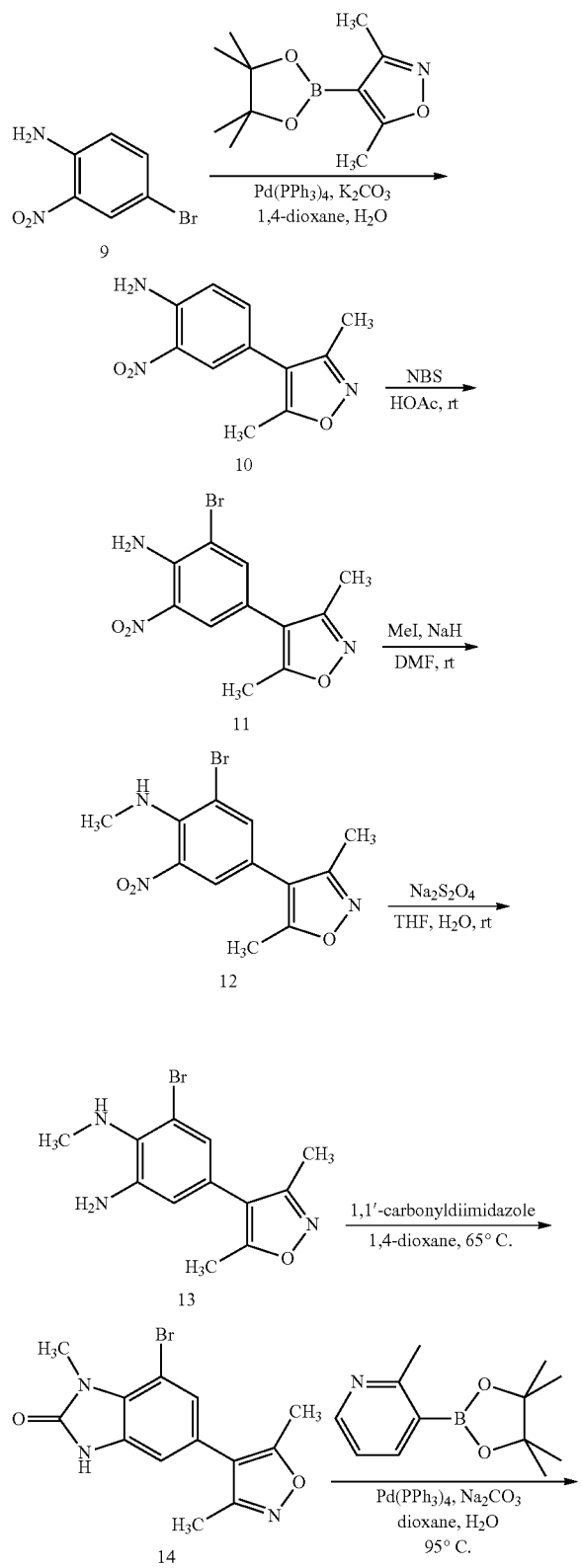

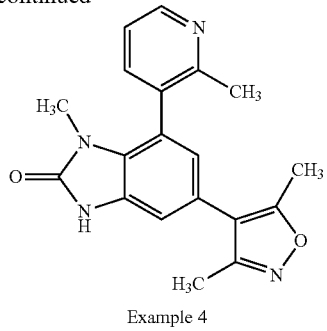

Example 4

Step 1:

To a solution of 9 (1.00 g, 4.61 mmol) in 1,4-dioxane (40 mL) and water (4 mL) was added 3,5-dimethyl-4-(4,4,5,5-tetramethyl-1,3,2-dioxaborolan-2-yl)isoxazole (1.23 g, 5.53 mmol), potassium carbonate (1.27 g, 9.22 mmol), and tetrakis(triphenylphosphine)palladium(0) (266 mg, 0.231 mmol). The reaction mixture was purged with nitrogen and heated at 90° C. for 16 h. The reaction mixture was cooled to room temperature, concentrated and purified by chromatography (silica gel, 0-30% ethyl acetate/hexanes) to give 10 (950 mg, 88%) as a yellow solid: $^1$H NMR (500 MHz, CDCl$_3$) δ 8.02 (d, J=2.1 Hz, 1H), 7.26 (dd, J=2.1 Hz, 8.5 Hz, 1H), 6.89 (d, J=8.6 Hz, 1H), 6.14 (s, 2H), 2.40 (s, 3H), 2.26 (s, 3H); ESI m/z 234 [M+H]$^+$.

Step 2:

To a solution of 10 (940 mg, 4.03 mmol) in acetic acid (15 mL) at 0° C. was added N-bromosuccinimide (753 mg, 4.23 mmol). The reaction was warmed to room temperature and stirred for 16 h. The mixture was concentrated in vacuo. The residue was suspended in hot MeOH, cooled to room temperature and was basified with 10% aq. NaHCO$_3$. The mixture was diluted with water and filtered. The solid was washed with water and dried in vacuo to afford 11 (1.10 g, 87%) as a yellow solid: $^1$H NMR (500 MHz, CDCl$_3$) δ 8.04 (d, J=2.1 Hz, 1H), 7.61 (d, J=2.1 Hz, 1H), 6.69 (br.s, 2H), 2.40 (s, 3H), 2.26 (s, 3H); ESI m/z 312 [M+H]$^+$.

Step 3:

To a solution of 11 (1.00 g, 3.21 mmol) in DMF (10 mL) was added NaH (60% dispersion in mineral oil, 141 mg, 3.53 mmol) at room temperature under nitrogen. The mixture was stirred at room temperature for 30 min and iodomethane (410 mg, 2.98 mmol) was added. The reaction mixture was stirred at room temperature for 16 h. NH$_4$Cl/H$_2$O (10 mL) was added, the mixture was stirred for 30 min, concentrated and purified by chromatography (silica gel, 0-25% ethyl acetate/hexanes) to give 12 (370 mg, 35%) as an orange solid: $^1$H NMR (500 MHz, CDCl$_3$) δ 7.75 (d, J=2.1 Hz, 1H), 7.57 (d, J=2.1 Hz, 1H), 6.25 (q, J=5.6 Hz, 1H), 3.06 (d, J=5.5 Hz, 3H), 2.40 (s, 3H), 2.26 (s, 3H).

Step 4:

To a solution of 12 (2.43 g, 7.45 mmol) in tetrahydrofuran (40 mL) was added sodium dithionite (7.78 g, 44.7 mmol) in water (40 mL). The reaction mixture was stirred at room temperature for 2 h and concentrated under vacuum. To the residue was added 2N HCl (30 mL), the mixture was heated to reflux for 1 min, and concentrated under vacuum. The residue was dissolved in MeOH, adjusted to pH 8 by saturated NaHCO$_3$ (10% in water) and concentrated under vacuum. The residue was purified by chromatography (silica gel, 0-100% ethyl acetate/hexanes) to afford 13 (1.92 g, 87%) as a yellow solid: $^1$H NMR (500 MHz, CDCl$_3$) δ 6.79

(d, J=1.8 Hz, 1H), 6.50 (d, J=1.8 Hz, 1H), 4.08 (br.s, 2H), 3.29 (br.s, 1H), 2.71 (s, 3H), 2.38 (s, 3H), 2.25 (s, 3H); ESI m/z 296 [M+H]$^+$.

Step 5:

To a mixture of 13 (1.92 g, 6.49 mmol) in 1,4-dioxane (50 mL) was added 1,1'-carbonyldiimidazole (2.10 g, 12.9 mmol) and DMAP (10 mg). The reaction was heated in a sealed tube at 100° C. for 16 h. The mixture was concentrated and purified by chromatography (silica gel, 0-100% ethyl acetate in hexanes) to afford 14 (2.03 g, 97%) as a yellow solid: $^1$H NMR (500 MHz, CDCl$_3$) δ 9.28 (s, 1H), 7.08 (d, J=1.4 Hz, 1H), 6.89 (d, J=1.4 Hz, 1H), 3.78 (s, 3H), 2.39 (s, 3H), 2.25 (s, 3H); ESI m/z 322 [M+H]$^+$.

Step 6:

To a solution of 14 (100 mg, 0.31 mmol) in 1,4-dioxane (3 mL) and water (0.5 mL) was added 2-methyl-3-(4,4,5,5-tetramethyl-1,3,2-dioxaborolan-2-yl)pyridine (88 mg, 0.40 mmol), sodium carbonate (66 mg, 0.62 mmol) and tetrakis(triphenylphosphine)palladium (0) (18 mg, 0.016 mmol). The reaction mixture was purged with nitrogen and then heated at 95° C. for 16 h. The mixture was diluted with methylene chloride (50 mL) and washed with brine (2×10 mL). The organic layer was dried over sodium sulfate, filtered and concentrated. Purification by chromatography (silica gel, 0-5% methanol/methylene chloride) afforded Example Compound 4 (55 mg, 53%) as a white solid: $^1$H NMR (300 MHz, DMSO-d$_6$) δ 11.17 (s, 1H), 8.54 (dd, J=5.0, 1.7 Hz, 1H), 7.74 (dd, J=7.6, 1.8 Hz, 1H), 7.36-7.29 (m, 1H), 7.00 (d, J=1.8 Hz, 1H), 6.78 (d, J=1.5 Hz, 1H), 2.70 (s, 3H), 2.40 (s, 3H), 2.31 (s, 3H), 2.23 (s, 3H); ESI m/z 335 [M+H]$^+$.

Preparation of 6-(3,5-dimethylisoxazol-4-yl)-4-(1,3,5-trimethyl-1H-pyrazol-4-yl)-1H-benzo[d]imidazol-2(3H)-one (Example Compound 22)

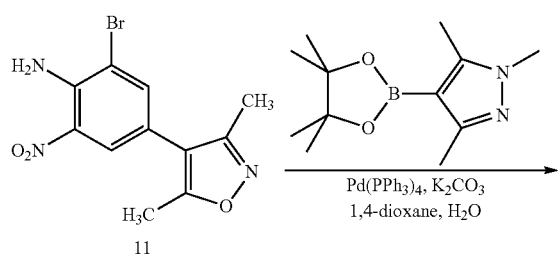

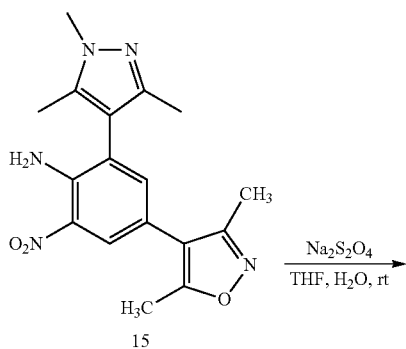

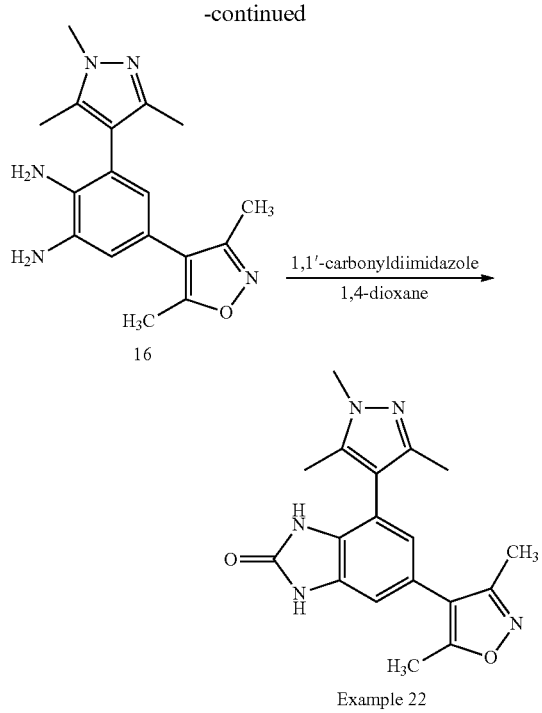

Example 22

Step 1:

To a mixture of 11 (500 mg, 1.6 mmol), 1,3,5-trimethyl-4-(4,4,5,5-tetramethyl-1,3,2-dioxaborolan-2-yl)-1H-pyrazole (454 mg, 1.92 mmol), potassium carbonate (443 mg, 3.20 mmol), water (2 mL) and 1,4-dioxane (9 mL) was added tetrakis(triphenylphosphine)palladium(0) (93 mg, 0.08 mmol). The suspension was heated at 90° C. for 17 h. After cooling to room temperature, methanol (20 mL) and silica gel (10 g) were added. The mixture was concentrated to dryness and the resulting powder was purified by flash chromatography (silica gel, 0-90% ethyl acetate/hexanes) affording 15 as a yellow solid (291 mg, 53%): $^1$H NMR (500 MHz, CDCl$_3$) δ 8.05 (d, J=2.0 Hz, 1H), 7.10 (d, J=2.5 Hz, 1H), 6.26 (br s, 2H), 3.82 (s, 3H), 2.43 (s, 3H), 2.29 (s, 3H), 2.14 (s, 3H), 2.13 (s, 3H).

Step 2:

To a solution of 15 (290 mg, 0.85 mmol) in THF (20 mL) was added a solution of sodium dithionite (887 mg, 5.10 mmol) in water (20 mL). The solution stirred at room temperature for 17 h. The reaction was concentrated to dryness and methanol (30 mL) was added. The suspension stirred at room temperature for 3 h and was filtered. The filtrate was concentrated to dryness and a solution of 2N aq. HCl (20 mL) was added. The solution was brought to reflux for 5 minutes and then cooled to room temperature. The solvent was removed under reduced pressure and silica gel (10 g) and methanol (20 mL) were added. The methanol was removed and the adsorbed silica mixture was subject to flash chromatography (silica gel, 0-50% CMA (CMA: 80% CH$_2$Cl$_2$, 18% methanol, 2% NH$_4$OH) in CH$_2$Cl$_2$) affording 16 as a light brown solid (201 mg, 76%): $^1$H NMR (500 MHz, CDCl$_3$) δ 6.59 (d, J=2.0 Hz, 1H), 6.44 (d, J=2.0 Hz, 1H), 3.80 (s, 3H), 3.48 (br s, 4H), 2.39 (s, 3H), 2.27 (s, 3H), 2.16 (s, 3H), 2.14 (s, 3H).

Step 3:

To a solution of 16 (200 mg, 0.64 mmol) in anhydrous 1,4-dioxane (10 mL) at room temperature was added 1,1'-carbonyldiimidazole (125 mg, 0.77 mmol). The mixture was heated at 65° C. for 17 h and then cooled to room temperature. After adding silica gel (10 g) and concentrating the mixture to dryness, the material was subject to flash chromatography (silica gel, 0-10% methanol in CH$_2$Cl$_2$) and the product fractions were concentrated to an off-white solid. The solid was triturated with ethyl acetate (20 mL) and the suspension was filtered. The solid collected was dried in a vacuum oven for 17 h affording the product Example Compound 22 (197 mg, 91%) as an off-white solid: $^1$H NMR (500 MHz, DMSO-d$_6$) δ 10.7 (s, 1H), 10.4 (s 1H), 6.82 (d, J=1.5 Hz, 1H), 6.68 (d, J=1.5 Hz, 1H), 3.70 (s, 3H), 2.40 (s, 3H), 2.23 (s, 3H), 2.12 (s, 3H), 2.05 (s, 3H); ESI m/z 338 [M+H]$^+$.

General Procedure B: Preparation of 5-(3,5-dimethylisoxazol-4-yl)-1-methyl-7-((1,3,5-trimethyl-1H-pyrazol-4-yl)amino)-1H-benzo[d]imidazol-2(3H)-one (Example Compound 26)

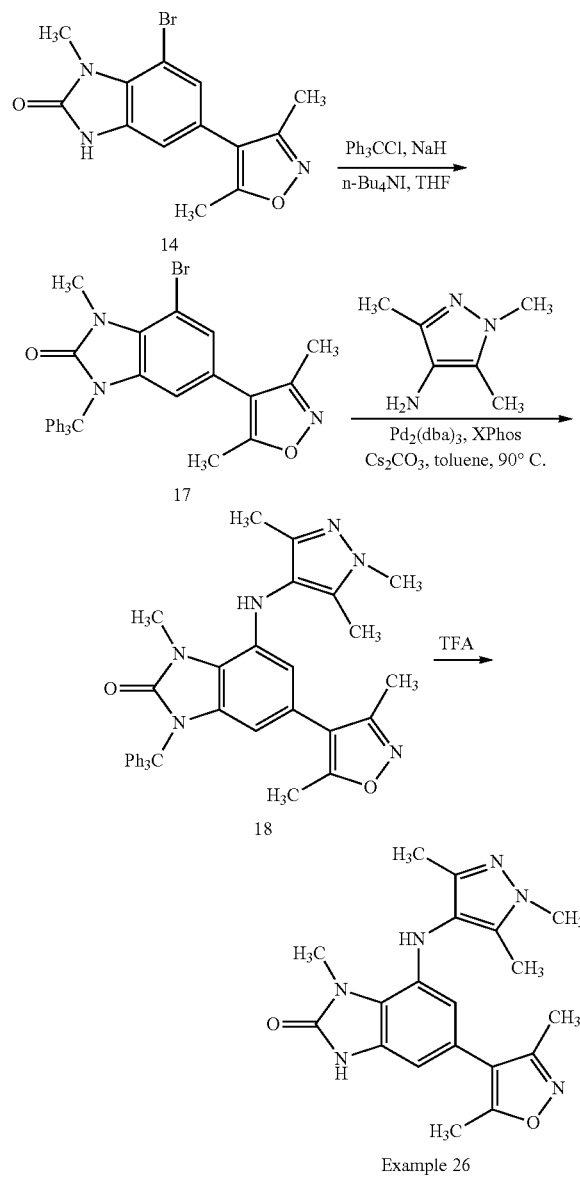

Step 1:

To a solution of 14 (2.03 g, 6.30 mmol) in dichloromethane (100 mL) was added triethylamine (2.63 mL, 18.9 mmol) followed by trityl chloride (5.27 g, 18.9 mmol). The mixture was stirred at room temperature overnight. The mixture was concentrated, the residue was purified by chromatography (silica gel, 0-20% ethyl acetate/hexanes) to give 17 (1.55 g, 44%) as an off-white solid: $^1$H NMR (500 MHz, CD$_3$OD) δ 7.50-7.15 (m, 15H), 7.10 (d, J=1.3 Hz, 1H), 6.16 (d, J=1.3 Hz, 1H), 3.72 (s, 3H), 2.15 (s, 3H), 1.96 (s, 3H); ESI m/z 564 [M+H]$^+$.

Step 2:

To a solution of 17 (200 mg, 0.355 mmol) in toluene (10 mL) under nitrogen atmosphere was added 1,3,5-trimethyl-1H-pyrazol-4-amine (66 mg, 0.53 mmol), cesium carbonate (231 mg, 0.710 mmol), 2-dicyclohexylphosphino-2',4',6'-tri-i-propyl-1,1'-biphenyl (25 mg, 0.053 mmol), and tris(dibenzylideneacetone) dipalladium(0) (33 mg, 0.036 mmol). The reaction mixture was heated at 90° C. overnight, cooled to room temperature, and purified by chromatography (silica gel, 0-100% ethyl acetate/hexanes) to give 18 (140 mg, 67%) as a yellow solid: $^1$H NMR (500 MHz, CD$_3$OD) δ 7.47 (d, J=7.3 Hz, 6H), 7.24 (t, J=6.5 Hz, 6H), 7.18 (t, J=6.5 Hz, 3H), 6.28 (s, 1H), 5.85 (d, J=1.3 Hz, 1H), 5.65 (d, J=1.3 Hz, 1H), 3.71 (s, 3H), 3.70 (s, 3H), 2.10 (s, 3H), 2.03 (s, 3H), 2.00 (s, 3H), 1.84 (s, 3H).

Step 3:

A mixture of 18 (140 mg, 0.236 mmol) and TFA (2 mL) were stirred at room temperature overnight. The reaction mixture was concentrated under vacuum. The residue was dissolved in MeOH and basified using concentrated NH$_4$OH. The mixture was concentrated under vacuum and purified by reverse phase HPLC on Polaris C$_{18}$ column eluted with 10-90% CH$_3$CN in H$_2$O to give Example Compound 26 (24 mg, 28%) as an off-white solid: $^1$H NMR (500 MHz, CD$_3$OD) δ 5.45 (s, 1H), 5.89 (s, 1H), 3.77 (s, 3H), 3.72 (s, 3H), 2.27 (s, 3H), 2.14 (s, 3H), 2.10 (s, 3H), 2.06 (s, 3H); ESI m/z 367 [M+H]$^+$.

Preparation of 5-(3,5-dimethylisoxazol-4-yl)-1-methyl-7-((2-methylpyridin-3-yl)oxy)-1H-benzo[d]imidazol-2(3H)-one (Example Compound 31)

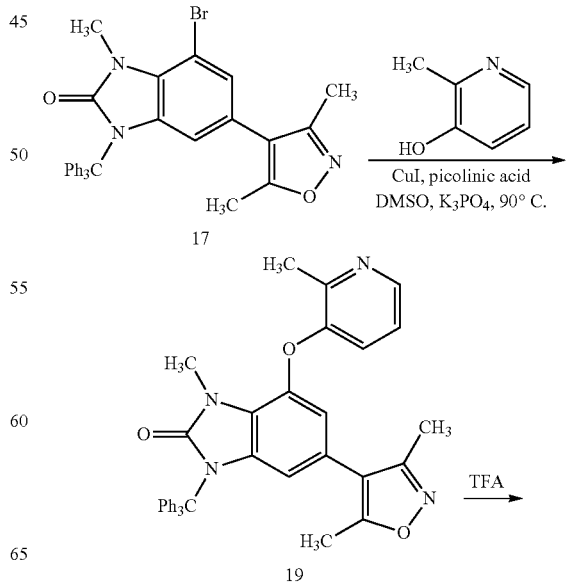

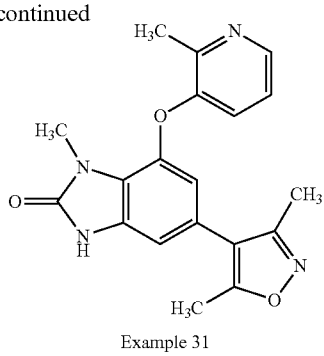

Example 31

Step 1:

To a solution of 17 (200 mg, 0.355 mmol) in DMSO (10 mL) under nitrogen atmosphere was added 2-methylpyridin-3-ol (58 mg, 0.53 mmol), K$_3$PO$_4$ (188 mg, 0.888 mmol), picolinic acid (9 mg, 0.07 mmol), and CuI (7 mg, 0.04 mmol). The reaction mixture was heated at 90° C. overnight, cooled to room temperature, and concentrated under vacuum. The residue was purified by chromatography (silica gel, 0-100% ethyl acetate/hexanes) to give 19 (130 mg, 62%) as a yellow solid: $^1$H NMR (500 MHz, CDCl$_3$) δ 8.30 (dd, J=1.5, 4.5 Hz, 1H), 7.46 (d, J=7.4 Hz, 6H), 7.33-7.20 (m, 9H), 7.18-7.10 (m, 2H), 6.24 (d, J=1.3 Hz, 1H), 5.55 (d, J=1.3 Hz, 1H), 3.51 (s, 3H), 2.58 (s, 3H), 2.05 (s, 3H), 1.91 (s, 3H); ESI m/z 593 [M+H]$^+$.

Step 2:

A mixture of 19 (130 mg, 0.220 mmol) and TFA (2 mL) were stirred at room temperature overnight. The reaction mixture was concentrated under vacuum. The residue was dissolved in MeOH and basified with concentrated NH$_4$OH. The mixture was concentrated under vacuum and purified by reverse phase HPLC on a Polaris C$_{18}$ column eluted with 10-90% CH$_3$CN in H$_2$O to give Example Compound 31 (35 mg, 46%) as an off-white solid: $^1$H NMR (500 MHz, CD$_3$OD) δ 8.21 (dd, J=1.5, 4.6 Hz, 1H), 7.31 (dd, J=1.5, 8.3 Hz, 1H), 7.27 (dd, J=4.6, 8.4 Hz, 1H), 6.87 (d, J=1.4 Hz, 1H), 6.49 (d, J=1.4 Hz, 1H), 3.51 (s, 3H), 2.59 (s, 3H), 2.34 (s, 3H), 2.17 (s, 3H); ESI m/z 351 [M+H]$^+$.

General Procedure C: 5-(5-(hydroxymethyl)-3-methylisoxazol-4-yl)-1-methyl-7-(1,3,5-trimethyl-1H-pyrazol-4-yl)-1H-benzo[d]imidazol-2(3H)-one (Example Compound 28)

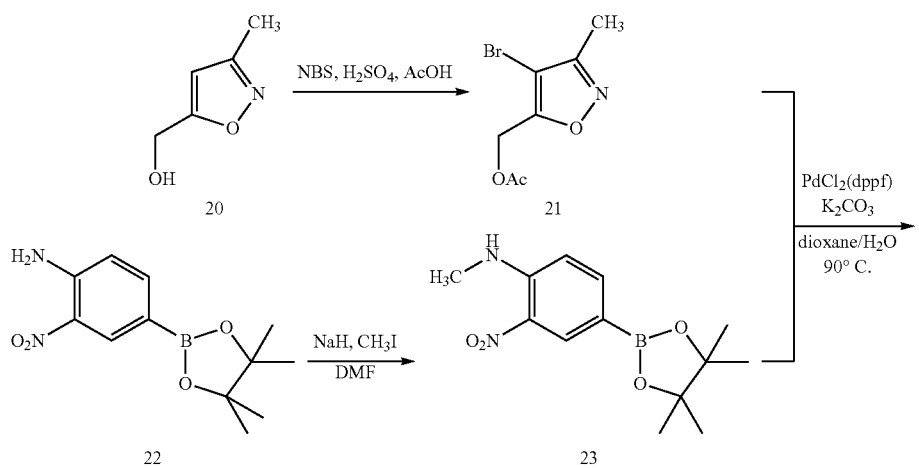

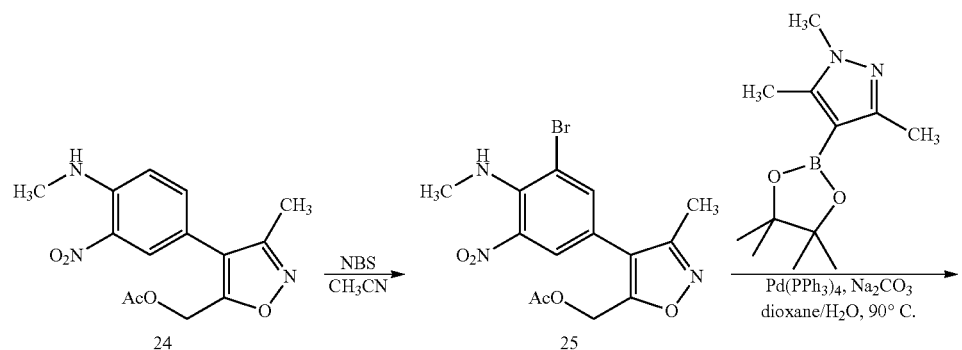

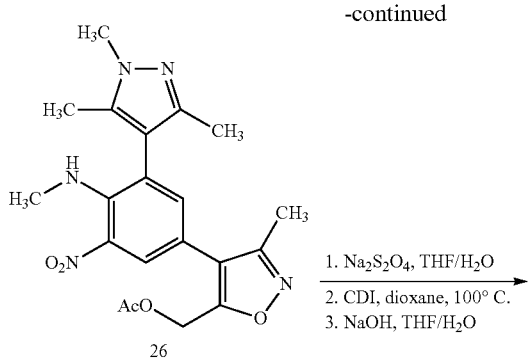

Step 1:

To a solution of 20 (3.20 g, 28.32 mmol) in AcOH (5 mL) was added N-bromosuccinimide (6.05 g, 33.98 mmol) and $H_2SO_4$ (0.1 mL). The reaction mixture was heated to 120° C. for 3 h. The reaction mixture was concentrated, the residue was dissolved in EtOAc (200 mL), washed with saturated $NaHCO_3$ (100 mL), saturated $Na_2S_2O_3$ (3×50 mL) and brine (100 mL). The organic layer was dried over sodium sulfate, filtered and concentrated to give 21 (5.50 g, 83%) as a pale yellow solid: $^1$H NMR (300 MHz, $CDCl_3$) δ 5.16 (s, 2H), 2.31 (s, 3H), 2.13 (s, 3H).

Step 2:

To a solution of 22 (10.0 g, 37.9 mmol) in DMF (100 mL) at 0° C. was added NaH (60%, 1.97 g, 49.3 mmol). The mixture was stirred at 0° C. for 30 minutes, $CH_3I$ (3.54 mL, 56.9 mol) was added dropwise, the mixture was stirred at 0° C. for 1 h, then warmed to room temperature and stirred overnight. The reaction was quenched with saturated $NH_4Cl$ (100 mL) and extracted with EtOAc (3×150 mL). The combined organic layer was washed with brine (3×150 mL), dried over sodium sulfate, filtered and concentrated. The residue was triturated with EtOAc/hexanes to afford 23 (8.5 g, 80%) as an orange solid: $^1$H NMR (300 MHz, DMSO-$d_6$) δ 8.39 (q, J=5.1 Hz, 1H), 8.35 (d, J=1.2 Hz, 1H), 7.72 (dd, J=8.7, 0.9 Hz, 1H), 6.98 (d, J=9.7 Hz, 1H), 2.97 (d, J=4.8 Hz, 3H), 1.29 (s, 12H).

Step 3:

A mixture of 21 (2.34 g, 10.0 mmol), 23 (4.0 g, 14.4 mmol) and potassium carbonate (4.14 g, 30.0 mmol) in 1,4-dioxane (60 mL) and water (10 mL) was purged with nitrogen for 10 minutes, $PdCl_2$(dppf) (817 mg, 1.0 mmol) was then added. The reaction mixture was heated at 90° C. for 7 h, diluted with EtOAc (300 mL), washed with brine (2×100 mL). The organic layer was dried over sodium sulfate, filtered and concentrated. The residue was purified by chromatography (silica gel, 10-50% ethyl acetate/hexanes) to afford 24 (1.15 g, 37%) as an orange gum: $^1$H NMR (300 MHz, DMSO-$d_6$) δ 8.30 (q, J=5.1 Hz, 1H), 8.08 (d, J=2.1 Hz, 1H), 7.62 (dd, J=9.0, 1.8 Hz, 1H), 7.11 (d, J=9.0 Hz, 1H), 5.14 (s, 2H), 3.00 (d, J=4.8 Hz, 3H), 2.26 (s, 3H), 2.05 (s, 3H).

Step 4:

A solution of 24 (1.15 g, 3.77 mmol) in $CH_3CN$ (50 mL) was cooled to 0° C. and N-bromosuccinimide (1.21 g, 6.79 mmol) was added portionwise. The reaction mixture was stirred at 0° C. for 30 minutes, then warmed to rt for 3 h. The reaction mixture was diluted with EtOAc (200 mL), washed with saturated $Na_2S_2O_3$ (3×50 mL) and brine (100 mL). The organic layer was dried over sodium sulfate, filtered and concentrated. The residue was suspended in EtOAc/hexanes (1/1, 100 mL), sonicated and filtered, and the filtrate was concentrated to give 25 (1.31 g, 90%) as an orange solid: $^1$H NMR (300 MHz, DMSO-$d_6$) δ 7.87 (d, J=2.1 Hz, 1H), 7.81 (d, J=2.1 Hz, 1H), 6.55 (q, J=5.1 Hz, 1H), 5.15 (s, 2H), 2.73 (d, J=5.4 Hz, 3H), 2.25 (s, 3H), 2.03 (s, 3H).

Step 5:

A mixture of 25 (95 mg, 0.243 mmol), 1,3,5-trimethyl-4-(4,4,5,5-tetramethyl-1,3,2-dioxaborolan-2-yl)-1H-pyrazole (115 mg, 0.486 mmol) and $Na_2CO_3$ (77 mg, 0.729 mmol) in 1,4-dioxane (5 mL) and water (0.4 mL) was purged with nitrogen for 5 minutes, $Pd(PPh_3)_4$ (28 mg, 0.024 mmol) was added and the reaction mixture was heated at 90° C. for 18 h. The reaction mixture was diluted with EtOAc (30 mL), filtered and concentrated. The residue was purified by chromatography (silica gel, 0-5% methanol/ethyl acetate) to afford 26 (38 mg, 38%) as an orange oil: $^1$H NMR (300 MHz, DMSO-$d_6$) δ 7.91 (d, J=2.4 Hz, 1H), 7.26 (d, J=2.4 Hz, 1H), 6.99 (q, J=5.4 Hz, 1H), 5.17 (s, 2H), 3.71 (s, 3H), 2.45 (d, J=5.4 Hz, 3H), 2.28 (s, 3H), 2.09 (s, 3H), 2.02 (s, 3H), 2.01 (s, 3H).

Step 6:

To a solution of 26 (38 mg, 0.092 mmol) in tetrahydrofuran (5 mL) and water (4 mL) was added sodium dithionite (104 mg, 0.60 mmol). The reaction mixture was stirred at room temperature for 4 h, 2 N HCl (1 mL) was added, the mixture was heated to reflux for 15 minutes then cooled to rt. $Na_2CO_3$ was added slowly to adjust to pH 9. The mixture was extracted with $CH_2Cl_2$ (50 mL), the organic layer was washed with brine (30 mL), filtered and concentrated. The residue was dissolved in 1,4-dioxane (2 mL), 1,1'-carbonyldiimidazole (19 mg, 0.12 mmol) was added and the mixture was heated to 100° C. for 18 h. The mixture was concentrated, the residue was dissolved in THF (3 mL), NaOH (1 N in water, 0.5 mL) was added and the reaction mixture was heated to 50° C. for 2 h. The mixture was diluted with EtOAc (15 mL), washed with brine (3×10 mL). The organic layer was dried over sodium sulfate, filtered and concentrated. The residue was purified by chromatography (silica gel, 0-10% methanol/ethyl acetate) followed by trituration with EtOAc/hexanes to afford Example Compound 28 (9 mg, 24%) as an off-white solid: $^1$H NMR (300 MHz, DMSO-$d_6$) δ 11.08 (s, 1H), 7.03 (d, J=1.5 Hz, 1H), 6.74 (d, J=1.8 Hz, 1H), 5.65 (t, J=5.7 Hz, 1H), 4.49 (d, J=5.7 Hz, 2H), 3.73 (s, 3H), 2.88 (s, 3H), 2.27 (s, 3H), 2.09 (s, 3H), 1.97 (s, 3H); ESI m/z 368 [M+H]$^+$.

Preparation of 4,6-bis(3,5-dimethylisoxazol-4-yl)-1,3-dimethyl-1H-benzo[d]imidazol-2(3H)-one (Example Compound 15)

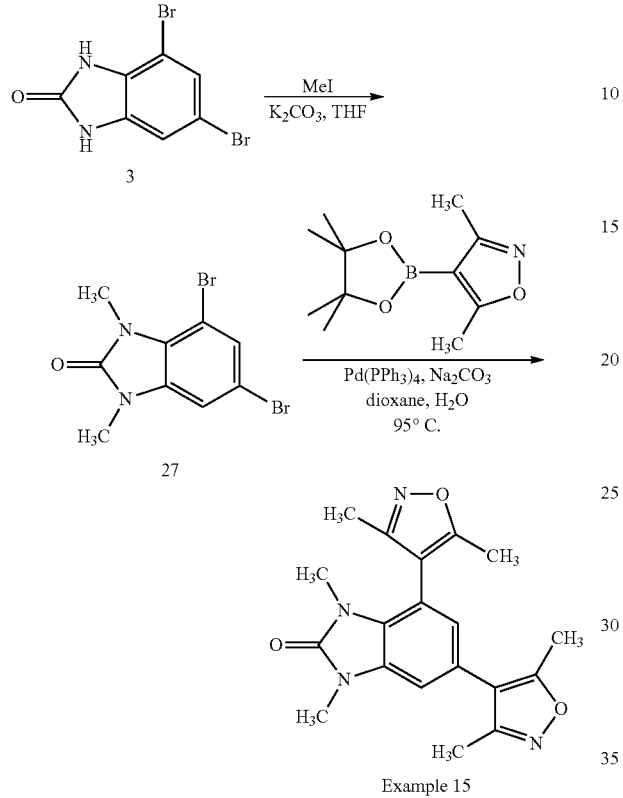

Example 15

Step 1:

To a solution of 3 (300 mg, 1.03 mmol) in tetrahydrofuran (6 mL) was added methyl iodide (0.16 mL, 2.57 mmol) and potassium carbonate (284 mg, 2.06 mmol). The reaction was stirred at room temperature for 16 h. The reaction mixture was diluted with ethyl acetate (30 mL) and washed with sat. sodium bicarbonate and brine. The organic layer was separated, dried over sodium sulfate and concentrated. The residue was triturated with EtOAc to afford 27 (150 mg, 46%) as an off-white solid: ESI m/z 320 [(M+2)+H]$^+$.

Step 2:

To a solution of 27 (150 mg, 0.47 mmol) in 1,4-dioxane (5 mL) and water (1 mL) was added 3,5-dimethyl-4-(4,4,5,5-tetramethyl-1,3,2-dioxaborolan-2-yl)isoxazole (366 mg, 1.64 mmol), sodium carbonate (1998 mg, 1.88 mmol) and tetrakis(triphenylphosphine)palladium (0) (27 mg, 0.024 mmol). The reaction mixture was purged with nitrogen and then heated at 95° C. for 16 h. The mixture was diluted with methylene chloride (50 mL) and washed with brine (2×10 mL). The organic layer was dried over sodium sulfate, filtered and concentrated. Purification by chromatography (silica gel, 0-50% ethyl acetate/methylene chloride) afforded Example Compound 15 (48 mg, 29%) as a white solid: $^1$H NMR (300 MHz, DMSO-$d_6$) δ 7.26 (d, J=1.8 Hz, 1H), 6.84 (d, J=1.8 Hz, 1H), 3.40 (s, 3H), 3.00 (s, 3H), 2.43 (s, 3H), 2.29 (s, 3H), 2.26 (s, 3H), 2.09 (s, 3H); ESI m/z 353 [M+H]$^+$.

General Procedure D: Preparation of 5-(3,5-dimethylisoxazol-4-yl)-1-methyl-7-(3-methylpyridin-4-yl)-1H-benzo[d]imidazol-2(3H)-one (Example Compound 38)

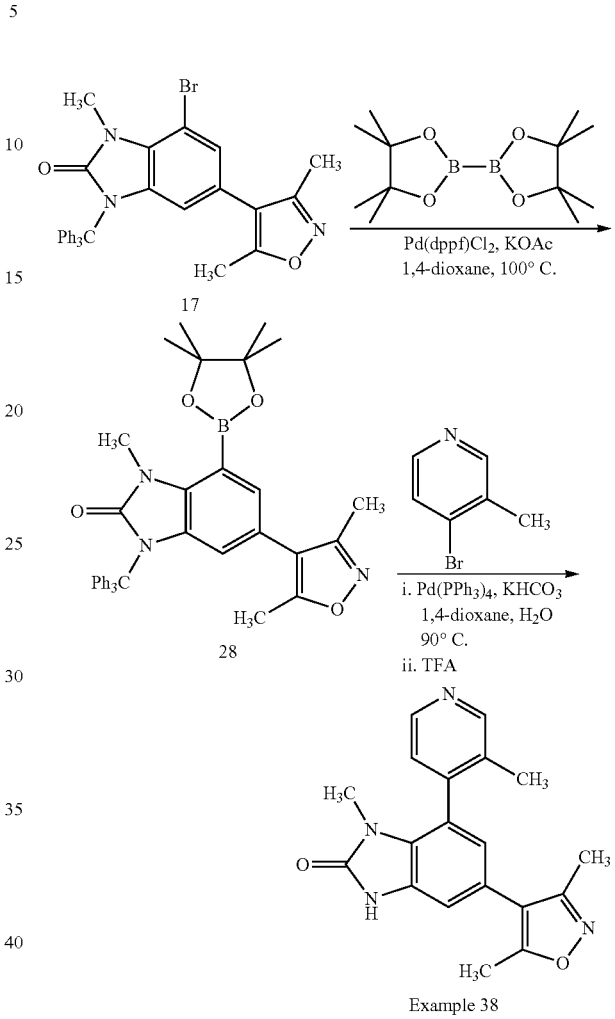

Example 38

Step 1:

To a solution of 17 (500 mg, 0.887 mmol) in 1,4-dioxane (10 mL) was added 4,4,4',4',5,5,5',5'-octamethyl-2,2'-bi(1,3,2-dioxaborolane) (338 mg, 1.33 mmol), potassium acetate (174 mg, 1.77 mmol), and [1,1'-bis(diphenylphosphino)ferrocene] dichloropalladium(II) (65 mg, 0.089 mmol). The reaction mixture was purged with nitrogen for 5 minutes and then heated at 100° C. for 16 h. The reaction mixture was cooled to room temperature, concentrated and purified by chromatography (silica gel, 0-50% ethyl acetate in hexanes) to afford 28 (310 mg, 57%) as a yellow solid: $^1$H NMR (500 MHz, CD$_3$OD) δ 7.50-7.40 (m, 6H), 7.30-7.18 (m, 10H), 6.27 (d, J=1.6 Hz, 1H), 3.51 (s, 3H), 2.13 (s, 3H), 1.95 (s, 3H), 1.39 (s, 12H); ESI m/z 612 [M+H]$^+$.

Step 2:

To a solution of 28 (100 mg, 0.164 mmol) in 1,4-dioxane (10 mL) and water (1 mL) was added 4-bromo-3-methylpyridine (57 mg, 0.33 mmol), potassium bicarbonate (68 mg, 0.49 mmol), and tetrakis(triphenylphosphine)palladium (0) (9 mg, 0.008 mmol). The reaction mixture was purged with nitrogen for 5 minutes and then heated at 90° C. for 16 h. The reaction mixture was cooled to room temperature and concentrated. The residue was dissolved in TFA (2 mL) and stirred at room temperature for 2 h. The mixture was concentrated. The residue was purified by chromatography (silica gel, 0-20% methanol/ethyl acetate). The product was further purified by reverse phase HPLC on a Polaris C$_{18}$ column eluting with 10-90% CH$_3$CN in H$_2$O to give Example Compound 38 (28 mg, 51%) as an off-white solid: $^1$H NMR (500 MHz, CD$_3$OD) δ 8.53 (s, 1H), 8.47 (d, J=4.9 Hz, 1H), 7.42 (d, J=5.0 Hz, 1H), 7.09 (d, J=1.4 Hz, 1H), 6.79 (d, J=1.4 Hz, 1H), 2.88 (s, 3H), 2.41 (s, 3H), 2.25 (s, 3H), 2.19 (s, 3H); ESI m/z 335 [M+H]$^+$.

General Procedure E: Preparation of 3-(6-(3,5-dimethylisoxazol-4-yl)-3-methyl-2-oxo-2,3-dihydro-1H-benzo[d]imidazol-4-yl)-4-methylbenzamide (Example Compound 29)

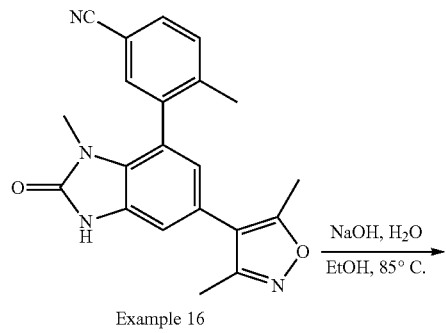

Example 16

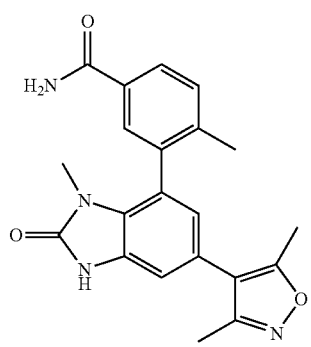

Example 29

To a solution of Example 16 (35 mg, 0.10 mmol) in ethanol (2 mL) was added 2 N NaOH (0.49 mL). The reaction mixture was heated to 85° C. for 2 h. The reaction mixture was diluted in methylene chloride (70 mL), washed with brine (25 mL), dried over sodium sulfate, filtered, and concentrated. The residue was purified by chromatography (silica gel, 0-10% methanol/methylene chloride) to afford Example 29 (34 mg, 92%) as white solid: $^1$H NMR (500 MHz, DMSO-d$_6$) δ 11.11 (br.s, 1H), 7.94 (br.s, 1H), 7.87 (dd, J=7.8, 2.0 Hz, 1H), 7.82 (d, J=2.0 Hz, 1H), 7.42 (d, J=8.0 Hz, 1H), 7.31 (br.s, 1H), 6.99 (d, J=2.0 Hz, 1H), 6.75 (d, J=1.5 Hz, 1H) 2.67 (s, 3H), 2.40 (s, 3H), 2.22 (s, 3H), 2.15 (s, 3H); ESI m/z 377 [M+H]$^+$.

Preparation of 6-(3,5-dimethylisoxazol-4-yl)-4-(1,3,5-trimethyl-1H-pyrazol-4-yl)-1H-benzo[d]imidazole-2(3H)-thione (Example 23)

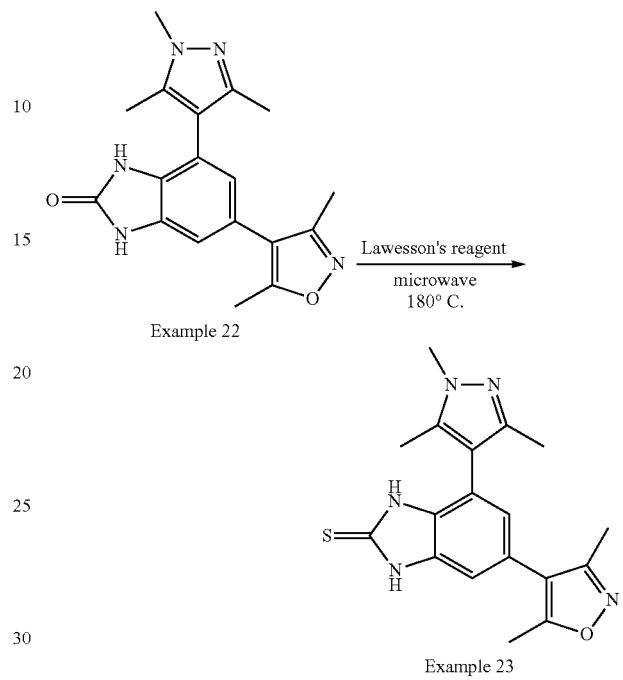

Lawesson's reagent (0.485 g, 1.20 mmol) was added to a solution of Example Compound 22 (0.337 g, 1.00 mmol) in 1,4-dioxane (2 mL). The reaction was stirred at 180° C. for 6 h under microwave heating conditions. The reaction was cooled to rt, concentrated under reduced pressure and quenched with water (75 mL) The resulting precipitate was collected by filtration, washed with water, then ethyl acetate (20 mL) and dried under vacuum. The residue was purified by flash column chromatography (silica gel, 0-5% methanol/dichloromethane) followed by prep. HPLC to afford Example 23 (0.066 g, 19%) as a white solid: $^1$H NMR (400 MHz, DMSO-d$_6$) δ 12.37 (br s, 2H), 7.01 (s, 1H), 6.87 (s, 1H), 3.71 (s, 3H), 2.42 (s, 3H), 2.24 (s, 3H), 2.11 (s, 3H), 2.05 (s, 3H); ESI MS m/z 352 [M−H]$^-$.

Preparation of 6-(3,5-dimethylisoxazol-4-yl)-4-(4-methylpyridin-3-yl)-1H-benzo[d]imidazole-2(3H)-thione (Example Compound 24)

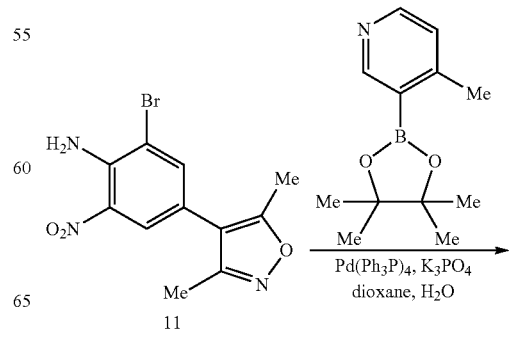

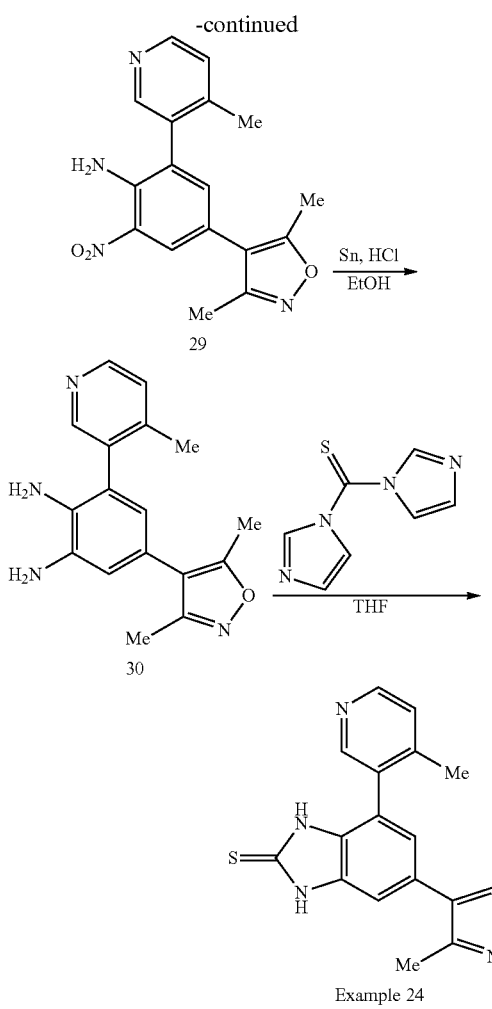

Example 24 time the resulting precipitate was collected by filtration, washed with ethanol (2×50 mL), then Et$_2$O (2×100 mL) and dried under vacuum. The material was dissolved in water (100 mL) and the pH of the resulting solution was adjusted to 9 with solid K$_2$CO$_3$ (4.9 g). The aqueous solution was extracted with chloroform (6×20 mL). The combined organics were dried over MgSO$_4$, filtered and concentrated under reduced pressure to 30 (3.27 g, 80%) as a yellow solid: $^1$H NMR (400 MHz, CDCl$_3$) δ 8.51 (d, J=5.2 Hz, 1H), 8.46 (s, 1H), 7.26 (d, J=5.2 Hz, 1H), 6.66 (d, J=2.0 Hz, 1H), 6.47 (d, J=2.0 Hz, 1H), 3.54 (br.s, 2H), 3.31 (br s, 2H), 2.40 (s, 3H), 2.27 (s, 3H), 2.23 (s, 3H).

Step 3: 1,1'-thiocarbonyldiimidazole (0.267 g, 1.5 mmol) was added in one portion to a stirred suspension of 30 (0.294 g, 1.0 mmol) in anhydrous THF (10 mL). The reaction was heated at reflux with stirring for 21 h. The reaction was cooled to rt and concentrated under reduced pressure. The residue was dissolved in chloroform (20 mL), washed with water (3×10 mL), dried over MgSO$_4$, filtered and concentrated under reduced pressure. The residue was purified by flash column chromatography (silica gel, 0-2% methanol/chloroform) to give Example 2 Compound 4 (0.305 g, 91%) as a yellow solid: $^1$H NMR (400 MHz, CDCl$_3$) δ 12.58 (br.s, 1H), 11.33 (br.s, 1H), 8.45 (s, 1H), 8.23 (d, J=5.4 Hz, 1H), 7.22 (d, J=5.4 Hz, 1H), 7.15 (d, J=1.2 Hz, 1H), 6.91 (d, J=1.2 Hz, 1H), 2.41 (s, 3H), 2.28 (s, 3H), 2.27 (s, 3H); ESI MS m/z 337 [M+H]$^+$.

Preparation of 3-(6-(3,5-dimethylisoxazol-4-yl)-2-thioxo-2,3-dihydro-1H-benzo[d]imidazol-4-yl)-4-methylbenzonitrile (Example Compound 25)

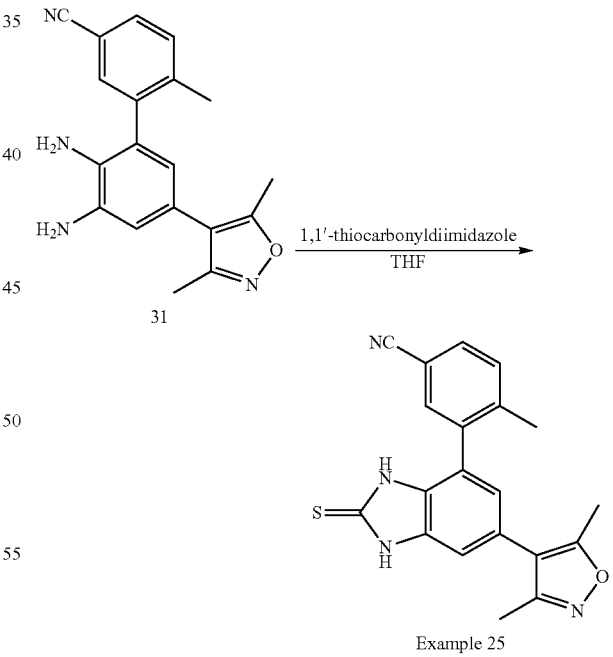

Example 25

Step 1:
To a degassed solution of 11 (6.24 g, 20 mmol), 4-methyl-3-(4,4,5,5-tetramethyl-1,3,2-dioxaborolan-2-yl)pyridine (6.57 g, 30 mmol) and K$_3$PO$_4$ (12.74 g, 60 mmol) in 1,4-dioxane (126 mL) and water (12.6 mL) was added Pd(PPh$_3$)$_4$ (2.31 g, 2 mmol). The reaction was heated at 100° C. for 20 h under N$_2$. The reaction was cooled to rt, dried over MgSO$_4$, filtered through silica gel and concentrated under reduced pressure. The residue was purified by chromatography (silica gel, 80% CH$_2$Cl$_2$/ethyl acetate) to give an impure mixture that was dissolved in ethyl acetate (200 mL) and extracted with 2N HCl (22 mL) and water (4×20 mL). The combined aqueous extracts were washed with diethyl ether (2×50 mL) and basified with solid K$_2$CO$_3$ (about 7.3 g) to pH 9. The aqueous was extracted with chloroform (4×20 mL). The combined organics were dried over MgSO$_4$, filtered and concentrated under reduced pressure to give 29 (4.48 g, 60%) as an orange solid: $^1$H NMR (400 MHz, CDCl$_3$) δ 8.61 (d, J=5.2 Hz, 1H), 8.46 (s, 1H), 8.14 (d, J=2.0 Hz, 1H), 7.33 (d, J=5.2 Hz, 1H), 7.16 (d, J=2.0 Hz, 1H), 6.06 (br.s, 2H), 2.44 (s, 3H), 2.29 (s, 3H), 2.24 (s, 3H).

Step 2:
Concentrated hydrochloric acid (20.7 mL, 249 mmol) was added in one portion to a stirred suspension of 29 (4.48 g, 13.8 mmol) and tin granules (4.92 g, 41.4 mmol) in ethanol (146 mL). The reaction was stirred at rt for 23 h. After that Starting with (5-cyano-2-methylphenyl)boronic acid, compound 31 was prepared using the method for Example Compound 22 step 1 to 2.

A mixture of 31 (0.2 g, 0.63 mmol) and 1,1'-thiocarbonyldiimidazole (0.17 g, 0.95 mmol) in THF (8.0 mL) was heated at reflux for 18 h. The reaction was cooled to rt, filtered and concentrated under reduced pressure. Ice-cold water (20 mL) was added to the residue and the product was extracted with chloroform (2×20 mL). The combined organics were washed with brine, dried over Na$_2$SO$_4$ and concentrated under reduced pressure. The crude product was purified by flash column chromatography (silica gel, 0-3% MeOH/dichloromethane) to give Example Compound 25 (0.19 g, 83.9%) as an off-white solid: $^1$H NMR (400 MHz, CDCl$_3$) δ 10.26 (br.s, 2H), 7.68 (d, J=8.2 Hz, 1H), 7.58 (s, 1H), 7.50 (d, J=7.8 Hz, 1H), 7.13 (s, 1H), 6.92 (s, 1H), 2.43 (s, 3H), 2.29 (s, 6H); ESI MS m/z 361 [M+H]$^+$.

TABLE 1

Examples prepared using methods described above.

| Example Compound | Chemical Name | Structure | General procedure | Characterization | Purity HPLC |
|---|---|---|---|---|---|
| 1 | 4,6-bis(3,5-dimethylisoxazol-4-yl)-1H-benzo[d]imidazol-2(3H)-one | 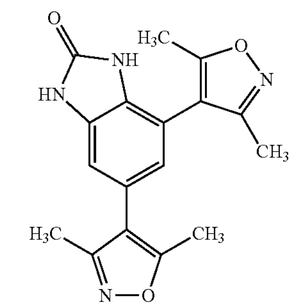 [SMILES: Cc1noc(C)c1-c1cc(-c2c(C)noc2C)c2[nH]c(=O)[nH]c2c1] | none | $^1$H NMR (300 MHz, DMSO-d$_6$) δ 10.85 (s, 1H), 10.72 (s, 1H), 6.91 (s, 1H), 6.83 (d, J = 1.5 Hz, 1H), 2.41 (s, 3H), 2.31 (s, 3H), 2.24 (s, 3H), 2.15 (s, 3H); ESI m/z 325 [M + H]+. | 98.3 |
| 2 | 5,7-bis(3,5-dimethylisoxazol-4-yl)-1-methyl-1H-benzo[d]imidazol-2(3H)-one | 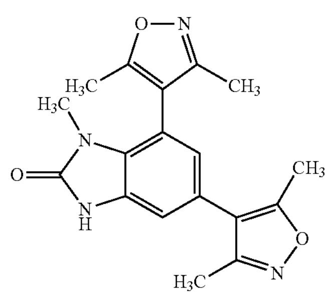 [SMILES: Cc1noc(C)c1-c1cc(-c2c(C)noc2C)c2c(c1)[nH]c(=O)n2C] | none | $^1$H NMR (300 MHz, DMSO-d$_6$) δ 11.17 (s, 1H), 7.01 (d, J = 1.8 Hz, 1H), 6.79 (d, J = 1.8 Hz, 1H), 2.95 (s, 3H), 2.49 (s, 3H), 2.41 (s, 3H), 2.23 (s, 3H), 2.10 (s, 3H); ESI m/z 339 [M + H]+. | >99 |
| 3 | 5,7-bis(3,5-dimethylisoxazol-4-yl)benzo[d]oxazol-2(3H)-one | 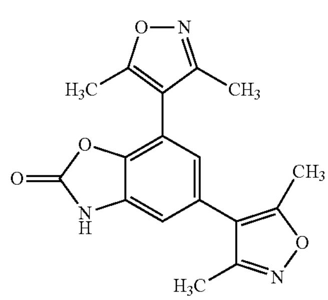 [SMILES: Cc1noc(C)c1-c1cc(-c2c(C)noc2C)c2oc(=O)[nH]c2c1] | none | $^1$H NMR (300 MHz, DMSO-d$_6$) δ 11.90 (br s, 1H), 7.15-7.08 (m, 2H), 2.43 (s, 3H), 2.41 (s, 3H), 2.26 (s, 3H), 2.24 (s, 3H); MM m/z 324 [M − H]−. | >99 |
| 4 | 5-(3,5-dimethylisoxazol-4-yl)-1-methyl-7-(2-methylpyridin-3-yl)-1H-benzo[d]imidazol-2(3H)-one | 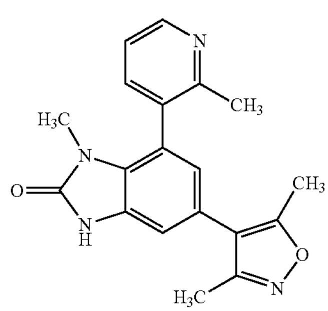 [SMILES: Cc1ncccc1-c1cc(-c2c(C)noc2C)cc2[nH]c(=O)n(C)c12] | A | $^1$H NMR (300 MHz, DMSO-d$_6$) δ 11.17 (s, 1H), 8.54 (dd, J = 5.0, 1.7 Hz, 1H), 7.74 (dd, J = 7.6, 1.8 Hz, 1H), 7.36-7.29 (m, 1H), 7.00 (d, J = 1.8 Hz, 1H), 6.78 (d, J = 1.5 Hz, 1H), 2.70 (s, 3H), 2.40 (s, 3H), 2.31 (s, 3H), 2.23 (s, 3H); ESI m/z 335 [M + H]+. | >99 |

TABLE 1-continued

Examples prepared using methods described above.

| Example Compound | Chemical Name | Structure | General procedure | Characterization | Purity HPLC |
|---|---|---|---|---|---|
| 5 | 5-(3,5-dimethylisoxazol-4-yl)-1-methyl-7-(2-(trifluoromethyl)phenyl)-1H-benzo[d]imidazol-2(3H)-one | 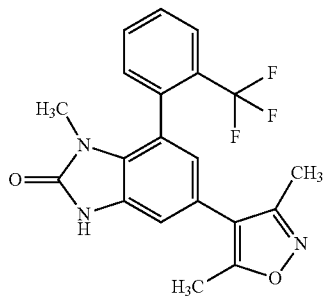 [SMILES: Cc1noc(C)c1-c1cc(-c2ccccc2C(F)(F)F)c2c(c1)[nH]c(=O)n2C] | A | $^1$H NMR (300 MHz, DMSO-d$_6$) δ 11.17 (s, 1H), 7.93-7.87 (m, 1H), 7.79-7.66 (m, 2H), 7.64-7.57 (m, 1H), 7.00 (d, J = 1.5 Hz, 1H), 6.79-6.76 (m, 1H), 2.62 (s, 3H), 2.38 (s, 3H), 2.20 (s, 3H); ESI m/z 388 [M + H]+. | 98.3 |
| 6 | 5-(3,5-dimethylisoxazol-4-yl)-1-methyl-7-(4-methylpyridin-3-yl)-1H-benzo[d]imidazol-2(3H)-one | 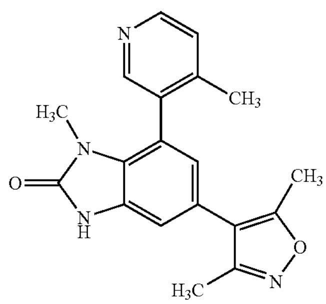 [SMILES: Cc1ccncc1-c1cc(-c2c(C)noc2C)cc2[nH]c(=O)n(C)c12] | A | $^1$H NMR (300 MHz, DMSO-d$_6$) δ 11.17 (s, 1H), 8.54-8.47 (m, 2H), 7.39 (d, J = 4.8 Hz, 1H), 7.01 (d, J = 1.8 Hz, 1H), 6.78 (d, J = 1.5 Hz, 1H), 2.70 (s, 3H), 2.41 (s, 3H), 2.23 (s, 3H), 2.14 (s, 3H); ESI m/z 335 [M + H]+. | >99 |
| 7 | 7-(1,3-dimethyl-1H-pyrazol-4-yl)-5-(3,5-dimethylisoxazol-4-yl)-1-methyl-1H-benzo[d]imidazol-2(3H)-one | 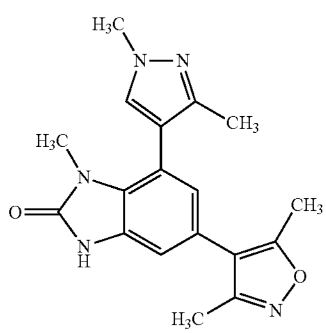 [SMILES: Cc1nn(C)cc1-c1cc(-c2c(C)noc2C)cc2[nH]c(=O)n(C)c12] | A | $^1$H NMR (300 MHz, DMSO-d$_6$) δ 11.06 (s, 1H), 7.76 (s, 1H), 6.92 (d, J = 1.5 Hz, 1H), 6.71 (d, J = 1.8 Hz, 1H), 3.82 (s, 3H), 2.95 (s, 3H), 2.39 (s, 3H), 2.21 (s, 3H), 2.06 (s, 3H); ESI m/z 338 [M + H]+. | >99 |
| 8 | 5-(3,5-dimethylisoxazol-4-yl)-1-methyl-7-(2-(trifluoromethyl)pyridin-3-yl)-1H-benzo[d]imidazol-2(3H)-one | 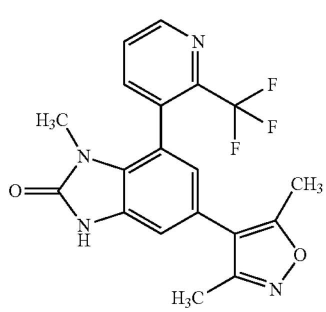 [SMILES: Cc1noc(C)c1-c1cc(-c2cccnc2C(F)(F)F)c2c(c1)[nH]c(=O)n2C] | A | $^1$H NMR (300 MHz, DMSO-d$_6$) δ 11.29 (s, 1H), 8.86 (d, J = 5.3 Hz, 1H), 8.10-8.07 (m, 1H), 7.91-7.87 (m, 1H), 7.08 (d, J = 1.7 Hz, 1H), 6.95 (d, J = 1.7 Hz, 1H), 2.87 (s, 3H), 2.49 (s, 3H), 2.22 (s, 3H); ESI m/z 389 [M + H]+. | 96.8 |

TABLE 1-continued

Examples prepared using methods described above.

| Example Compound | Chemical Name | Structure | General procedure | Characterization | Purity HPLC |
|---|---|---|---|---|---|
| 9 | 5-(3,5-dimethylisoxazol-4-yl)-1-methyl-7-(1,3,5-trimethyl-1H-pyrazol-4-yl)-1H-benzo[d]imidazol-2(3H)-one | 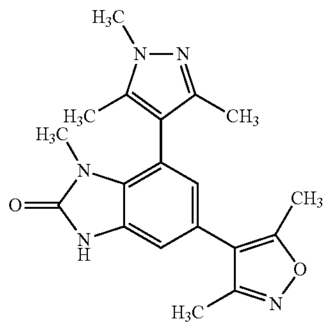 [SMILES: Cc1noc(C)c1-c1cc(-c2c(C)nn(C)c2C)c2c(c1)[nH]c(=O)n2C] | A | $^1$H NMR (300 MHz, DMSO-d$_6$) δ 11.05 (s, 1H), 6.93 (d, J = 1.7 Hz, 1H), 6.65 (d, J = 1.7 Hz, 1H), 3.72 (s, 3H), 2.88 (s, 3H), 2.40 (s, 3H), 2.22 (s, 3H), 2.08 (s, 3H), 1.97 (s, 3H); ESI m/z 352 [M + H]+. | >99 |
| 10 | 5-(3,5-dimethylisoxazol-4-yl)-1-methyl-7-(4-methylisothiazol-5-yl)-1H-benzo[d]imidazol-2(3H)-one | 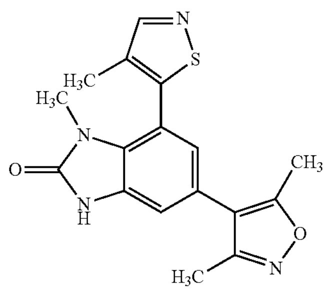 [SMILES: Cc1cnsc1-c1cc(-c2c(C)noc2C)cc2[nH]c(=O)n(C)c12] | A | $^1$H NMR (300 MHz, DMSO-d$_6$) δ 11.23 (s, 1H), 9.15 (s, 1H), 7.03 (d, J = 1.7 Hz, 1H), 6.86 (d, J = 1.7 Hz, 1H), 2.98 (s, 3H), 2.40 (s, 3H), 2.25 (s, 3H), 2.22 (s, 3H); ESI m/z 341 [M + H]+. | >99 |
| 11 | 5-(3,5-dimethylisoxazol-4-yl)-7-(4-fluoro-2-(trifluoromethyl)phenyl)-1-methyl-1H-benzo[d]imidazol-2(3H)-one | 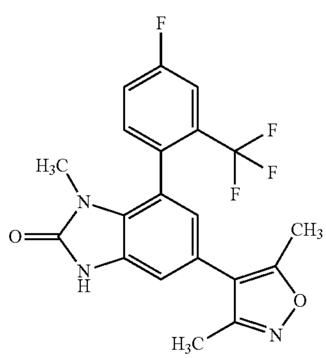 [SMILES: Cc1noc(C)c1-c1cc(-c2ccc(F)cc2C(F)(F)F)c2c(c1)[nH]c(=O)n2C] | A | $^1$H NMR (300 MHz, DMSO-d$_6$) δ 11.18 (s, 1H), 7.81 (dd, J = 9.5, 2.4 Hz, 1H), 7.32-7.59 (m, 2H), 7.01 (d, J = 1.8 Hz, 1H), 6.79-6.77 (m, 1H), 2.66 (s, 3H), 2.37 (s, 3H), 2.20 (s, 3H); ESI m/z 406 [M + H]+. | >99 |
| 12 | 5-(3,5-dimethylisoxazol-4-yl)-7-(2-methoxy-5-methylphenyl)-1-methyl-1H-benzo[d]imidazol-2(3H)-one | 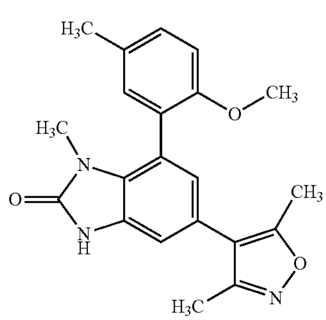 [SMILES: COc1ccc(C)cc1-c1cc(-c2c(C)noc2C)cc2[nH]c(=O)n(C)c12] | A | $^1$H NMR (300 MHz, DMSO-d$_6$) δ 11.04 (s, 1H), 7.76-7.18 (m, 1H), 7.12 (d, J = 2.2 Hz, 1H), 7.00 (d, J = 8.4 Hz, 1H), 6.93 (d, J = 1.8 Hz, 1H), 6.71 (d, J = 1.5 Hz, 1H), 3.70 (s, 3H), 2.80 (s, 3H), 2.40 (s, 3H), 2.29 (s, 3H), 2.22 (s, 3H); ESI m/z 364 [M + H]+. | 99.0 |

TABLE 1-continued

Examples prepared using methods described above.

| Example Compound | Chemical Name | Structure | General procedure | Characterization | Purity HPLC |
|---|---|---|---|---|---|
| 13 | 5-(3,5-dimethylisoxazol-4-yl)-7-(2-methoxypyridin-3-yl)-1-methyl-1H-benzo[d]imidazol-2(3H)-one | 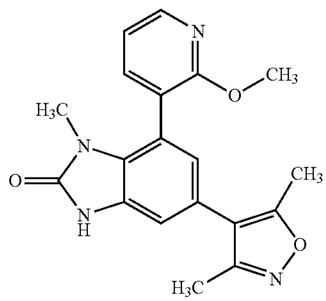 [SMILES: COc1ncccc1-c1cc(-c2c(C)noc2C)cc2[nH]c(=O)n(C)c12] | A | $^1$H NMR (300 MHz, DMSO-d$_6$) δ 11.12 (s, 1H), 8.27 (dd, J = 4.9, 1.9 Hz, 1H), 7.78 (dd, J = 7.4, 1.9 Hz, 1H), 7.17-7.10 (m, 1H), 6.98 (d, J = 1.8 Hz, 1H), 6.77 (d, J = 1.8 Hz, 1H), 3.85 (s, 3H), 2.82 (s, 3H), 2.40 (s, 3H), 2.23 (s, 3H); ESI m/z 351 [M + H]+. | >99 |
| 14 | 3-(6-(3,5-dimethylisoxazol-4-yl)-3-methyl-2-oxo-2,3-dihydro-1H-benzo[d]imidazol-4-yl)-2-methylbenzonitrile | 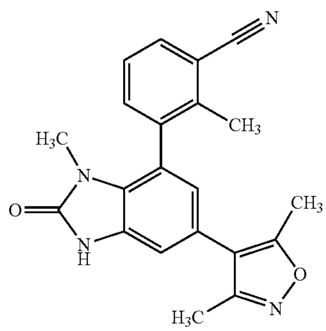 [SMILES: Cc1noc(C)c1-c1cc(-c2cccc(C#N)c2C)c2c(c1)[nH]c(=O)n2C] | A | $^1$H NMR (300 MHz, DMSO-d$_6$) δ 11.19 (s, 1H), 7.90 (dd, J = 7.7, 1.2 Hz, 1H), 7.68 (dd, J = 8.1, 1.2 Hz, 1H), 7.49 (t, J = 8.0 Hz, 1H), 7.01 (d, J = 1.8 Hz, 1H), 6.76 (d, J = 1.8 Hz, 1H), 2.68 (s, 3H), 2.40 (s, 3H), 2.30 (s, 3H), 2.24 (s, 3H); ESI m/z 359 [M + H]+. | >99 |
| 15 | 4,6-bis(3,5-dimethylisoxazol-4-yl)-1,3-dimethyl-1H-benzo[d]imidazol-2(3H)-one | 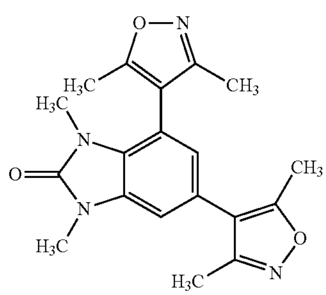 [SMILES: Cc1noc(C)c1-c1cc(-c2c(C)noc2C)c2c(c1)n(C)c(=O)n2C] | none | $^1$H NMR (300 MHz, DMSO-d$_6$) δ 7.26 (d, J = 1.8 Hz, 1H), 6.84 (d, J = 1.8 Hz, 1H), 3.40 (s, 3H), 3.00 (s, 3H), 2.43 (s, 3H), 2.29 (s, 3H), 2.26 (s, 3H), 2.09 (s, 3H); ESI m/z 353 [M + H]+. | >99 |
| 16 | 3-(6-(3,5-dimethylisoxazol-4-yl)-3-methyl-2-oxo-2,3-dihydro-1H-benzo[d]imidazol-4-yl)-4-methylbenzonitrile | 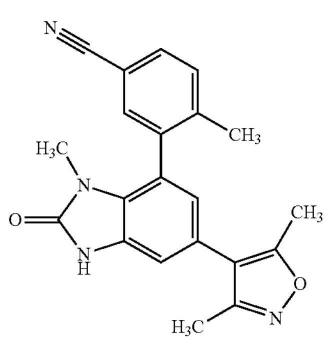 [SMILES: Cc1ccc(C#N)cc1-c1cc(-c2c(C)noc2C)cc2[nH]c(=O)n(C)c12] | A | $^1$H NMR (300 MHz, DMSO-d$_6$) δ 11.18 (s, 1H), 7.86-7.81 (m, 2H), 7.59-7.54 (m, 1H), 7.01 (d, J = 1.8 Hz, 1H), 6.76 (d, J = 1.8 Hz, 1H), 2.68 (s, 3H), 2.40 (s, 3H), 2.22 (s, 3H), 2.17 (s, 3H); ESI m/z 359 [M + H]+. | >99 |

TABLE 1-continued

Examples prepared using methods described above.

| Example Compound | Chemical Name | Structure | General procedure | Characterization | Purity HPLC |
|---|---|---|---|---|---|
| 17 | 5-(3,5-dimethylisoxazol-4-yl)-7-(4-methoxypyridin-3-yl)-1-methyl-1H-benzo[d]imidazol-2(3H)-one | 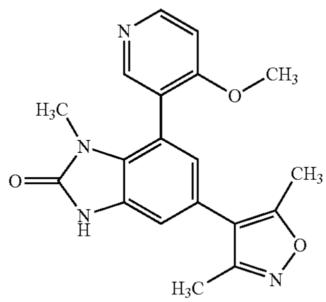 [SMILES: COc1ccncc1-c1cc(-c2c(C)noc2C)cc2[nH]c(=O)n(C)c12] | A | $^1$H NMR (300 MHz, DMSO-d$_6$) δ 11.13 (s, 1H), 8.56 (d, J = 5.7 Hz, 1H), 8.40 (s, 1H), 7.20 (d, J = 5.7 Hz, 1H), 6.99 (d, J = 1.8 Hz, 1H), 6.77 (d, J = 1.8 Hz, 1H), 3.84 (s, 3H), 2.82 (s, 3H), 2.41 (s, 3H), 2.23 (s, 3H); ESI m/z 351 [M + H]+. | >99 |
| 18 | 5-(3,5-dimethylisoxazol-4-yl)-7-(5-fluoro-2-methoxyphenyl)-1-methyl-1H-benzo[d]imidazol-2(3H)-one | 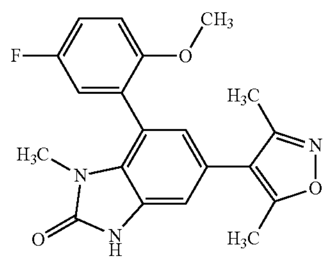 [SMILES: COc1ccc(F)cc1-c1cc(-c2c(C)noc2C)cc2[nH]c(=O)n(C)c12] | A | $^1$H NMR (300 MHz, DMSO-d$_6$) δ 11.09 (s, 1H), 7.33-7.20 (m, 2H), 7.16-7.07 (m, 1H), 6.96 (d, J = 1.7 Hz, 1H), 6.75 (d, J = 1.7 Hz, 1H), 3.72 (s, 3H), 2.82 (s, 3H), 2.40 (s, 3H), 2.23 (s, 3H); ESI m/z 366 [M − H]−. | 99.0 |
| 19 | 7-(5-chloro-2-methylphenyl)-5-(3,5-dimethylisoxazol-4-yl)-1-methyl-1H-benzo[d]imidazol-2(3H)-one | 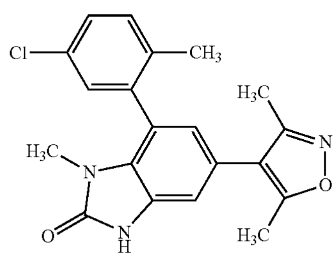 [SMILES: Cc1ccc(Cl)cc1-c1cc(-c2c(C)noc2C)cc2[nH]c(=O)n(C)c12] | A | $^1$H NMR (500 MHz, DMSO-d$_6$) δ 11.11 (s, 1H), 7.42 (dd, J = 8.0, 2.5 Hz, 1H), 7.40 (d, J = 2.0 Hz, 1H), 7.37 (d, J = 8.5 Hz, 1H), 6.98 (d, J = 1.5 Hz, 1H), 6.73 (d, J = 2.0 Hz, 1H), 2.71 (s, 3H), 2.34 (s, 3H), 2.22 (s, 3H), 2.06 (s, 3H); ESI m/z 368 [M + H]+. | 98.6 |
| 20 | 7-(6-amino-2-methylpyridin-3-yl)-5-(3,5-dimethylisoxazol-4-yl)-1-methyl-1H-benzo[d]imidazol-2(3H)-one | 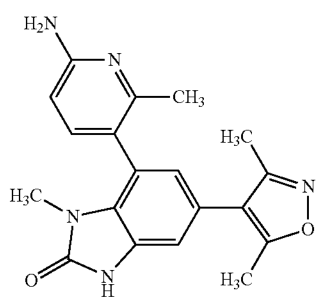 [SMILES: Cc1nc(N)ccc1-c1cc(-c2c(C)noc2C)cc2[nH]c(=O)n(C)c12] | A | $^1$H NMR (500 MHz, DMSO-d$_6$) δ 11.03 (s, 1H), 7.27 (d, J = 8.5 Hz, 1H), 6.92 (d, J = 1.5 Hz, 1H), 6.69 (d, J = 1.5 Hz, 1H), 6.35 (d, J = 8.5 Hz, 1H), 5.97 (s, 2H), 2.82 (s, 3H), 2.39 (s, 3H), 2.22 (s, 3H), 2.07 (s, 3H); ESI m/z 350 [M + H]+. | >99 |
| 21 | 7-(3,5-dimethyl-1H-pyrazol-4-yl)-5-(3,5-dimethylisoxazol-4-yl)-1-methyl-1H-benzo[d]imidazol-2(3H)-one | 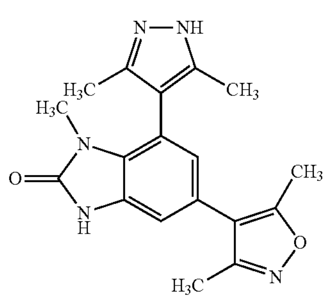 [SMILES: Cc1n[nH]c(C)c1-c1cc(-c2c(C)noc2C)cc2[nH]c(=O)n(C)c12] | A | $^1$H NMR (500 MHz, CD3OD) δ 7.03 (d, J = 1.5 Hz, 1H), 7.35-7.33 (m, 1H), 7.15 (d, J = 2.0 Hz, 1H), 6.76 (d, J = 1.5 Hz, 1H), 3.02 (s, 3H), 2.42 (s, 3H), 2.26 (s, 3H), 2.13 (br.s, 6H); ESI m/z 338 [M + H]+. | >99 |

TABLE 1-continued

Examples prepared using methods described above.

| Example Compound | Chemical Name | Structure | General procedure | Characterization | Purity HPLC |
|---|---|---|---|---|---|
| 22 | 6-(3,5-dimethylisoxazol-4-yl)-4-(1,3,5-trimethyl-1H-pyrazol-4-yl)-1H-benzo[d]imidazol-2(3H)-one | 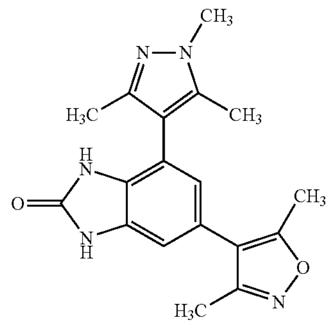 [SMILES: Cc1noc(C)c1-c1cc(-c2c(C)nn(C)c2C)c2[nH]c(=O)[nH]c2c1] | none | $^1$H NMR (500 MHz, DMSO-d$_6$) δ 10.7 (s, 1H), 10.4 (s 1H), 6.82 (d, J = 1.5 Hz, 1H), 6.68 (d, J = 1.5 Hz, 1H), 3.70 (s, 3H), 2.40 (s, 3H), 2.23 (s, 3H), 2.12 (s, 3H), 2.05 (s, 3H); ESI m/z 338 [M + H]+. | >99 |
| 23 | 6-(3,5-dimethylisoxazol-4-yl)-4-(1,3,5-trimethyl-1H-pyrazol-4-yl)-1H-benzo[d]imidazole-2(3H)-thione | 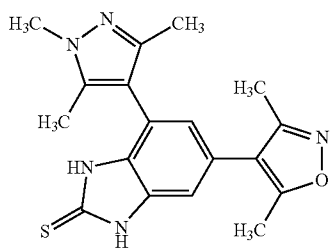 [SMILES: Cc1noc(C)c1-c1cc(-c2c(C)nn(C)c2C)c2[nH]c(=S)[nH]c2c1] | No general procedure | $^1$H NMR (400 MHz, DMSO-d$_6$) δ 12.37 (br.s, 2H), 7.01 (s, 1H), 6.87 (s, 1H), 3.71 (s, 3H), 2.42 (s, 3H), 2.24 (s, 3H), 2.11 (s, 3H), 2.05 (s, 3H); ESI m/z 352 [M − H]−. | 98.5 |
| 24 | 6-(3,5-dimethylisoxazol-4-yl)-4-(4-methylpyridin-3-yl)-1H-benzo[d]imidazole-2-thiol | 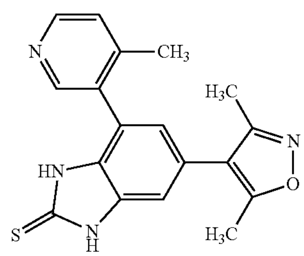 [SMILES: Cc1ccncc1-c1cc(-c2c(C)noc2C)cc2[nH]c(=S)[nH]c12] | No general procedure | $^1$H NMR (400 MHz, CDCl$_3$) δ 12.58 (br.s, 1H), 11.33 (br.s, 1H), 8.45 (s, 1H), 8.23 (d, J = 5.4 Hz, 1H), 7.22 (d, J = 5.4 Hz, 1H), 7.15 (d, J = 1.2 Hz, 1H), 6.91 (d, J = 1.2 Hz, 1H), 2.41 (s, 3H), 2.28 (s, 3H), 2.27 (s, 3H); ESI MS m/z 337 [M + H]+. | 98.7 |
| 25 | 3-(6-(3,5-dimethylisoxazol-4-yl)-2-thioxo-2,3-dihydro-1H-benzo[d]imidazol-4-yl)-4-methylbenzonitrile | 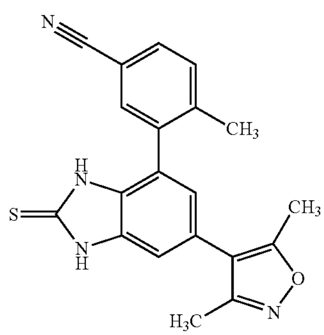 [SMILES: Cc1ccc(C#N)cc1-c1cc(-c2c(C)noc2C)cc2[nH]c(=S)[nH]c12] | No general procedure | $^1$H NMR (400 MHz, CDCl$_3$) δ 10.26 (br.s, 2H), 7.68 (d, J = 8.2 Hz, 1H), 7.58 (s, 1H), 7.50 (d, J = 7.8 Hz, 1H), 7.13 (s, 1H), 6.92 (s, 1H), 2.43 (s, 3H), 2.29 (s, 6H); ESI MS m/z 361 [M + H]+. | 97.4 |
| 26 | 5-(3,5-dimethylisoxazol-4-yl)-1-methyl-7-((1,3,5-trimethyl-1H-pyrazol-4-yl)amino)-1H-benzo[d]imidazol-2(3H)-one | 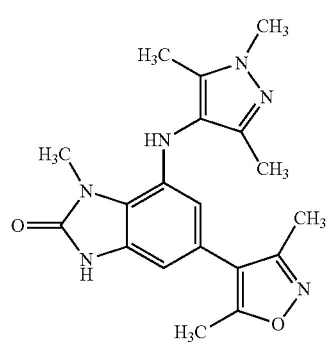 [SMILES: Cc1nn(C)c(C)c1Nc1cc(-c2c(C)noc2C)cc2[nH]c(=O)n(C)c12] | B | $^1$H NMR (500 MHz, CD$_3$OD) δ 5.45 (s, 1H), 5.89 (s, 1H), 3.77 (s, 3H), 3.72 (s, 3H), 2.27 (s, 3H), 2.14 (s, 3H), 2.10 (s, 3H), 2.06 (s, 3H); ESI m/z 367 [M + H]+. | 97.9 |

TABLE 1-continued

Examples prepared using methods described above.

| Example Compound | Chemical Name | Structure | General procedure | Characterization | Purity HPLC |
|---|---|---|---|---|---|
| 27 | 5-(3,5-dimethylisoxazol-4-yl)-1-methyl-7-((2-methylpyridin-3-yl)amino)-1H-benzo[d]imidazol-2(3H)-one | 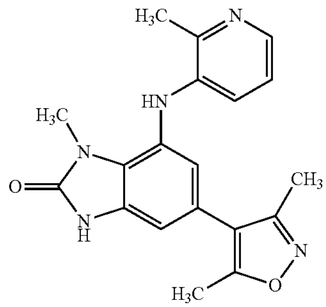 [SMILES: Cc1ncccc1Nc1cc(-c2c(C)noc2C)cc2[nH]c(=O)n(C)c12] | B | $^1$H NMR (500 MHz, CD$_3$OD) δ 7.86 (dd, J = 1.3, 4.8 Hz, 1H), 7.08-7.03 (m, 1H), 6.93 (d, J = 1.5 Hz, 1H), 6.78 (d, J = 1.5 1H), 6.77 (dd, J = 1.2, 8.2 Hz, 1H), 3.35 (s, 3H), 2.55 (s, 3H), 2.39 (s, 3H), 2.23 (s, 3H); ESI m/z 350 [M + H]+. | >99 |
| 28 | 5-(5-(hydroxyl methyl)-3-methylisoxazol-4-yl)-1-methyl-7-(1,3,5-trimethyl-1H-pyrazol-4-yl)-1H-benzo[d]imidazol-2(3H)-one | 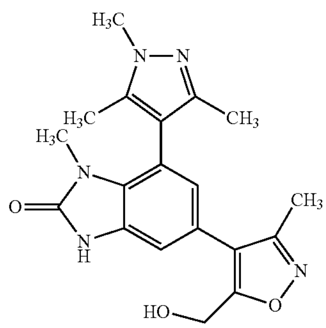 [SMILES: Cc1noc(CO)c1-c1cc(-c2c(C)nn(C)c2C)c2c(c1)[nH]c(=O)n2C] | C | $^1$H NMR (300 MHz, DMSO-d$_6$) δ 11.08 (s, 1H), 7.03 (d, J = 1.5 Hz, 1H), 6.74 (d, J = 1.8 Hz, 1H), 5.65 (t, J = 5.7 Hz, 1H), 4.49 (d, J = 5.7 Hz, 2H), 3.73 (s, 3H), 2.88 (s, 3H), 2.27 (s, 3H), 2.09 (s, 3H), 1.97 (s, 3H); ESI m/z 368 [M + H]+. | 98.7 |
| 29 | 3-(6-(3,5-dimethylisoxazol-4-yl)-3-methyl-2-oxo-2,3-dihydro-1H-benzo[d]imidazol-4-yl)-4-methyl benzamide | 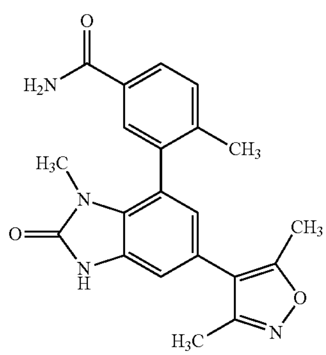 [SMILES: Cc1ccc(C(N)=O)cc1-c1cc(-c2c(C)noc2C)cc2[nH]c(=O)n(C)c12] | E | $^1$H NMR (500 MHz, DMSO-d$_6$) δ 11.11 (br.s, 1H), 7.94 (br.s, 1H), 7.87 (dd, J = 7.8, 2.0 Hz, 1H), 7.82 (d, J = 2.0 Hz, 1H), 7.42 (d, J = 8.0 Hz, 1H), 7.31 (br.s, 1H), 6.99 (d, J = 2.0 Hz, 1H), 6.75 (d, J = 1.5 Hz, 1H) 2.67 (s, 3H), 2.40 (s, 3H), 2.22 (s, 3H), 2.15 (s, 3H); ESI m/z 377 [M + H]+. | >99 |
| 30 | 3-(6-(3,5-dimethylisoxazol-4-yl)-3-methyl-2-oxo-2,3-dihydro-1H-benzo[d]imidazol-4-yl)-2-methyl benzamide | 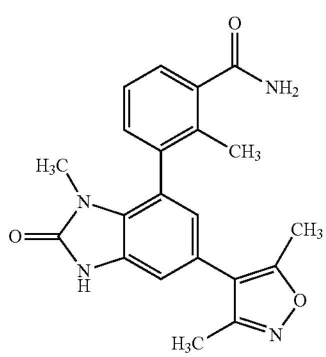 [SMILES: Cc1noc(C)c1-c1cc(-c2cccc(C(N)=O)c2C)c2c(c1)[nH]c(=O)n2C] | E | $^1$H NMR (500 MHz, DMSO-d$_6$) δ 11.10 (br.s, 1H), 7.79 (br.s, 1H), 7.45 (br.s, 1H), 7.41 (dd, J = 7.5, 1.5 Hz, 1H), 7.35 (dd, J = 7.5, 1.5 Hz, 1H), 7.30 (t, J = 7.5 Hz, 1H), 6.98 (d, J = 2.0 Hz, 1H), 6.68 (d, J = 1.5 Hz, 1H), 2.69 (s, 3H), 2.40 (s, 3H), 2.22 (s, 3H), 2.11 (s, 3H); ESI m/z 377 [M + H]+. | >99 |

TABLE 1-continued

Examples prepared using methods described above.

| Example Compound | Chemical Name | Structure | General procedure | Characterization | Purity HPLC |
|---|---|---|---|---|---|
| 31 | 5-(3,5-dimethylisoxazol-4-yl)-1-methyl-7-((2-methylpyridin-3-yl)oxy)-1H-benzo[d]imidazol-2(3H)-one | 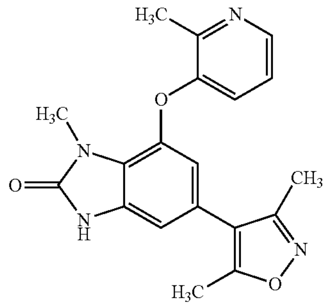 [SMILES: Cc1ncccc1Oc1cc(-c2c(C)noc2C)cc2[nH]c(=O)n(C)c12] | No general procedure | $^1$H NMR (500 MHz, CD$_3$OD) δ 8.21 (dd, J = 1.5, 4.6 Hz, 1H), 7.31 (dd, J = 1.5, 8.3 Hz, 1H), 7.27 (dd, J = 4.6, 8.4 Hz, 1H), 6.87 (d, J = 1.4 Hz, 1H), 6.49 (d, J = 1.4 Hz, 1H), 3.51 (s, 3H), 2.59 (s, 3H), 2.34 (s, 3H), 2.17 (s, 3H); HPLC 97.0%, tR = 8.5 min; ESI m/z 351 [M + H]+. | 97.0 |
| 32 | 7-(3,5-dimethyl-1H-pyrazol-4-yl)-5-(5-(hydroxymethyl)-3-methylisoxazol-4-yl)-1-methyl-1H-benzo[d]imidazol-2(3H)-one | 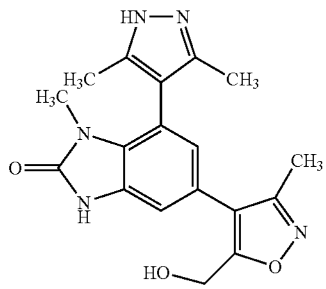 [SMILES: Cc1n[nH]c(C)c1-c1cc(-c2c(C)noc2CO)cc2[nH]c(=O)n(C)c12] | C | $^1$H NMR (300 MHz, DMSO-d$_6$) δ 12.37 (br.s, 1H), 11.07 (s, 1H), 7.03 (d, J = 1.8 Hz, 1H), 6.76 (d, J = 1.5 Hz, 1H), 5.65 (t, J = 5.7 Hz, 1H), 4.49 (d, J = 5.7 Hz, 2H), 2.87 (s, 3H), 2.27 (s, 3H), 2.04 (br.s, 6H); ESI m/z 354 [M + H]+. | 98.7 |
| 33 | 5-(3,5-dimethylisoxazol-4-yl)-7-((3,5-dimethylisoxazol-4-yl)amino)-1-methyl-1H-benzo[d]imidazol-2(3H)-one | 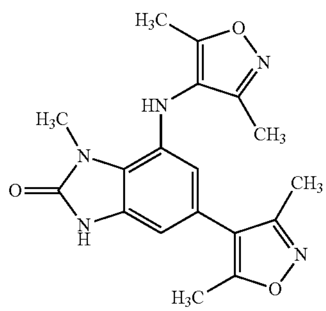 [SMILES: Cc1noc(C)c1Nc1cc(-c2c(C)noc2C)cc2[nH]c(=O)n(C)c12] | B | $^1$H NMR (300 MHz, CD$_3$OD) δ 6.57 (d, J = 1.5 Hz, 1H), 6.02 (d, J = 1.5 Hz, 1H), 3.75 (s, 3H), 2.03 (s, 3H), 2.29 (s, 3H), 2.13 (s, 3H), 2.11 (s, 3H); ESI m/z 354 [M + H]+. | 95.7 |
| 34 | 5-(3,5-dimethylisoxazol-4-yl)-1-methyl-7-(naphthalen-1-yl)-1H-benzo[d]imidazol-2(3H)-one | 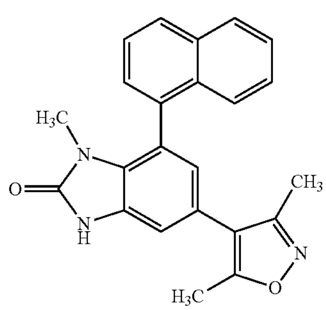 [SMILES: Cc1noc(C)c1-c1cc(-c2cccc3ccccc23)c2c(c1)[nH]c(=O)n2C] | A | $^1$H NMR (300 MHz, DMSO-d$_6$) δ 11.2 (s, 1H), 8.06 (s, 1H), 8.03 (s, 1H), 7.63-7.50 (m, 5H), 7.07 (d, J = 1.5 Hz, 1H), 6.86 (d, J = 1.8 Hz, 1H), 2.41 (s, 3H), 2.40 (s, 3H), 2.24 (s, 3H); ESI MS m/z 370 [M + H]+. | 95.6 |
| 35 | 7-(3,5-dichloropyridin-4-yl)-5-(3,5-dimethylisoxazol-4-yl)-1-methyl-1H-benzo[d]imidazol-2(3H)-one | 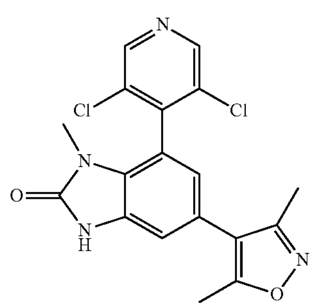 [SMILES: Cc1noc(C)c1-c1cc(-c2c(Cl)cncc2Cl)c2c(c1)[nH]c(=O)n2C] | D | $^1$H NMR (500 MHz, CD$_3$OD) δ 8.71 (s, 2H), 7.14 (d, J = 1.6 Hz, 1H), 6.83 (d, J = 1.6 Hz, 1H), 2.97 (s, 3H), 2.42 (s, 3H), 2.26 (s, 3H); ESI m/z 389 [M + H]+. | >99 |

TABLE 1-continued

Examples prepared using methods described above.

| Example Compound | Chemical Name | Structure | General procedure | Characterization | Purity HPLC |
|---|---|---|---|---|---|
| 36 | 5-(3,5-dimethylisoxazol-4-yl)-1-methyl-7-(quinolin-3-yl)-1H-benzo[d]imidazol-2(3H)-one | 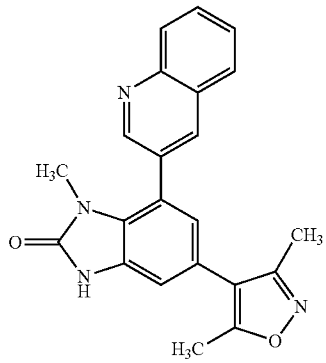 [SMILES: Cc1noc(C)c1-c1cc(-c2cnc3ccccc3c2)c2c(c1)[nH]c(=O)n2C] | A | ¹H NMR (300 MHz, DMSO-d₆) δ 11.2 (s, 1H), 9.06 (d, J = 2.4 Hz, 1H), 8.53 (d, J = 2.1 Hz, 1H), 8.10 (d, J = 7.8 Hz, 1H), 8.08 (d, J = 6.9 Hz, 1H), 7.86-7.80 (m, 1H), 7.72-7.69 (m, 1H), 7.07 (d, J = 1.5 Hz, 1H), 6.99 (d, J = 1.5 Hz, 1H), 2.87 (s, 3H), 2.43 (s, 3H), 2.25 (s, 3H); ESI MS m/z 371 [M + H]+. | >99 |
| 37 | 7-(2-chlorophenyl)-5-(3,5-dimethylisoxazol-4-yl)-1-methyl-1H-benzo[d]imidazol-2(3H)-one | 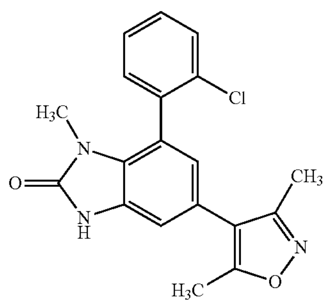 [SMILES: Cc1noc(C)c1-c1cc(-c2ccccc2Cl)c2c(c1)[nH]c(=O)n2C] | A | ¹H NMR (300 MHz, DMSO-d₆) δ 11.2 (s, 1H), 7.63-7.43 (m, 4H), 7.01 (d, J = 1.5 Hz, 1H), 6.76 (d, J = 1.5 Hz, 1H), 2.76 (s, 3H), 2.41 (s, 3H), 2.23 (s, 3H); ESI MS m/z 354 [M + H]+. | 97.8 |
| 38 | 5-(3,5-dimethylisoxazol-4-yl)-1-methyl-7-(3-methylpyridin-4-yl)-1H-benzo[d]imidazol-2(3H)-one | 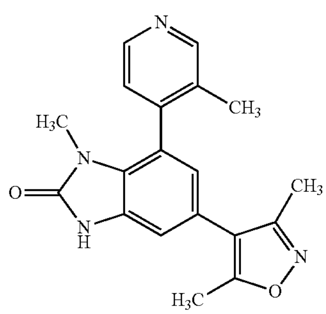 [SMILES: Cc1cnccc1-c1cc(-c2c(C)noc2C)cc2[nH]c(=O)n(C)c12] | D | ¹H NMR (500 MHz, CD₃OD) δ 8.53 (s, 1H), 8.47 (d, J = 4.9 Hz, 1H), 7.42 (d, J = 5.0 Hz, 1H), 7.09 (d, J = 1.4 Hz, 1H), 6.79 (d, J = 1.4 Hz, 1H), 2.88 (s, 3H), 2.41 (s, 3H), 2.25 (s, 3H), 2.19 (s, 3H); ESI m/z 335 [M + H]+. | >99 |
| 39 | 5-(3,5-dimethylisoxazol-4-yl)-7-(3,5-dimethylpyridin-4-yl)-1-methyl-1H-benzo[d]imidazol-2(3H)-one | 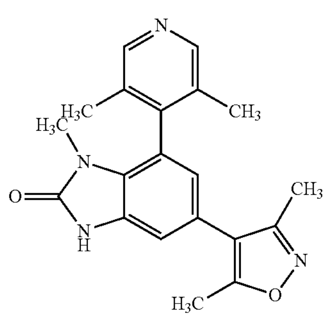 [SMILES: Cc1cncc(C)c1-c1cc(-c2c(C)noc2C)cc2[nH]c(=O)n(C)c12] | D | ¹H NMR (500 MHz, CD₃OD) δ 8.37 (s, 2H), 7.10 (d, J = 1.6 Hz, 1H), 6.72 (d, J = 1.6 Hz, 1H), 2.82 (s, 3H), 2.41 (s, 3H), 2.25 (s, 3H), 2.11 (s, 6H); ESI m/z 349 [M + H]+. | >99 |

TABLE 1-continued

Examples prepared using methods described above.

| Example Compound | Chemical Name | Structure | General procedure | Characterization | Purity HPLC |
|---|---|---|---|---|---|
| 40 | 5-(3,5-dimethylisoxazol-4-yl)-1-methyl-7-(o-tolyl)-1H-benzo[d]imidazol-2(3H)-one | 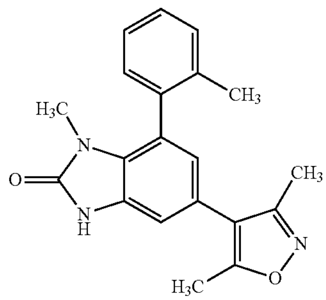 [SMILES: Cc1ccccc1-c1cc(-c2c(C)noc2C)cc2[nH]c(=O)n(C)c12] | A | $^1$H NMR (300 MHz, DMSO-d$_6$) δ 11.1 (s, 1H), 7.35-7.29 (m, 4H), 6.96 (d, J = 1.8 Hz, 1H), 6.71 (d, J = 1.8 Hz, 1H), 2.67 (s, 3H), 2.40 (s, 3H), 2.22 (s, 3H), 2.09 (s, 3H); ESI MS m/z 334 [M + H]+. | >99 |
| 41 | 5-(3,5-dimethylisoxazol-4-yl)-7-(2-fluoro-5-methoxyphenyl)-1-methyl-1H-benzo[d]imidazol-2(3H)-one | 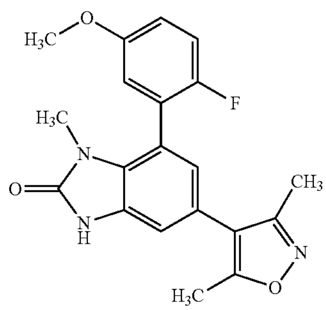 [SMILES: COc1ccc(F)c(-c2cc(-c3c(C)noc3C)cc3[nH]c(=O)n(C)c23)c1] | A | $^1$H NMR (300 MHz, DMSO-d$_6$) δ 11.2 (s, 1H), 7.30-7.24 (m, 1H), 7.07-7.01 (m, 3H), 6.85 (d, J = 1.5 Hz, 1H), 3.79 (s, 3H), 2.89 (s, 3H), 2.41 (s, 3H), 2.23 (s, 3H); ESI m/z 368 [M + H]+. | >99 |
| 42 | 7-(5-chloro-2-methoxyphenyl)-5-(3,5-dimethylisoxazol-4-yl)-1-methyl-1H-benzo[d]imidazol-2(3H)-one | 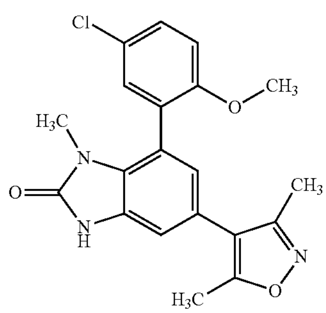 [SMILES: COc1ccc(Cl)cc1-c1cc(-c2c(C)noc2C)cc2[nH]c(=O)n(C)c12] | A | $^1$H NMR (300 MHz, DMSO-d$_6$) δ 11.1 (s, 1H), 7.51-7.48 (m, 1H), 7.39 (d, J = 2.7 Hz, 1H), 7.15 (d, J = 9.0 Hz, 1H), 6.96 (d, J = 1.5 Hz, 1H), 6.75 (d, J = 1.5 Hz, 1H), 3.74 (s, 3H), 2.82 (s, 3H), 2.40 (s, 3H), 2.22 (s, 3H); ESI MS m/z 384 [M + H]+. | 94.2 |
| 43 | 5-(3,5-dimethylisoxazol-4-yl)-7-(2-fluoro-3-methoxyphenyl)-1-methyl-1H-benzo[d]imidazol-2(3H)-one | 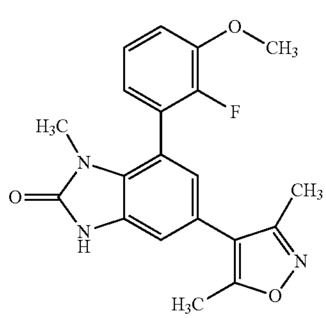 [SMILES: COc1cccc(-c2cc(-c3c(C)noc3C)cc3[nH]c(=O)n(C)c23)c1F] | A | $^1$H NMR (300 MHz, DMSO-d$_6$) δ 11.2 (s, 1H), 7.28-7.21 (m, 2H), 7.06-7.01 (m, 2H), 6.81 (d, J = 1.5 Hz, 1H), 3.89 (s, 3H), 2.85 (s, 3H), 2.40 (s, 3H), 2.22 (s, 3H); ESI MS m/z 368 [M + H]+. | >99 |

TABLE 1-continued

Examples prepared using methods described above.

| Example Compound | Chemical Name | Structure | General procedure | Characterization | Purity HPLC |
|---|---|---|---|---|---|
| 44 | 5-(3,5-dimethylisoxazol-4-yl)-7-(2,4-dimethyl thiazol-5-yl)-1-methyl-1H-benzo[d]imidazol-2(3H)-one | 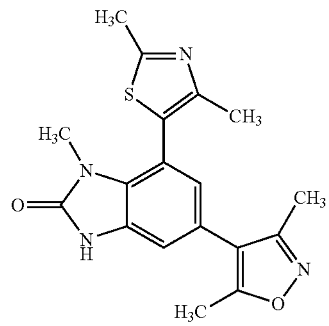 [SMILES: Cc1nc(C)c(-c2cc(-c3c(C)noc3C)cc3[nH]c(=O)n(C)c23)s1] | A | ¹H NMR (300 MHz, DMSO-d₆) δ 11.2 (s, 1H), 7.01 (d, J = 1.8 Hz, 1H), 6.83 (d, J = 1.5 Hz, 1H), 2.94 (s, 3H), 2.66 (s, 3H), 2.39 (s, 3H), 2.21 (s, 3H), 2.15 (s, 3H); ESI MS m/z 355 [M + H]+. | >99 |
| 45 | 5-(3,5-dimethylisoxazol-4-yl)-7-(2-methoxy-6-methylpyridin methyl-1H-benzo[d]imidazol-2(3H)-one | 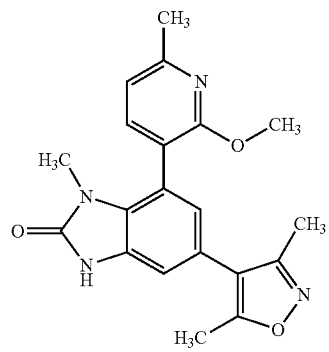 [SMILES: COc1nc(C)ccc1-c1cc(-c2c(C)noc2C)cc2[nH]c(=O)n(C)c12] | A | ¹H NMR (300 MHz, DMSO-d₆) δ 11.1 (s, 1H), 7.65 (d, J = 7.2 Hz, 1H), 6.99 (s, 1H), 6.96 (d, J = 1.8 Hz, 1H), 6.73 (d, J = 1.8 Hz, 1H), 3.82 (s, 3H), 2.83 (s, 3H), 2.48 (s, 3H), 2.40 (s, 3H), 2.22 (s, 3H); ESI MS m/z 365 [M + H]+. | >99 |
| 46 | 7-(benzo[d]oxazol-5-yl)-5-(3,5-dimethyl isoxazol-4-yl)-1-methyl-1H-benzo[d]imidazol-2(3H)-one | 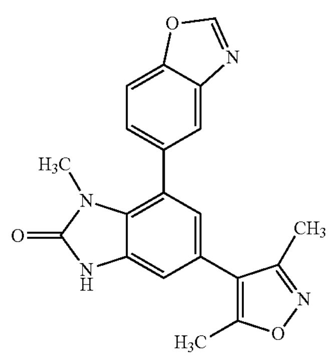 [SMILES: Cc1noc(C)c1-c1cc(-c2ccc3ocnc3c2)c2c(c1)[nH]c(=O)n2C] | A | ¹H NMR (300 MHz, DMSO-d₆) δ 11.2 (s, 1H), 8.85 (s, 1H), 7.92 (d, J = 1.2 Hz, 1H), 7.86 (d, J = 8.4 Hz, 1H), 7.56-7.53 (m, 1H), 7.00 (d, J = 1.5 Hz, 1H), 6.85 (d, J = 1.8 Hz, 1H), 2.79 (s, 3H), 2.42 (s, 3H), 2.24 (s, 3H); ESI MS m/z 361 [M + H]+. | 91.4 |
| 47 | 7-(cyclohex-1-en-1-yl)-5-(3,5-dimethyl isoxazol-4-yl)-1-methyl-1H-benzo[d]imidazol-2(3H)-one | 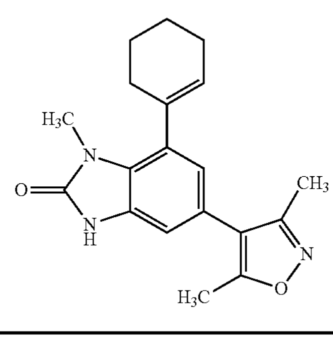 | A | ¹H NMR (300 MHz, DMSO-d6) δ 11.0 (s, 1H), 6.82 (d, J = 1.8 Hz, 1H), 6.67 (d, J = 1.8 Hz, 1H), 5.68-5.67 (m, 1H), 3.30 (s, 3H), 2.38 (s, 3H), 2.29-2.27 (m, 2H), 2.20 (s, 3H), 2.19-2.18 (m, 2H), 1.77-1.65 (m, 4H); ESI MS m/z 324 [M + H]+. | >99 |

Example 1: Inhibition of Tetra-Acetylated Histone H4 Binding Individual BET Bromodomains Proteins were cloned and overexpressed with a N-terminal 6×His tag, then purified by nickel affinity followed by size exclusion chromatography. Briefly, E. coli BL21(DE3) cells were transformed with a recombinant expression vector encoding N-terminally Nickel affinity tagged bromodomains from Brd2, Brd3, Brd4. Cell cultures were incubated at 37° C. with shaking to the appropriate density and induced overnight with IPTG. The supernatant of lysed cells was loaded onto Ni-IDA column for purification. Eluted protein was pooled, concentrated and further purified by size exclusion chromatography. Fractions representing monomeric protein were pooled, concentrated, aliquoted, and frozen at −80° C. for use in subsequent experiments.

Binding of tetra-acetylated histone H4 and BET bromodomains was confirmed by a Homogenous Time Resolved Fluorescence Resonance Energy Transfer (HTRF®) method. N-terminally His-tagged bromodomains (200 nM) and biotinylated tetra-acetylated histone H4 peptide (25-50 nM, Millipore) were incubated in the presence of Europium Cryptate-labeled streptavidin (Cisbio Cat. #610SAKLB) and XL665-labeled monoclonal anti-His antibody (Cisbio Cat. #61HISXLB) in a white 96 well microtiter plate (Greiner). For inhibition assays, serially diluted test compound was added to these reactions in a 0.2% final concentration of DMSO. Duplicate wells were used for each concentration tested. Final buffer concentrations were 30 mM HEPES pH 7.4, 30 mM NaCl, 0.3 mM CHAPS, 20 mM phosphate pH 7.0, 320 mM KF, 0.08% BSA. After a 2 h incubation at room temperature, fluorescence was measured at 665 and 620 nm with a SynergyH4 plate reader (Biotek). The binding inhibitory activity was shown by a decrease in 665 nm relative to 620 nm fluorescence. $IC_{50}$ values were determined from a dose response curve.

Compounds with an $IC_{50}$ value less than or equal to 0.3 µM were deemed to be highly active (+++); compounds with an $IC_{50}$ value between 0.3 and 3 µM were deemed to be very active (++); compounds with an $IC_{50}$ value between 3 and 30 µM were deemed to be active (+).

TABLE 2

Inhibition of Tetra-acetylated Histone H4 Binding to Brd4 bromodomain 1 (BRD4(1)) as Measured by FRET

| Example Compound | FRET activity BRD4(1) | Example Compound | FRET activity BRD4(1) | Example Compound | FRET activity BRD4(1) |
|---|---|---|---|---|---|
| 1 | +++ | 2 | +++ | 3 | +++ |
| 4 | +++ | 5 | +++ | 6 | +++ |
| 7 | +++ | 8 | +++ | 9 | +++ |
| 10 | +++ | 11 | ++ | 12 | +++ |
| 13 | +++ | 14 | +++ | 15 | +++ |
| 16 | +++ | 17 | +++ | 18 | +++ |
| 19 | +++ | 20 | +++ | 21 | +++ |
| 22 | +++ | 23 | +++ | 24 | +++ |
| 25 | +++ | 26 | +++ | 27 | +++ |
| 28 | +++ | 29 | +++ | 30 | +++ |
| 31 | +++ | 32 | +++ | 33 | +++ |
| 34 | +++ | 35 | +++ | 36 | ++ |
| 37 | ++ | 38 | +++ | 39 | +++ |
| 40 | +++ | 41 | +++ | 42 | +++ |
| 43 | ++ | 44 | ++ | 45 | ++ |
| 46 | +++ | — | — | — | — |

Example 2: Inhibition of c-MYC Expression in Cancer Cell Lines

MV4-11 cells (CRL-9591) were plated at a density of $2.5 \times 10^4$ cells per well in 96 well U-bottom plates and treated with increasing concentrations of test compound or DMSO (0.1%) in IMDM media containing 10% FBS and penicillin/streptomycin, and incubated for 3 h at 37° C. Triplicate wells were used for each concentration. Cells were pelleted by centrifugation and harvested using the mRNA Catcher PLUS kit according to manufacturer's instructions. The eluted mRNA isolated was then used in a one-step quantitative real-time PCR reaction, using components of the RNA UltraSense™ One-Step Kit (Life Technologies) together with Applied Biosystems TaqMan® primer-probes for cMYC and Cyclophilin. Real-time PCR plates were run on a ViiA™7 real time PCR machine (Applied Biosystems), data was analyzed, normalizing the Ct values for hMYC to an internal control, prior to determining the fold expression of each sample, relative to the control.

Compounds with an $IC_{50}$ value less than or equal to 0.3 µM were deemed to be highly active (+++); compounds with an $IC_{50}$ value between 0.3 and 3 µM were deemed to be very active (++); compounds with an $IC_{50}$ value between 3 and 30 µM were deemed to be active (+).

TABLE 3

Inhibition of c-myc Activity in Human AML MV4-11 cells

| Example Compound | c-myc activity | Example Compound | c-myc activity | Example Compound | c-myc activity | Example Compound | c-myc activity |
|---|---|---|---|---|---|---|---|
| 1 | ++ | 2 | +++ | 3 | + | 4 | +++ |
| 5 | +++ | 6 | +++ | 7 | +++ | 8 | ++ |
| 9 | +++ | 10 | +++ | 11 | ++ | 13 | +++ |
| 14 | +++ | 15 | ++ | 16 | +++ | 17 | +++ |
| 18 | ++ | 19 | +++ | 20 | ++ | 21 | +++ |
| 22 | +++ | 23 | +++ | 24 | +++ | 25 | +++ |
| 26 | +++ | 27 | +++ | 28 | ++ | 29 | +++ |

TABLE 3-continued

Inhibition of c-myc Activity in Human AML MV4-11 cells

| Example Compound | c-myc activity | Example Compound | c-myc activity | Example Compound | c-myc activity | Example Compound | c-myc activity |
|---|---|---|---|---|---|---|---|
| 30 | +++ | 31 | ++ | 32 | +++ | 33 | +++ |
| 34 | +++ | 35 | NA | 36 | ++ | 37 | ++ |
| 38 | ++ | 39 | +++ | 40 | +++ | 44 | ++ |
| 45 | +++ | — | — | — | — | — | — |

Example 3: Inhibition of Cell Proliferation in Cancer Cell Lines

In this example, cell titer in MV4-11 cells were quantitated to measure the inhibition of proliferation when treated with a compound of the present disclosure.

MV4-11 cells (CRL-9591) were plated at a density of $5 \times 10^4$ cells per well in 96 well flat bottom plates and treated with increasing concentrations of test compound or DMSO (0.1%) in IMDM media containing 10% FBS and penicillin/streptomycin. Triplicate wells were used for each concentration and a well containing only media was used as a control. Plates were incubated at 37° C., 5% $CO_2$ for 72 h before adding 20 μL of the CellTiter Aqueous One Solution (Promega) to each well and incubated at 37° C., 5% $CO_2$ for an additional 3-4 h. The absorbance was read at 490 nm in a spectrophotometer and the percentage of cell titer relative to DMSO-treated cells was calculated after correcting for background by subtracting the blank well's signal. $IC_{50}$ values were calculated using the Graph Pad Prism software.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

Human leukemic monocyte lymphoma U937 cells (CRL-1593.2) were plated at a density of $3.2 \times 10^4$ cells per well in a 96-well plate in 100 μL RPMI-1640 containing 10% FBS and penicillin/streptomycin, and differentiated into macrophages for 3 days in 60 ng/mL PMA (phorbol-13-myristate-12-acetate) at 37° C. in 5% CO2 prior to the addition of compound. The cells were pretreated for 1 h with increasing concentrations of test compound in 0.1% DMSO prior to stimulation with 1 ug/mL lipopolysaccharide from *Escherichia coli*. Triplicate wells were used for each concentration. The cells were incubated at 37° C., 5% CO2 for 3 h before the cells were harvested. At time of harvest, media was removed and cells were rinsed in 200 μL PBS. Cells were harvested using the mRNA Catcher PLUS kit according to manufacturer's instructions. The eluted mRNA was then used in a one-step quantitative real-time PCR reaction using components of the RNA UltraSense™ One-Step Kit (Life Technologies) together with Applied Biosystems TaqMan® primer-probes for hIL-6 and Cyclophilin. Real-time PCR plates were run on a ViiA™7 real time PCR machine (Applied Biosystems), data was analyzed, normalizing the Ct values for hIL-6 to an internal control, prior to determining the fold expression of each sample, relative to the control.

Compounds with an $IC_{50}$ value less than or equal to 0.3 μM were deemed to be highly active (+++); compounds with an $IC_{50}$ value between 0.3 and 3 μM were deemed to be very active (++); compounds with an $IC_{50}$ value between 3 and 30 μM were deemed to be active (+).

TABLE 4

Inhibition of Cell Proliferation in Human AML MV-4-11 cells

| Example Compound | Cell Proliferation activity | Example Compound | Cell Proliferation activity | Example Compound | Cell Proliferation activity | Example Compound | Cell Proliferation activity |
|---|---|---|---|---|---|---|---|
| 1 | +++ | 2 | ++ | 3 | + | 4 | ++ |
| 5 | +++ | 6 | ++ | 7 | +++ | 8 | ++ |
| 9 | +++ | 10 | +++ | 11 | ++ | 12 | ++ |
| 13 | ++ | 14 | ++ | 15 | ++ | 16 | ++ |
| 17 | ++ | 18 | ++ | 19 | ++ | 20 | +++ |
| 21 | +++ | 22 | +++ | 23 | +++ | 24 | ++ |
| 25 | ++ | 26 | ++ | 27 | ++ | 28 | ++ |
| 29 | ++ | 30 | +++ | 31 | ++ | 32 | ++ |
| 33 | ++ | 34 | ++ | 35 | Not available | 36 | ++ |
| 37 | ++ | 38 | ++ | 39 | ++ | 40 | ++ |
| 44 | + | 45 | ++ | — | — | — | — |

Example 4: Inhibition of hIL-6 mRNA Transcription

In this example, hIL-6 mRNA in tissue culture cells were quantitated to measure the transcriptional inhibition of hIL-6 when treated with a compound of the present disclosure.

TABLE 5

Inhibition of hIL-6 mRNA Transcription

| Example Compound | IL-6 activity | Example Compound | IL-6 activity | Example Compound | IL-6 activity | Example Compound | IL-6 activity |
|---|---|---|---|---|---|---|---|
| 1 | +++ | 2 | +++ | 3 | ++ | 4 | +++ |
| 5 | +++ | 6 | +++ | 7 | +++ | 8 | ++ |
| 9 | +++ | 10 | +++ | 11 | ++ | 12 | ++ |
| 13 | ++ | 16 | ++ | 18 | +++ | 19 | ++ |
| 20 | +++ | 21 | +++ | 22 | +++ | 23 | +++ |
| 26 | ++ | 27 | +++ | 28 | ++ | 29 | ++ |
| 30 | +++ | 31 | +++ | 32 | +++ | 33 | ++ |
| 34 | +++ | 35 | ++ | 38 | ++ | 39 | +++ |
| 40 | ++ | 44 | ++ | 45 | ++ | — | — |

Example 5: Inhibition of hIL-17 mRNA Transcription

In this example, hIL-17 mRNA in human peripheral blood mononuclear cells were quantitated to measure the transcriptional inhibition of hIL-17 when treated with a compound of the present disclosure.

Human peripheral blood mononuclear cells were plated ($2.0 \times 10^5$ cells per well) in a 96-well plate in 45 µL OpTimizer T Cell expansion media (Life Technologies) containing 20 ng/ml IL-2 and penicillin/streptomycin. The cells were treated with increasing concentrations of the test compound or DMSO (0.1%), and incubated at 37° C., 5% $CO2$ for 1 h before addition of 10× stock OKT3 antibody at 10 ug/ml in media. Triplicate wells were used for each concentration. Cells were incubated at 37° C., 5% CO2 for 6 h before the cells were harvested. At time of harvest, cells were pelleted by centrifugation at 800 rpm for 5 min. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems TaqMan® primer-probes for hIL-17 and Cyclophilin. Real-time PCR plates were run on a ViiA™7 real time PCR machine (Applied Biosystems), data was analyzed, normalizing the Ct values for hIL-17 to an internal control, prior to determining the fold induction of each unknown sample, relative to the control.

Compounds with an $IC_{50}$ value less than or equal to 0.3 µM were deemed to be highly active (+++); compounds with an $IC_{50}$ value between 0.3 and 3 µM were deemed to be very active (++); compounds with an $IC_{50}$ value between 3 and 30 µM were deemed to be active (+).

TABLE 6

Inhibition of hIL-17 mRNA Transcription

| Example Compound | IL-17 activity | Example Compound | IL-17 activity |
|---|---|---|---|
| 1 | +++ | 2 | +++ |
| 4 | ++ | 5 | ++ |
| 7 | ++ | 9 | +++ |
| 10 | +++ | 11 | +++ |
| 13 | ++ | 18 | +++ |
| 20 | ++ | 21 | +++ |
| 22 | +++ | 28 | ++ |
| 30 | +++ | – | – |

Example 6: Inhibition of hVCAM mRNA Transcription

In this example, hVCAM mRNA in tissue culture cells is quantitated to measure the transcriptional inhibition of hVCAM when treated with a compound of the present disclosure.

Human umbilical vein endothelial cells (HUVECs) are plated in a 96-well plate ($4.0 \times 10^3$ cells per well) in 100 µL EGM media and incubated for 24 h prior to the addition of increasing concentrations of the compound of interest or DMSO (0.1%). Triplicate wells were used for each concentration. The cells are pretreated for 1 h with the test compound prior to stimulation with tumor necrosis factor-α when they are incubated for an additional 24 h before the cells are harvested. At time of harvest, the spent media is removed and HUVECs are rinsed in 200 µL PBS. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems TaqMan® primer-probes for hVCAM and Cyclophilin. Real-time PCR plates were run on a ViiA™7 real time PCR machine (Applied Biosystems), data was analyzed, normalizing the Ct values for hVCAM to an internal control, prior to determining the fold induction of each unknown sample, relative to the control.

Example 7: Inhibition of hMCP-1 mRNA Transcription

In this example, hMCP-1 mRNA in human peripheral blood mononuclear cells is quantitated to measure the transcriptional inhibition of hMCP-1 when treated with a compound of the present disclosure.

Human Peripheral Blood Mononuclear Cells are plated at a density of $1.0 \times 10^5$ cells per well in a 96-well plate in RPMI-1640 containing 10% FBS and penicillin/streptomycin. The cells are treated with increasing concentrations of the compound or DMSO (0.1%), and incubated at 37° C., 5% CO2 for 3 h before the cells are harvested. At time of harvest, cells are transferred to V-bottom plates and pelleted by centrifugation at 800 rpm for 5 min. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems TaqMan® primer-probes for hMCP-1 and Cyclophilin. Real-time PCR plates were run on a ViiA™7 real time PCR machine (Applied Biosystems), data was analyzed, normalizing the Ct values for hMCP-1 to an internal control, prior to determining the fold induction of each unknown sample, relative to the control.

Example 8: Up-Regulation of hApoA-1 mRNA Transcription

In this example, hApoA-I mRNA in tissue culture cells was quantitated to measure the transcriptional up-regulation of hApoA-I when treated with a compound of the present disclosure.

Huh7 cells ($2.5 \times 10^5$ per well) were plated in a 96-well plate using 100 µL DMEM per well, (Gibco DMEM supplemented with penicillin/streptomycin and 10% FBS), 72 h before the addition of the compound. The cells are treated with increasing concentrations of the compound or DMSO (0.1%), and incubated at 37° C., 5% CO2 for 48 h. Spent media was removed from the Huh-7 cells and placed on ice for immediate use with the "LDH cytotoxicity assay Kit II" from Abcam. The cells remaining in the plate were rinsed with 100 µL PBS. Cells were harvested using the mRNA Catcher PLUS kit according to manufacturer's instructions. The eluted mRNA was then used in a one-step quantitative real-time PCR reaction, using components of the RNA UltraSense™ One-Step Kit (Life Technologies) together with Applied Biosystems TaqMan® primer-probes for hApoA-I and Cyclophilin. Real-time PCR plates were run on a ViiA™7 real time PCR machine (Applied Biosystems), data was analyzed, normalizing the Ct values for hApoA-1 to an internal control, prior to determining the fold induction of each unknown sample, relative to the control.

Compounds with an $EC_{170}$ value less than or equal to 0.3 µM were deemed to be highly active (+++); compounds with an $EC_{170}$ value between 0.3 and 3 µM were deemed to be very active (++); compounds with an $EC_{170}$ value between 3 and 30 µM were deemed to be active (+).

TABLE 7

Up-regulation of hApoA-1 mRNA Transcription.

| Example Compound | ApoA-1 activity | Example Compound | ApoA-1 activity | Example Compound | ApoA-1 activity |
|---|---|---|---|---|---|
| 1 | +++ | 4 | +++ | 7 | +++ |
| 9 | +++ | 13 | +++ | — | — |

Example 9: In Vivo Efficacy in Athymic Nude Mouse Strain of an Acute Myeloid Leukemia Xenograft Model Using MV4-11 Cells MV4-11 cells (ATCC) were grown under standard cell culture conditions and (NCr) nu/nu fisol strain of female mice age 6-7 weeks were injected with $5 \times 10^6$ cells/animal in 100 µL PBS+100 µL Matrigel in the lower left abdominal flank. By approximately day 18-21 after MV4-11 cells injection, mice were randomized based on tumor volume (L×W×H)/2) of average ~100-300 mm³. Mice were dosed orally with compound at 5 to 120 mg/kg b.i.d and/or q.d. on a continuous dosing schedule and at 2.5 to 85 mg/kg q.d. on a 5 day on 2 day off, 100 mg/kg q.d. on a 4 day on and 3 day off, 135 mg/kg q.d. on a 3 day on and 4 day off, 180 mg/kg on a 2 day on and 5 day off and 240 mg/kg on a 1 day on and 6 days off dosing schedules in EA006 formulation at 10 mL/kg body weight dose volume. Tumor measurements were taken with electronic micro calipers and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using Student's t-test in Excel.

TABLE 8

In vivo efficacy in athymic nude mouse strain of an acute myeloid leukemia xenograft model

| Example Compound | In vivo activity |
|---|---|
| Example 9 | Active |

Example 10: In Vivo Efficacy in Athymic Nude Mouse Strain of an Acute Myeloid Leukemia Xenograft Model Using OCI-3 AML Cells OCI-3 AML cells (DMSZ) were grown under standard cell culture conditions and (NCr) nu/nu fisol strain of female mice age 6-7 weeks were injected with $10 \times 10^6$ cells/animal in 100 µL PBS+100 µL Matrigel in the lower left abdominal flank. By approximately day 18-21 after OCI-3 AML cells injection, mice were randomized based on tumor volume (L×W×H)/2) of average ~100-300 mm³. Mice were dosed orally with compound at 30 mg/kg b.i.d on a continuous dosing schedule and at 2.5 to 45 mg/kg q.d. on a 5 day on and 2 day off dosing schedule in EA006 formulation at 10 mL/kg body weight dose volume. Tumor measurements were taken with electronic micro calipers and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using Student's t-test in Excel.

TABLE 9

In vivo efficacy in athymic nude mouse strain of an acute myeloid leukemia xenograft model using OCI-3 AML cells

| Example Compound | In vivo activity |
|---|---|
| Example 9 | Active |

Example 11: Evaluation of Target Engagement

MV4-11 and MM1.s cells (ATCC) were grown under standard cell culture conditions and (NCr) nu/nu fisol strain of female mice age 6-7 weeks were injected with $5 \times 10^6$ cells/animal in 100 µL PBS+100 µL Matrigel in the lower left abdominal flank. By approximately day 28 after MV4-11 and MM1.s cells injection, mice were randomized based on tumor volume (L×W×H)/2) of average ~500 mm³. Mice were dosed orally with compound in EA006 formulation at 10 mL/kg body weight dose volume and tumors harvested 3, 6, 12, 24 hrs post dose for Bcl2 and c-myc gene expression analysis as PD biomarkers.

TABLE 10

Evaluation of Target Engagement.

| Example Compound | In vivo activity |
|---|---|
| Example 9 | Active |

Example 12: In Vivo Efficacy in Athymic Nude Mouse Strain of Multiple Myeloma Xenograft Model Using MM1.s Cells MM1.s cells (ATCC) were grown under standard cell culture conditions and SCID-Beige strain of female mice age 6-7 weeks were injected with $10 \times 10^6$ cells/animal in 100 μL PBS+100 μL Matrigel in the lower left abdominal flank. By approximately day 21 after MM1.s cells injection, mice were randomized based on tumor volume (L×W×H)/2) of average ~120 mm³. Mice were dosed orally with compound at 25 to 90 mg/kg b.i.d and or q.d in EA006 formulation at 10 mL/kg body weight dose volume. Tumor measurements were taken with electronic micro calipers and body weights measured on alternate days beginning from dosing period. The average tumor volumes, percent Tumor Growth Inhibition (TGI) and % change in body weights were compared relative to Vehicle control animals. The means, statistical analysis and the comparison between groups were calculated using Student's t-test in Excel.

TABLE 11

In vivo efficacy in athymic nude mouse strain of multiple myeloma xenograft model using MM1.s cells

| Example Compound | In vivo activity |
|---|---|
| Example 9 | Active |

Example 13: In Vivo Efficacy in Mouse Endotoxemia Model Assay

Sub lethal doses of Endotoxin (*E. Coli* bacterial lipopolysaccharide) are administered to animals to produce a generalized inflammatory response which is monitored by increases in secreted cytokines. Compounds are administered to C57/Bl6 mice at T=4 hours orally at 75 mg/kg dose to evaluate inhibition in IL-6 and IL-17 and MCP-1 cytokines post 3-h challenge with lipopolysaccharide (LPS) at T=0 hours at 0.5 mg/kg dose intraperitoneally.

Example 14: In Vivo Efficacy in Rat Collagen-Induced Arthritis

Rat collagen-induced arthritis is an experimental model of polyarthritis that has been widely used for preclinical testing of numerous anti-arthritic agents. Following administration of collagen, this model establishes a measurable polyarticular inflammation, marked cartilage destruction in association with pannus formation and mild to moderate bone resorption and periosteal bone proliferation. In this model, collagen was administered to female Lewis strain of rats on Day 1 and 7 of study and dosed with compounds from Day 11 to Day 17. Test compounds were evaluated to assess the potential to inhibit the inflammation (including paw swelling), cartilage destruction and bone resorption in arthritic rats, using a model in which the treatment is administered after the disease has been established.

Example 15: In Vivo Efficacy in Experimental Autoimmune Encephalomyelitis (EAE) Model of MS Experimental autoimmune encephalomyelitis (EAE) is a T-cell-mediated autoimmune disease of the CNS which shares many clinical and histopathological features with human multiple sclerosis (MS). EAE is the most commonly used animal model of MS. T cells of both Th1 and Th17 lineage have been shown to induce EAE. Cytokines IL-23, IL-6 and IL-17, which are either critical for Th1 and Th17 differentiation or produced by these T cells, play a critical and non-redundant role in EAE development. Therefore, drugs targeting production of these cytokines are likely to have therapeutic potential in treatment of MS.

Compounds of Formula I were administered to EAE mice to assess anti-inflammatory activity. In this model, EAE is induced by $MOG_{35-55}$/CFA immunization and pertussis toxin injection in female C57Bl/6 mice.

Example 16: Ex Vivo Effects on T Cell Function from Splenocyte and Lymphocyte Cultures Stimulated with External MOG Stimulation Mice were immunized with MOG/CFA and simultaneously treated with the compound for 11 days on a b.i.d regimen. Inguinal Lymph node and spleen were harvested, cultures were set up for lymphocytes and splenocytes and stimulated with external antigen (MOG) for 72 hours. Supernatants from these cultures were analyzed for TH1, Th2 and Th17 cytokines using a Cytometric Bead Array assay.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A method for treating prostate cancer in a mammal, comprising administering a therapeutically effective amount of a compound of formula:

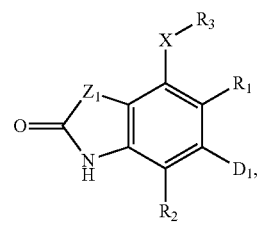

or a tautomer, pharmaceutically acceptable salt, or hydrate thereof,
wherein:
$D_1$ is selected from isoxazole, optionally substituted with one or more groups independently selected from deuterium, alkyl($C_1$-$C_4$), alkoxy($C_1$-$C_4$), amino, halogen, amide, —C(O)cycloamino, —$CF_3$, CN, —$N_3$, ketone ($C_1$-$C_4$), —S(O)Alkyl($C_1$-$C_4$), —$SO_2$alkyl($C_1$-$C_4$), -thioalkyl($C_1$-$C_4$), —COOH, and ester, wherein said alkyl($C_1$-$C_4$), alkoxy($C_1$-$C_4$), amino, amide, ketone ($C_1$-$C_4$), —S(O)Alkyl($C_1$-$C_4$), —$SO_2$alkyl($C_1$-$C_4$), -thioalkyl($C_1$-$C_4$), and ester are optionally substituted with one or more groups independently selected from hydrogen, F, Cl, Br, —OH, —NH$_2$, —NHMe, —OMe, —SMe, oxo, and thio-oxo;

X is present and selected from —(NH)—, —O—, —NHCR$_x$R$_y$—, —NHSO$_2$—, and —CR$_x$R$_y$NH—;

Z$_1$ is —NR$_a$;

R$_a$ is selected from hydrogen, deuterium, and alkyl (C$_{1-3}$);

R$_3$ is selected from isoxazole, pyrazole, pyridyl, thiazole, isothiazole, pyrimidine, phenyl, cyclohexene, benzo[d]oxazolyl, naphthyl, and quinolyl, optionally substituted with one or more groups independently selected from deuterium, alkyl(C$_1$-C$_4$), —OH, alkoxy(C$_1$-C$_4$), amino, halogen, amide, —CF$_3$, CN, —N$_3$, ketone (C$_1$-C$_4$), —S(O)Alkyl(C$_1$-C$_4$), —SO$_2$alkyl(C$_1$-C$_4$), -thioalkyl (C$_1$-C$_4$), carboxyl, and ester,
wherein said alkyl(C$_1$-C$_4$), alkoxy(C$_1$-C$_4$), amino, amide, ketone (C$_1$-C$_4$), —S(O)Alkyl(C$_1$-C$_4$), —SO$_2$alkyl(C$_1$-C$_4$), -thioalkyl(C$_1$-C$_4$), and ester are optionally substituted with one or more groups independently selected from hydrogen, F, Cl, Br, —OH, —NH$_2$, —NHMe, —OMe, —SMe, oxo, and/or thio-oxo;

R$_1$ and R$_2$ are independently selected from hydrogen, deuterium, alkyl, —OH, —NH$_2$, -thioalkyl, and alkoxy; and R$_x$ and R$_y$ are each independently selected from hydrogen, alkyl(C$_{1-5}$), halogen, —OH, —CF$_3$, deuterium, amino, and alkoxy(C$_{1-5}$), or two substituents selected from R$_x$, R$_y$ and R$_1$ may be connected in a 5- or 6-membered ring to form a bicyclic carbocycle or bicyclic heterocycle.

2. The method of claim 1, wherein D$_1$ is

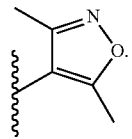

3. A method for treating prostate cancer in a mammal, comprising administering a therapeutically effective amount of a compound selected from:
5-(3,5-dimethylisoxazol-4-yl)-1-methyl-7-(2-(trifluoromethyl)phenyl)-1H-benzo[d]imidazol-2(3H)-one;
5-(3,5-dimethylisoxazol-4-yl)-1-methyl-7-(2-(trifluoromethyl)pyridin-3-yl)-1H-benzo[d]imidazol-2(3H)-one;
5-(3,5-dimethylisoxazol-4-yl)-1-methyl-7-(1,3,5-trimethyl-1H-pyrazol-4-yl)-1H-benzo[d]imidazol-2(3H)-one;
5-(3,5-dimethylisoxazol-4-yl)-1-methyl-7-(4-methylisothiazol-5-yl)-1H-benzo[d]imidazol-2(3H)-one;
5-(3,5-dimethylisoxazol-4-yl)-7-(4-fluoro-2-(trifluoromethyl)phenyl)-1-methyl-1H-benzo[d]imidazol-2(3H)-one;
5-(3,5-dimethylisoxazol-4-yl)-7-(2-methoxy-5-methyl phenyl)-1-methyl-1H-benzo[d]imidazol-2(3H)-one;
5-(3,5-dimethylisoxazol-4-yl)-7-(2-methoxypyridin-3-yl)-1-methyl-1H-benzo[d]imidazol-2(3H)-one;
3-(6-(3,5-dimethylisoxazol-4-yl)-3-methyl-2-oxo-2,3-dihydro-1H-benzo[d]imidazol-4-yl)-2-methylbenzonitrile;
4,6-bis(3,5-dimethylisoxazol-4-yl)-1,3-dimethyl-1H-benzo[d]imidazol-2(3H)-one;
3-(6-(3,5-dimethylisoxazol-4-yl)-3-methyl-2-oxo-2,3-dihydro-1H-benzo[d]imidazol-4-yl)-4-methylbenzonitrile;
5-(3,5-dimethylisoxazol-4-yl)-7-(4-methoxypyridin-3-yl)-1-methyl-1H-benzo[d]imidazol-2(3H)-one;
5-(3,5-dimethylisoxazol-4-yl)-7-(5-fluoro-2-methoxyphenyl)-1-methyl-1H-benzo[d]imidazol-2(3H)-one;
7-(5-chloro-2-methylphenyl)-5-(3,5-dimethylisoxazol-4-yl)-1-methyl-1H-benzo[d]imidazol-2(3H)-one;
7-(6-amino-2-methylpyridin-3-yl)-5-(3,5-dimethylisoxazol-4-yl)-1-methyl-1H-benzo[d]imidazol-2(3H)-one;
7-(3,5-dimethyl-1H-pyrazol-4-yl)-5-(3,5-dimethylisoxazol-4-yl)-1-methyl-1H-benzo[d]imidazol-2(3H)-one;
6-(3,5-dimethylisoxazol-4-yl)-4-(1,3,5-trimethyl-1H-pyrazol-4-yl)-1H-benzo[d]imidazol-2(3H)-one;
6-(3,5-dimethylisoxazol-4-yl)-4-(1,3,5-trimethyl-1H-pyrazol-4-yl)-1H-benzo[d]imidazole-2(3H)-thione;
6-(3,5-dimethylisoxazol-4-yl)-4-(4-methylpyridin-3-yl)-1H-benzo[d]imidazole-2-thiol;
3-(6-(3,5-dimethylisoxazol-4-yl)-2-thioxo-2,3-dihydro-1H-benzo[d]imidazol-4-yl)-4-methylbenzonitrile;
5-(3,5-dimethylisoxazol-4-yl)-1-methyl-7-((1,3,5-trimethyl-1H-pyrazol-4-yl)amino)-1H-benzo[d]imidazol-2(3H)-one;
5-(3,5-dimethylisoxazol-4-yl)-1-methyl-7-((2-methylpyridin-3-yl)amino)-1H-benzo[d]imidazol-2(3H)-one;
5-(5-(hydroxymethyl)-3-methylisoxazol-4-yl)-1-methyl-7-(1,3,5-trimethyl-1H-pyrazol-4-yl)-1H-benzo[d]imidazol-2(3H)-one;
3-(6-(3,5-dimethylisoxazol-4-yl)-3-methyl-2-oxo-2,3-dihydro-1H-benzo[d]imidazol-4-yl)-4-methylbenzamide;
3-(6-(3,5-dimethylisoxazol-4-yl)-3-methyl-2-oxo-2,3-dihydro-1H-benzo[d]imidazol-4-yl)-2-methylbenzamide;
5-(3,5-dimethylisoxazol-4-yl)-1-methyl-7-((2-methylpyridin-3-yl)oxy)-1H-benzo[d]imidazol-2(3H)-one;
7-(3,5-dimethyl-1H-pyrazol-4-yl)-5-(5-(hydroxymethyl)-3-methylisoxazol-4-yl)-1-methyl-1H-benzo[d]imidazol-2(3H)-one;
5-(3,5-dimethylisoxazol-4-yl)-7-((3,5-dimethylisoxazol-4-yl)amino)-1-methyl-1H-benzo[d]imidazol-2(3H)-one;
7-(3,5-dichloropyridin-4-yl)-5-(3,5-dimethylisoxazol-4-yl)-1-methyl-1H-benzo[d]imidazol-2(3H)-one;
7-(2-chlorophenyl)-5-(3,5-dimethylisoxazol-4-yl)-1-methyl-1H-benzo[d]imidazol-2(3H)-one;
5-(3,5-dimethylisoxazol-4-yl)-1-methyl-7-(3-methylpyridin-4-yl)-1H-benzo[d]imidazol-2(3H)-one;
5-(3,5-dimethylisoxazol-4-yl)-1-methyl-7-(o-tolyl)-1H-benzo[d]imidazol-2(3H)-one;
5-(3,5-dimethylisoxazol-4-yl)-7-(2-fluoro-5-methoxyphenyl)-1-methyl-1H-benzo[d]imidazol-2(3H)-one;
7-(5-chloro-2-methoxyphenyl)-5-(3,5-dimethylisoxazol-4-yl)-1-methyl-1H-benzo[d]imidazol-2(3H)-one;
5-(3,5-dimethylisoxazol-4-yl)-7-(2-fluoro-3-methoxyphenyl)-1-methyl-1H-benzo[d]imidazol-2(3H)-one;
5-(3,5-dimethylisoxazol-4-yl)-7-(2,4-dimethylthiazol-5-yl)-1-methyl-1H-benzo[d]imidazol-2(3H)-one;
5-(3,5-dimethylisoxazol-4-yl)-7-(2-methoxy-6-methyl pyridin-3-yl)-1-methyl-1H-benzo[d]imidazol-2(3H)-one;
7-(benzo[d]oxazol-5-yl)-5-(3,5-dimethyl isoxazol-4-yl)-1-methyl-1H-benzo[d]imidazol-2(3H)-one;
7-(cyclohex-1-en-1-yl)-5-(3,5-dimethylisoxazol-4-yl)-1-methyl-1H-benzo[d]imidazol-2(3H)-one; and
tautomers, pharmaceutically acceptable salts, and hydrates thereof.

4. The method of claim 1, 2, or 3, wherein the compound is administered in combination with another anticancer agent.

5. The method of claim 4, wherein the anticancer agent is selected from ABT-737, Azacitidine (Vidaza), AZD1152 (Barasertib), AZD2281 (Olaparib), AZD6244 (Selumetinib), BEZ235, Bleomycin Sulfate, Bortezomib (Velcade), Busulfan (Myleran), Camptothecin, Cisplatin, Cyclophosphamide (Clafen), CYT387, Cytarabine (Ara-C), Dacarbazine, DAPT (GSI-IX), Decitabine, Dexamethasone, Doxorubicin (Adriamycin), Etoposide, Everolimus (RAD001), Flavopiridol (Alvocidib), Ganetespib (STA-9090), Gefitinib (Iressa), Idarubicin, Ifosfamide (Mitoxana), IFNa2a (Roferon A), Melphalan (Alkeran), Methazolastone (temozolomide), Metformin, Mitoxantrone (Novantrone), Paclitaxel, Phenformin, PKC412 (Midostaurin), PLX4032 (Vemurafenib), Pomalidomide (CC-4047), Prednisone (Deltasone), Rapamycin, Revlimid (Lenalidomide), Ruxolitinib (INCB018424), Sorafenib (Nexavar), SU11248 (Sunitinib), SU11274, Vinblastine, Vincristine (Oncovin), Vinorelbine (Navelbine), Vorinostat (SAHA), and WP1130 (Degrasyn).

\* \* \* \* \*